(12) United States Patent
Chapman et al.

(10) Patent No.: US 11,971,409 B2
(45) Date of Patent: *Apr. 30, 2024

(54) METHODS OF PRODUCING PATIENT-SPECIFIC ANTI-CANCER THERAPEUTICS AND METHODS OF TREATMENT THEREFOR

(71) Applicant: Berkeley Lights, Inc., Emeryville, CA (US)

(72) Inventors: Kevin T. Chapman, Emeryville, CA (US); Mark P. White, Orinda, CA (US); Xiaohua Wang, Pomona, NY (US); Minha Park, Brisbane, CA (US); Guido K. Stadler, San Francisco, CA (US); Randall D. Lowe, Jr., Emeryville, CA (US); Xiao Guan Radstrom, San Rafael, CA (US); Jason M. McEwen, El Cerrito, CA (US); Gang F. Wang, Mountain View, CA (US); George L. Fox, Albany, CA (US); Peggy A. Radel, Berkeley, CA (US)

(73) Assignee: Bruker Cellular Analysis, Inc., Emeryville, CA (US)

( * ) Notice: Subject to any disclaimer, the term of this patent is extended or adjusted under 35 U.S.C. 154(b) by 506 days.

This patent is subject to a terminal disclaimer.

(21) Appl. No.: 16/892,642

(22) Filed: Jun. 4, 2020

(65) Prior Publication Data

US 2020/0400669 A1 Dec. 24, 2020

Related U.S. Application Data

(63) Continuation of application No. 15/406,289, filed on Jan. 13, 2017, now Pat. No. 10,712,344.
(Continued)

(51) Int. Cl.
*B01L 3/00* (2006.01)
*C07K 16/00* (2006.01)
(Continued)

(52) U.S. Cl.
CPC ...... *G01N 33/574* (2013.01); *B01L 3/502761* (2013.01); *C07K 16/00* (2013.01);
(Continued)

(58) Field of Classification Search
None
See application file for complete search history.

(56) References Cited

U.S. PATENT DOCUMENTS

| 6,294,063 B1 | 9/2001 | Becker et al. |
| 6,942,776 B2 | 9/2005 | Medoro |

(Continued)

FOREIGN PATENT DOCUMENTS

| CN | 101275114 A | 10/2008 |
| CN | 101646775 A | 2/2010 |

(Continued)

OTHER PUBLICATIONS

Machine Translation of JPH03120226, May 22, 1991, 7 pages.
(Continued)

*Primary Examiner* — Rebecca M Giere
(74) *Attorney, Agent, or Firm* — McNeill Baur PLLC

(57) ABSTRACT

A method of preparing an antibody therapeutic is provided comprising: (a) providing a dissociated cell sample from at least one solid tumor sample obtained from a patient; (b) loading the dissociated cell sample into a microfluidic device having a flow region and at least one isolation region fluidically connected to the flow region; (c) moving at least one B cell from the dissociated cell sample into at least one isolation region in the microfluidic device, thereby obtaining at least one isolated B cell; and (d) using the microfluidic
(Continued)

device to identify at least one B cell that produces antibodies capable of binding to cancer cells. The cancer cells can be the patient's own cancer cells. Also provided are methods of treating patients, methods of labeling or detecting cancer, engineered T or NK cells comprising antibodies or fragments thereof, and engineered antibody constructs.

22 Claims, 13 Drawing Sheets

Related U.S. Application Data

(60) Provisional application No. 62/279,341, filed on Jan. 15, 2016, provisional application No. 62/411,690, filed on Oct. 23, 2016, provisional application No. 62/412,092, filed on Oct. 24, 2016.

(51) Int. Cl.
*C07K 16/28* (2006.01)
*C07K 16/30* (2006.01)
*C12Q 1/6886* (2018.01)
*G01N 33/50* (2006.01)
*G01N 33/543* (2006.01)
*G01N 33/569* (2006.01)
*G01N 33/574* (2006.01)

(52) U.S. Cl.
CPC .......... *C07K 16/2887* (2013.01); *C07K 16/30* (2013.01); *C12Q 1/6886* (2013.01); *G01N 33/5047* (2013.01); *G01N 33/505* (2013.01); *G01N 33/5052* (2013.01); *G01N 33/54366* (2013.01); *G01N 33/56972* (2013.01); *B01L 2200/0647* (2013.01); *G01N 2800/7028* (2013.01)

(56) References Cited

U.S. PATENT DOCUMENTS

| | | |
|---|---|---|
| 6,958,132 B2 | 10/2005 | Chiou et al. |
| 7,090,759 B1 | 8/2006 | Seul |
| 7,223,364 B1 | 5/2007 | Johnston et al. |
| 7,612,355 B2 | 11/2009 | Wu et al. |
| 7,956,339 B2 | 6/2011 | Ohta et al. |
| RE44,711 E | 1/2014 | Wu et al. |
| 8,685,344 B2 | 4/2014 | Sudarsan et al. |
| 10,712,344 B2 | 7/2020 | Chapman et al. |
| 2003/0008364 A1 | 1/2003 | Wang et al. |
| 2004/0072278 A1 | 4/2004 | Chou et al. |
| 2004/0191789 A1 | 9/2004 | Manaresi et al. |
| 2004/0197905 A1 | 10/2004 | Hafeman |
| 2005/0112548 A1 | 5/2005 | Segawa et al. |
| 2005/0129581 A1 | 6/2005 | McBride et al. |
| 2005/0175981 A1 | 8/2005 | Voldman et al. |
| 2006/0091015 A1 | 5/2006 | Lau |
| 2006/0154361 A1 | 7/2006 | Wikswo et al. |
| 2006/0286117 A1 | 12/2006 | Fine et al. |
| 2007/0095669 A1 | 5/2007 | Lau et al. |
| 2007/0183934 A1 | 8/2007 | Diercks et al. |
| 2008/0223721 A1 | 9/2008 | Cohen et al. |
| 2008/0302732 A1 | 12/2008 | Soh et al. |
| 2009/0023608 A1 | 1/2009 | Hung et al. |
| 2009/0170186 A1 | 7/2009 | Wu et al. |
| 2010/0003666 A1 | 1/2010 | Lee et al. |
| 2010/0035292 A1 | 2/2010 | Levhenko et al. |
| 2010/0086919 A1 | 4/2010 | McKeon |
| 2010/0101960 A1 | 4/2010 | Ohta et al. |
| 2010/0273681 A1 | 10/2010 | Cerrina et al. |
| 2011/0053151 A1 | 3/2011 | Hansen et al. |
| 2011/0117634 A1 | 5/2011 | Halamish et al. |
| 2011/0143964 A1 | 6/2011 | Zhou et al. |
| 2011/0236393 A1 | 9/2011 | Hwang et al. |
| 2011/0262906 A1 | 10/2011 | Dimov et al. |
| 2012/0009671 A1 | 1/2012 | Hansen et al. |
| 2012/0015347 A1 | 1/2012 | Singhal et al. |
| 2012/0015382 A1 | 1/2012 | Weitz et al. |
| 2012/0024708 A1 | 2/2012 | Chiou et al. |
| 2012/0118740 A1 | 5/2012 | Garcia et al. |
| 2012/0156675 A1 | 6/2012 | Lueerssen et al. |
| 2012/0325665 A1 | 12/2012 | Chiou et al. |
| 2013/0115606 A1 | 5/2013 | Hansen et al. |
| 2013/0118905 A1 | 5/2013 | Morimoto et al. |
| 2013/0130232 A1 | 5/2013 | Weibel et al. |
| 2013/0171628 A1 | 7/2013 | Carlo et al. |
| 2013/0190212 A1 | 7/2013 | Handique et al. |
| 2013/0204076 A1 | 8/2013 | Han et al. |
| 2013/0261021 A1 | 10/2013 | Bocchi et al. |
| 2014/0116881 A1 | 5/2014 | Chapman et al. |
| 2014/0124370 A1 | 5/2014 | Short et al. |
| 2014/0154703 A1 | 6/2014 | Skelley et al. |
| 2015/0004253 A1 | 1/2015 | Dieu-Nosjean et al. |
| 2015/0018226 A1 | 1/2015 | Hansen et al. |
| 2015/0151298 A1 | 6/2015 | Hobbs et al. |
| 2015/0151307 A1 | 6/2015 | Breinlinger et al. |
| 2015/0165436 A1 | 6/2015 | Chapman et al. |
| 2015/0306598 A1 | 10/2015 | Khandros et al. |
| 2015/0306599 A1 | 10/2015 | Khandros et al. |
| 2016/0184821 A1 | 6/2016 | Hobbs et al. |
| 2016/0193604 A1 | 7/2016 | McFarland et al. |
| 2016/0199837 A1 | 7/2016 | Breinlinger et al. |
| 2016/0252495 A1 | 9/2016 | Ricicova et al. |
| 2016/0312165 A1 | 10/2016 | Lowe et al. |
| 2017/0248583 A1 | 8/2017 | Simmons et al. |
| 2018/0099282 A1 | 4/2018 | Breinlinger et al. |
| 2018/0298318 A1 | 10/2018 | Kurz et al. |
| 2019/0240665 A1 | 8/2019 | Lionberger et al. |
| 2019/0275516 A1 | 9/2019 | Lowe, Jr. et al. |

FOREIGN PATENT DOCUMENTS

| | | |
|---|---|---|
| CN | 102439127 A | 5/2012 |
| CN | 103502426 A | 1/2014 |
| CN | 104293666 A | 1/2015 |
| EP | 0421380 B1 | 12/1995 |
| JP | H03120226 A | 5/1991 |
| JP | 2004532968 A | 10/2004 |
| JP | 2015529468 A | 10/2015 |
| KR | 1020130009760 A | 1/2013 |
| WO | 2001096025 A2 | 12/2001 |
| WO | 2004044584 A1 | 5/2004 |
| WO | 2004089810 A2 | 10/2004 |
| WO | 2007008609 A2 | 1/2007 |
| WO | 2007024701 A2 | 3/2007 |
| WO | 2007092713 A2 | 8/2007 |
| WO | 2008083150 A2 | 7/2008 |
| WO | 2009130694 A2 | 10/2009 |
| WO | 2009151505 A1 | 12/2009 |
| WO | 2010040851 A2 | 4/2010 |
| WO | 2010104828 A2 | 9/2010 |
| WO | 2010147078 A1 | 12/2010 |
| WO | 2011100403 A1 | 8/2011 |
| WO | 2011160430 A1 | 12/2011 |
| WO | 2012037030 A2 | 3/2012 |
| WO | 2012072823 A1 | 6/2012 |
| WO | 2012118799 A2 | 9/2012 |
| WO | 2012162779 A1 | 12/2012 |
| WO | 2013019491 A1 | 2/2013 |
| WO | 2014043365 A1 | 3/2014 |
| WO | 2014153651 A1 | 10/2014 |
| WO | 2015061497 A1 | 4/2015 |
| WO | 2015164846 A1 | 10/2015 |
| WO | 2015164847 A1 | 10/2015 |
| WO | 2015188171 A1 | 12/2015 |

OTHER PUBLICATIONS

Bi et al., "Deposition of PEG onto PMMA microchannel surface to minimize nonspecific adsorption," Lap Chip, 2006, 6:769-775.
Ozawa et al., "Amplification and analysis of cDNA generated from a single cell by 5'-RACE: application to isolation of antibody heavy

(56) References Cited

OTHER PUBLICATIONS and light chain variable gene sequences from single B cells," BioTechniques, 2006, 40:469-478.
CN101275114A, Luo—Machine Translation, Oct. 1, 2008, 8 pages.
CN104293666A, Univ Dalian_Liu, Machine Translation from espacenet, Jan. 21, 2015, 5 pages.
Hung et al., "Continuous Perfusion Microfluidic Cell Culture Array for High-Throughput Cell-Based Assays", Biotech and Bioengineering, 2004, 89(1): 1-8.
Liescu et al., "Continuous Field-Flow Separation of Particle Populations in a Dielectrophoretic Chip with Three Dimensional Electrodes," Applied Physics Letters, 2007, 90:234104.
Somaweera H. et al., "Generation of a Chemical Gradient Across an Array of 256 Cell Cultures in a Single Chip," Analyst, 2013, 138(19): 5566-5571.
WO2010147078, University of Tokyo, Machine Translation, Dec. 23, 2010, 12 pages.
Yi et al., "Microfluidics technology for manipulation and analysis of biological cells," Analytica Chimica Acta, 2006, 560:1-23.
Bacheleitner-Hoffmann et al., Stimulation of Autologous Antitumor T-Cell Responses Against Medullary Thyroid Carcinoma Using Tumor Lysate-Pulsed Dendritic Cells, J. Clin. Endo. & Metabl. 87(3): 1098-1104 (2002).
Brenner MK. CAR T Cells for Acute Myeloid Leukemia: The LeY of the Land. Molecular Therapy. 21(11):1983-4. Nov. 2013.
CAR-T Cell Therapy webpage. Downloaded from site: http://www.cancer.gov/cancertopics/research-updates/2013/CAR-T-Cells#improving on Mar. 30, 2015.
Chung et al., Imaging single-cell signaling dynamics with a deterministic high-density single-cell trap array, Anal. Chem.83(18):7044-7052 (2011).
Collarini et al., Potent High-Affinity Antibodies for Treatment and Prophylaxis of Respiratory Synctial Virus Derived from B Cells of Infected Patients, J. Immunol., 183: 6338-6345 (2009).
Curran KJ, et al. Chimeric antigen receptors for T cell immunotherapy: current understanding and future directions. J Gene Med. 14:405-415. 2012.
Dicarlo et al., "Dynamic Single Cell Analysis for Quantitative Biology," Analytical Chemistry (Dec. 1, 2006), pp. 7918-7925.
Germain et al., Tertiary lymphoid structure-associated B cells are key players in anti-tumor immunity, Frontiers in Immunology, 6: Article 67, 1-14 (2015).
Globerson-Levin, A. et al., "Elimination of progressive mammary cancer by repeated administrations of chimeric antigen receptor-modified T cells" Mol Ther, Feb. 27, 2014, vol. 22, No. 5, pp. 1029-1038.
Goc J, et al. Characteristics of tertiary lymphoid structures in primary cancers. OncoImmunology. 2(12):e26836. Dec. 2013.
Harbeck, "Model System for isolation of competent ovarian carcinoma cells from fresh tumor tissue by a magnetic separation technique (MACS)", International Journal of Oncology 6: 1995; 6 pages.
He et al., In vitro generation of cytotoxic T lymphocyte response using dendritic cell immunotherapy in osteosarcoma, Oncology Letters 12: 1101-1106 (2016).
Lee, Gi-Hun et al. "Separation and sorting of cells in microsystems using physical principles", Journal of Micromechanics & Microengineering, Institute of Physics Publishing, Bristol, GB, vol. 26, No. 1, Dec. 16, 2015 (Dec. 16, 2015), p. 13003.
Li, Q. et al., "In vivo sensitized and in vitro activated B cells mediate tumor regression in cancer adoptive immunotherapy" J Immunol, Aug. 10, 2009, vol. 183, No. 5, pp. 3195-3203.
Lucio, "Flow Cytometric analysis of normal B cell differentiation: a from of reference for the detection of minimal residual disease in precursor-B-ALL", Leukemia 1999, 10 pages.
Martucci, "Nanoparticle-based strategy for personalized B-cell lymphoma therapy", International Journal of Nanomedicine, 2016:11, 14 pages.
Metildi CA, et al. Fluorescence-guided Surgery with a Fluorophore-conjugated Antibody to Carcinoembryonic Antigen (CEA), that Highlights the Tumor, Improves Surgical Resection and Increases Survival in Orthotopic Mouse Models of Human Pancreatic Cancer. Ann Surg Oncol. 21(4):1405-1411. Apr. 2014.
Nevill et al., Integrated microfluidic cell culture and lysis on a chip, Lab on A Chip 7:1689-95 (2007).
Nishio N, et al. Armed Oncolytic Virus Enhances Immune Functions of Chimeric Antigen Receptor—Modified T Cells in Solid Tumors. Cancer Res. 74(18):5195-205. Sep. 15, 2014.
Parker LL, et al., gentleMACS™ Dissociation of melanoma tumors for the generation of tumor-infiltrating lymphocyte cultures foradoptive cell therapy. MACS: Milteyi Biotec. Copyright 2011.
Pule MA, et al. A Chimeric T Cell Antigen Receptor That Augments Cytokine Release and Supports Clonal Expansion of Primary Human T Cells. Molecular Therapeutics. 12(5):933-941. Nov. 2005, available online on Jun. 23, 2005.
Ritchie et al., "Reconstruction of Membrane Proteins in Phospholipid Bilayer Nandiscs," Methods Enzymol, 2009, 464:211-231.
Schena et al., Dependence of Immunoglobin Class Switch Recombinatino in B Cells on Vesicular Release of ATP and CD73 Ectonucleotidase Activity, Cell Reports, 3:1824-1831 (2013).
Schumacher et al., Neoantigens in cancer immunotherapy, Science 348:69-74 (2015).
Smith et al., Sorting Out Cell Sorting: Flow Cytometry, Magnetic Beads or Microchips?, downloaded from http://www.biocompare.com/Editorial-Articles/126327-Cell-Sorting, 2013.
Takahashi Y. et al. "High throughput cell sorting device using dielectrophoresis and fluid-induced shear force", Engineering in Medicine and Biology Society (EMBC), 2013 35th Annual International Conference of the IEEE, IEEE, Jul. 3, 2013 (Jul. 3, 2013), pp. 4466-4469.
The International Search Report and the Written Opinion of the International Searching Authority, PCT Application Serial No. PCT/US2017/013483 (dated Apr. 10, 2017), 17 pages.
Topfer et al., DAP12-Based Activating Chimeric Antigen Receptor for NK Cell Tumor Immunotherapy, J. Immunology 194:3201-3212 (2015).
Valley et al., Optoelectronic Tweezers as a Tool for Parallel Single-Cell Manipulation and Stimulation, IEEE Transactions on Biomedical Circuits and Systems 3(6):424-30 (2009).
Van Dongen, "EuroFlow antibody panels for standarized n-dimensional flow cytometric immunophenenotyping of normal, reactive and malignant leukocytes", Luekemia 2010; 24; 18 pages.
Vera J, et al., T lymphocytes redirected against the light chain of human immunoglobulin efficiently kill mature B lymphocyte-derived malignant cells. Blood. 108:3890-3897. 2006.
Watkins SK, et al. Video Article: Isolation of Immune Cells from Primary Tumors. Journal of Visualized Experiments. vol. 64:e3952. Jun. 2012. The video component of this article can be found at http://www.jove.com/video/3952/.
Zamo, "Application of Microfludic Technology to the BIOMED-2 Protocol for Detection of B-Cell Clonality", The Journal of Molecular Diagnostics, vol. 14, No. 1, Jan. 2012; 8 pages.
File History of U.S. Appl. No. 15/406,289, filed Jan. 13, 2017.
Armitage et al., "B-cell stimulation," Current Opin Immunol, 1995, 7:243-247.
Boeglin et al., "Toll-Like Receptor Agonists Synergize with CD40L to Induce Either Proliferation or Plasma Cell Differentiation of Mouse B Cells," PLoS One, 2001, 6(10):e25542, 10 pages.
Hartmann et al., "Rational design of new CpG oligonucleotides that combine B cell activation with high IFN-α induction In plasmacytoid dendritic cells," Eur. J. Immunol., 2003, 33:1633-1641.
Jakobsen et al., "Phage Display-Derived Human Monoclonal Antibodies Isolated by Binding to the Surface of Live Primary Breast Cancer Cells Recognize GRP78," Cancer Res, 2007, 67(19):9507-9517.
Krag et al., "Selection of Tumor-binding Ligands in Cancer Patients with Phase Display Libraries," Cancer Res, 2006, 66(15):7724-33.
Maletzki et al., "Ex-vivo Clonally Expanded B Lymphocytes Infiltrating Colorectal Carcinoma are of Mature Immunophenotype and Produce Functional IgG," PLoS One, 2012, 7(2): e32639, 7 pages.
Pavoni et al., "Tumor-infiltrating B lymphocytes as an efficient source of highly specific immunoglobulins recognizing tumor cells," BMC Biotechnology, 2007, 7(70):1-17.

(56) References Cited

OTHER PUBLICATIONS

Qiao et al., "Screening for antibodies against intact cancer cells with a naïve large phage antibody library," Intl J Mol Med, 2012, 29:37-46.
Shukla et al., "Intravenous Infusion of Phage-displayed Antibody Library in Human Cancer Patients: Enrichment and Cancer Specificity of Tumor-Homing Phage-Antibodies," Cancer Immunol Immunother., 2013, 62(8):1397-1410.
Office Action issued in corresponding Korean Application No. 10-2018-7023525, dated Sep. 26, 2022, 5 pages.
English translation of Office Action issued in corresponding Korean Application No. 10-2018-7023525, dated Sep. 26, 2022, 4 pages.

METHODS OF PRODUCING PATIENT-SPECIFIC ANTI-CANCER THERAPEUTICS AND METHODS OF TREATMENT THEREFOR

This application is a continuation of U.S. patent application Ser. No. 15/406,289, filed Jan. 13, 2017, which is a non-provisional application claiming the benefit under 35 U.S.C. 119(e) of U.S. Provisional Application No. 62/279,341, filed on Jan. 15, 2016; U.S. Provisional Application No. 62/411,690, filed on Oct. 23, 2016; and of U.S. Provisional Application No. 62/412,092, filed on Oct. 24, 2016, each of which disclosures is herein incorporated by reference in its entirety.

FIELD

Methods for isolating B cells that produce cancer-specific antibodies are provided, as well as methods of treatment using those antibodies and/or derivatives thereof.

BACKGROUND

Immunotherapy is the burgeoning field of using a patient's own immune system to help fight cancer. A variety of immunotherapy strategies have been evaluated, including stimulating the patient's own immune system to attack cancer cells or administering immune system components from an external source. For example, monoclonal antibodies designed to attack cancer cells in vivo have been administered alone or in genetically engineered constructs. In addition, CAR-T (chimeric antigen receptor T cell) therapy has been investigated. In this therapeutic approach, genetically engineered T cells express antibody-containing fusion proteins on their surface, which target the T cells to the cancer in question and allows for the T cells to kill the cancer cells. Because the CAR-T cells can become permanently engrafted in the patient's body, this approach seems particularly promising. These approaches, however, still require further refinement.

One of the key problems in monoclonal antibody therapy or CAR-T therapy is identifying or designing an antibody that will provide the maximum benefit to the patient in question, keeping in mind that the patient may have a very short window of time before the treatment can begin or before treatment success is required to prevent significant morbidity and mortality.

The present embodiments offer a solution to identifying antibodies that will provide the maximum benefit to the patient in question, minimizing the amount of time required for research investigation and allowing for treatment to begin as soon as possible.

SUMMARY

In accordance with the description, a method of preparing an antibody therapeutic comprises:
 a) providing a dissociated cell sample from at least one solid tumor sample obtained from a patient;
 b) loading the dissociated cell sample into a microfluidic device having at least one isolation region;
 c) moving at least one B cell from the dissociated cell sample into at least one isolation region in the microfluidic device, thereby obtaining at least one isolated B cell;
 d) identifying at least one isolated B cell that produces antibodies capable of binding to a cancer cell-associated antigen.

This method and others described herein provide the advantage of identifying B cells that, in some embodiments, the patient's own body has produced in order to target the type of cancer that the patient is suffering from. By using a microfluidic device to isolate these antibodies, a plurality of B cells can be tested in parallel in a relatively rapid assay format and specific B cells of interest can be identified, cultured, and sequenced (or used to produce a hybridoma). This enables investigators to produce patient-specific anti-cancer antibodies, which can be administered as monoclonal antibodies or fragments thereof, or genetically engineered constructs such as fusion proteins or CAR-T therapeutics, or used in methods of detection, etc.

Additional embodiments include methods of treating a patient having cancer comprising treating the patient with an antibody or fragment thereof produced by the methods herein. Cancer in a patient may also be labeled or detected using antibodies or fragments thereof conjugated to a detectable label. As compositions for treatments, engineered T cells comprising the antibodies or fragments thereof displayed on their surface may be provided, as well as engineered antibody constructs that comprise at least the heavy chain CDRs of the antibody identified herein, at least the heavy and light chain CDRs, at least the heavy chain variable region, or at least the heavy and light chain variable regions.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 5A is a bright field image of a portion of the microchannel device. FIGS. 5B and 5C are fluorescence images obtained using a Texas Red filter. In FIG. 5B, the image was obtained 5 minutes after the start of the antigen specificity assay described in Example 1. In FIG. 5C, the image was obtained 20 minutes after the start of the antigen specificity assay described in Example 1. The white arrows in FIG. 5C point to sequestration chambers that generated a positive signal in the assay.

DETAILED DESCRIPTION OF THE EMBODIMENTS

I. Definitions

Figure 1A:
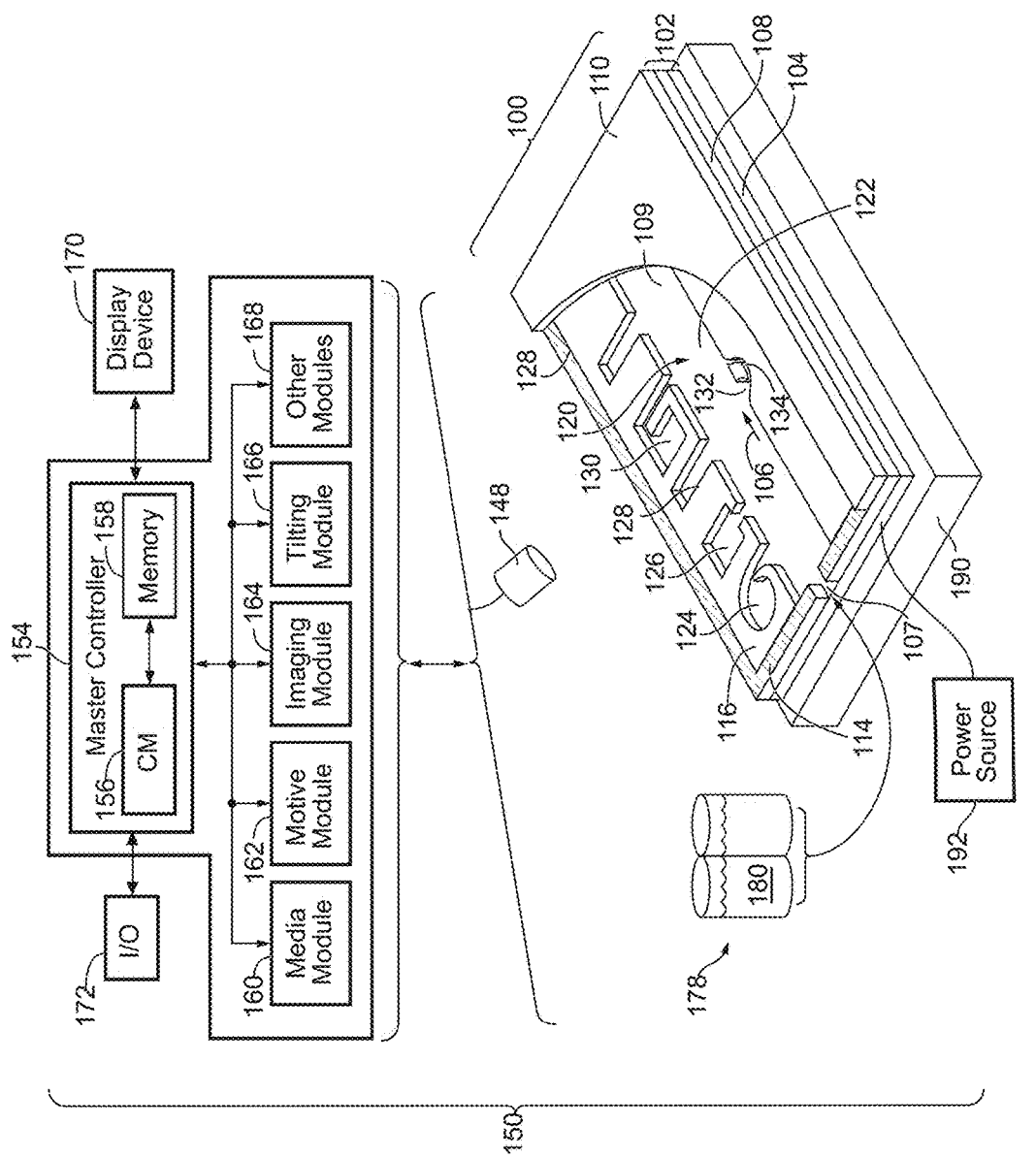
FIG. 1A illustrates an example of a microfluidic device and a system for use with the microfluidic device, including associated control equipment according to some embodiments.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least two ports configured to allow the fluid (and, optionally, micro-objects suspended in the fluid) to flow into and/or out of the microfluidic device. Typically, a microfluidic circuit of a microfluidic device will include at least one microfluidic channel and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 µL.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less. A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements is configured to hold a volume of fluid of about 20 nL to 200 nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to a flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 50,000 microns to about 500,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may include one or more sections having any of the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic sequestration chamber and a microfluidic channel, or a connection region and an isolation region of a microfluidic sequestration chamber.

As used herein, the term "constriction" refers generally to a narrowing of a width of a circuit element (or an interface between two circuit elements) in a microfluidic device. The constriction can be located, for example, at the interface between a microfluidic sequestration chamber and a microfluidic channel, or at the interface between an isolation region and a connection region of a microfluidic sequestration chamber.

As used herein, the term "transparent" refers to a material which allows visible light to pass through without substantially altering the light as is passes through.

As used herein, the term "micro-object" refers generally to any microscopic object that may be isolated and collected in accordance with the present invention. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells (e.g., embryos, oocytes, ova, sperm cells, cells dissociated from a tissue, eukaryotic cells, protist cells, animal cells, mammalian cells, human cells, immunological cells, hybridomas, cultured cells, cells from a cell line, cancer cells, infected cells, transfected and/or transformed cells, reporter cells, prokaryotic cells, and the like); biological organelles; vesicles, or complexes; synthetic vesicles; liposomes (e.g., synthetic or derived from membrane preparations); lipid nanorafts (as described in Ritchie et al. (2009) "Reconstitution of Membrane Proteins in Phospholipid Bilayer Nanodiscs," Methods Enzymol., 464: 211-231), and the like; or a combination of inanimate micro-objects and biological micro-objects (e.g., microbeads attached to cells, liposome-coated micro-beads, liposome-coated magnetic beads, or the like). Beads may further have other moieties/molecules covalently or non-covalently attached, such as fluorescent labels, proteins, small molecule signaling moieties, antigens, or chemical/biological species capable of use in an assay.

As used herein, the term "cell" refers to a biological cell, which can be a plant cell, an animal cell (e.g., a mammalian cell), a bacterial cell, a fungal cell, or the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. The term "clonal cells" refers to cells of the same clonal colony.

As used herein, "colony" of biological cells refers to 2 or more cells (e.g. 2-20, 4-40, 6-60, 8-80, 10-100, 20-200, 40-400, 60-600, 80-800, 100-1000, or greater than 1000 cells).

As used herein, the term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein: μm means micrometer, μm3 means cubic micrometer, pL means picoliter, nL means nanoliter, and μL (or uL) means microliter.

Section divisions in the specification are for ease of review only and do not limit any combination of elements discussed.

II. Method of Preparing an Antibody Therapeutic

An antibody therapeutic may be prepared using a method comprising the steps of:
 a) providing a dissociated cell sample from at least one solid tumor sample obtained from a patient;
 b) loading the dissociated cell sample into a microfluidic device having a flow region and at least one isolation region fluidically connected to the flow region;
 c) moving at least one B cell from the dissociated cell sample into at least one isolation region in the microfluidic device, thereby obtaining at least one isolated B cell; and
 d) identifying at least one isolated B cell that produces antibodies capable of binding to a cancer cell-associated antigen.

This method of identifying antibodies may be practiced in a variety of different modes, keeping in mind one potential goal of having a relationship between the B cells producing the antibodies and the cancer cells that are posing the problem for the patient for whom a therapeutic is desired. One particular method 400 is outlined in FIG. 4.

In certain instances, the method further comprises determining paired heavy chain and light chain variable domain antibody sequences from the identified B cell(s). For example, the sequencing may be performed after at least one B cell producing an antibody binding to the cancer cells is exported from the microfluidic device. In other instances, the method comprises generating a hybridoma from at least one isolated B cell. If the antibody sequence is determined, the method may also comprise generating an antibody therapeutic comprising some or all of the paired heavy chain and light chain variable domain sequences from the at least one identified B cell. For example, a method may comprise preparing an antibody or functional part thereof that comprises all six CDRs from the heavy and light chain variable domain sequences from the at least one identified B cell.

A. Preparation of the Dissociated Cell Sample

In certain instances, the methods include the step of obtaining a sample from a solid tumor. For example, as shown in step 410 of method 400 in FIG. 4. The solid tumor sample can be a tumor biopsy, such as a surgically resected biopsy or a fine needle aspirate (FNA). In some instances, the tumor has a tertiary lymphoid structure, which may comprise proliferating B cells and/or a B-cell follicle. The tumor may be breast cancer, genitourinary cancer, a cancer of the nervous system, intestinal cancer, lung cancer, melanoma, or another type of cancer. In some embodiments, the breast cancer may be a medullary breast cancer. In some embodiments, the genitourinary cancer may be a cancer originating in the urinary tract, such as in the kidneys (e.g., renal cell carcinoma), ureters, bladder, or urethra. In some embodiments, the genitourinary cancer may be a cancer of the male reproductive tract (e.g., testicular cancer, prostate cancer, or a cancer of the seminal vesicles, seminal ducts, or penis) or of the female reproductive tract (e.g., ovarian cancer, uterine cancer, cervical cancer, vaginal cancer, or a cancer of the fallopian tubes). In some embodiments, the cancer of the nervous system may be neuroblastoma. In some embodiments, the intestinal cancer may be colorectal cancer. In some embodiments, the lung cancer may be mesothelioma.

In some instances, a single tumor sample is obtained. In other instances, multiple tumor samples are obtained. In one instance, all tumor samples are from the same patient. For example, one tumor sample may be used from the patient (such as a single biopsy) or multiple tumor samples may be used from the same patient (such as multiple biopsies from the same tumor or from different tumors in the patient).

In other instances, tumor samples may be used from different patients. For example, the B cells can be from a first patient and cancer cells (e.g., cancer cells used as a source of cancer cell-associated antigen) are from a second patient. In some of these modes, the B cells are from the patient who desires treatment. In some of these modes the cancer cells are from a cancer cell line. If the samples are from different patients, some relationship between the B cells producing the antibodies and the cancer cell-associated antigen may also be preserved. For example, if the cancer cell-associated antigen is not from the cancer cells of the same patient, in some embodiments, they may be from the same type of cancer. In certain instances, cancer cells used in the microfluidic device or otherwise used to provide cancer-associated antigen exhibit one or more markers that are characteristic of the type of tumor that the patient is suffering from. For example, the cancer cells can have one or more such markers that are also present in the patient's tumor sample.

In certain instances, the methods include the step of processing the tumor sample to produce a dissociated cell sample. For example, as shown in step 420 of method 400 in FIG. 4. The dissociated cell sample may comprise at least one single cell that is dissociated from a tumor (e.g., tumor biopsy or FNA). In some instances, all of the cells are in single cell form. In other instances, some of the cells are not in single cell form, but remain in clumps of about 2, 3, 4, 5, 6, 7, 8, 9, 10 cells or more, yet other cells are in single cell form. A dissociated cell sample includes a cancer cell line grown in culture in dissociated form. Thus, the cells may either be actively dissociated (by obtaining at least one solid tumor sample and dissociating at least one single cell) or passively dissociated (by obtaining a sample that has been previously dissociated or grown in dissociated form).

The dissociation may be conducted in a number of ways. For example, the tumor sample may be dissociated using a collagenase plus DNase digestion. The tumor sample may also be dissociated using a cell dissociator instrument, such as the gentleMACS™ instrument from Miltenyi Biotec.

In some instances, the method further comprises performing a selection on the dissociated cell sample prior to loading, to isolate a fraction that has a greater percentage and/or concentration of B cells than the original dissociated sample. For example, as shown in step 430 of method 400 in FIG. 4. If desired, B cells may be selected from the dissociated cell sample using at least one marker, such as those chosen from CD19, CD20, IgM, IgD, CD38, CD27, CD138, PNA, and GL7. Alternatively, or in addition, a negative selection may be performed to remove non-B cells (e.g., using at least one marker that is not expressed on B cells). For example, the dissociated cell sample may be depleted of cancer cells (e.g., using a cancer-cell specific marker) and/or T cells (e.g., using a T cell-specific marker, such as CD3, CD4, CD8, etc.). In still other instances, the dissociated cell sample is loaded into the microfluidic device without being processed to enrich for B cells.

Regardless of whether the dissociated cell sample is processed to enrich for B cells, the dissociated cell sample is loaded into a microfluidic device. See, for example, step 440 of method 400 in FIG. 4. In some instances, a single dissociated cell sample may be loaded onto the microfluidic device. The single dissociated cell sample may comprise both B cells and other types of cells (e.g., cancer cells). In other instances, (i) separate fractions of a single dissociated cell sample or (ii) different dissociated cell samples (e.g., each fractionated separately and/or in a different manner), may be loaded at different times. In some instances, a dissociated cell sample may be processed to produce a fraction that has a greater percentage and/or concentration of cancer cells than the original sample. The cancer cell fraction may be the fraction that remains after selection of B cells, or vice versa.

If desired, the cancer cells may be selected from the dissociated cell sample using at least one marker characteristic of the cancer. In some instances, the cells may be separated using morphological differences. Cancer cells often display irregular cell size (e.g., larger cell size, or smaller cell cell), bigger nuclei, contain more DNA, or contain nuclear structural changes. In many cases, these differences can be discerned visually and/or by image analysis, which may be automated. To facilitate or enhance such analysis, the dissociated cell sample can be stained for nucleic acids (e.g., when stained with a nucleic acid-binding dye, cancer cells often stain brighter than normal cells) or for markers associated with the nuclear envelope, nucleoli, and/or nuclear matrix. Examples of such markers include lamins (e.g., A- or B-type lamins), nuclear membrane proteins (e.g., nuclear lamina-associated proteins, such as emerin), fibrillarin, nuclear pore proteins (NUPs, such as Nup153, Nup210, etc.), histone proteins, and nuclear matrix proteins (e.g., p84)), any of which can highlight differences in nuclear structure.

Aside from morphological differences, a variety of markers are known in the art as being useful for identifying certain types of cancer cells, including but not limited to:

For breast cancer, CD44, HLA-DR, Ki-67 (or MK167), aldehyde dehydrogenase 1 (ALDH1), and ganglioside GD2 tend to be present and/or elevated in cancer cells, while estrogen receptor (ER), progesterone receptor (PR), human epidermal growth factor receptor 2 (HER2), and CD24 tend to be absent or reduced in cancer calls; ER−/PR−/HER2−/HLA-DR+ can be used to identify medullary breast cancer; and CD44$^{hi}$/CD24$^{lo}$/ALDH1$^{hi}$ or CD44$^{hi}$/CD24$^{lo}$/GD2$^{hi}$ can be used to identify breast cancer stem cells.

For renal cancer, C-reactive protein, aquaporin-1 (AQP1), adipophilin (ADFP), insulin-like growth factor II mRNA binding protein 3 (IGF2BP3 or IMP3), B7-H1 (or PD-L1), and Ki-67 (MK167) tend to be present and/or elevated in cancer cells.

For bladder cancer, nuclear mitotic apparatus protein (NMP22), bladder tumor antigen (BTA), and fibrin/fibrinogen degradation products tend to be present and/or elevated in cancer cells, while adipocyte fatty acid binding protein (A-FABP), glutathione S-transferase mu (GST-μ), prostaglandin dehydrogenase (PGDH), and keratin 13 tend to be absent or reduced relative to normal cells; at the genetic level, the p16 tumor suppressor gene or the 9p21 locus may be deleted in cancer cells.

For urothelial cancer, complement factor H-related protein (CFHrp) may exhibit increased levels and/or secretion in cancer cells; at the nuclear level, telomerase reverse transcriptase (TERT) tends to exhibit increased mRNA expression in cancer cells.

For endometrial cancer, cancer antigen 15-3 (CA15-3), cancer antigen 125 (CA125), cancer antigen 19.9 (CA19.9), cancer antigen 72.4 (CA72.4), and carcinoembryonic antigen (CEA) tend to be present and/or elevated in cancer cells.

For ovarian cancer, tumor-associated trypsin inhibitor (TATI), cancer antigen 125 (CA125), Claudin5, human epidydmis protein 4 (HE4), carcinoembryonic antigen (CEA), VCAM-1, and miR-181a tend to be present and/or elevated in cancer cells; TATI, CA125, and Claudin 5 have been used in combination to diagnose ovarian cancer, as have HE4 and CA125, optionally in conjunction with CEA and VCAM-1; STAT1 can be used to distinguish between ovarian cancers that are responsive to chemotherapy and those that are not.

For cervical cancer, human papilloma virus (HPV) (e.g., types 16, 18, 31, 33, 35, 39, 45, 51, 52, 56, 58, 59, 68, 6, 11, 42, 43, and 44), p16$^{INK4a}$, and insulin-like growth factor II mRNA binding protein 3 (IGF2BP3 or IMP3) tend to be present and/or elevated in cancer cells.

For prostate cancer, prostate specific antigen (PSA), sarcosine (a metabolite), prostate cancer gene 3 (PCA3), and TMPRSS2:ERG fusion product tend to be present and/or elevated in cancer cells, while prostatic acid phosphatase, fibrinogen a chain precursor, collagen α-1 (III), collagen α-1 (I), psoriasis susceptibility 1 candidate gene 2 protein, hepatocellular carcinoma associated protein TB6, histone H2BB, osteopontin, polymeric Ig receptor, Na/K-transporting ATPase γ, transmembrane secretory component, and semenogelin 1 tend to be absent or reduced relative to normal cells.

For neuroblastoma, increased levels and/or secretion of vanillylmandelic acid (VMA), homovanillic acid (HVA), and ferritin are associated with cancer cells, and neuron-specific enolase (NSE), lactate dehydrogenase (LDH), and ganglioside GD2 tend to be present and/or elevated in cancer cells; at the genomic level, deletions in parts of chromosomes 1p and 11q and duplication of a part of 17q are associated with cancer cells.

For colorectal cancer, carcinoembryonic antigen (CEA), cancer antigen 19-9 (CA19-9), colon-cancer-specific antigen 3 (CCSA-3), colon-cancer-specific antigen 4 (CCSA-4), and B-Raf mutation V600E tend to be present and/or elevated in cancer cells; at the genetic level, colorectal cancer cells exhibit microsatellite instability and various K-Ras mutations.

For small cell lung carcinoma, ganglioside GD2 tends to be present and/or elevated in cancer cells; for non-small cell lung carcinoma, B-Raf mutation V600E tends to be present in cancer cells; for mesothelioma, calretinin, cytokeratin 5/6, and WT1 tend to be present and/or elevated in cancer cells, while carcinoembryonic antigen (CEA), epithelial cell adhesion molecule (Ep-CAM)(e.g., as detected by the MOC-31 or Ber-EP4 antibodies), Lewis Y blood group (e.g., as detected by the BG-8 antibody), and the tumor associated glycoprotein detected by the B72.3 antibody tend to be absent or reduced; and, conversely, for pulmonary adenocarcinoma, CEA, Ep-CAM (e.g., as detected by the MOC-31 or Ber-EP4 antibodies), Lewis Y blood group (e.g., as detected by the BG-8 antibody), and the tumor associated glycoprotein detected by the B72.3 antibody tend to be present and/or elevated in cancer cells, while calretinin, cytokeratin 5/6, and WT1 tend to be absent or reduced.

For melanoma, the human endogenous retrovirus (HERV-K), ganglioside GD2, B-Raf mutation V600E, Hsp90, regulator of G-protein signaling 1 (RGS1), Osteopontin, human epidermal growth factor receptor 3 (HER3), nuclear receptor coactivator 3 (NCOA3), and minichromosome maintenance complex components 4 and 6 (MCM4 and MCM6, respectively) tend to be present and/or elevated in cancer cells, while inhibitor or growth proteins 3 and 4 (ING3 and ING4, respectively) tend to be absent or reduced relative to normal cells.

In some instances, the cancer cells may be selected from the dissociated cell sample using at least two markers characteristic of the cancer. For example, the two or more markers can include a morphological marker, at least one positive marker (e.g., a marker which is present and/or elevated in the cancer cells), and/or at least one negative marker (e.g., a marker which is absent or reduced relative to normal cells), or any combination thereof. In certain modes, the B cells (e.g., memory B cells, plasma B cells, or the like, and combinations thereof) and/or cancer cells may be selected from the dissociated cell sample by FACS. Alternatively, or in addition, the B cells (e.g., memory B cells, plasma B cells, or the like, and combinations thereof) and/or cancer cells may also be selected from the dissociated sample by using magnetic bead-based sorting. The selection can enrich the sample for B cells that express CD27 (or some other memory B cell marker) or for B cells that express CD138 (or some other plasma cell marker). The selection can be positive (e.g., based on a B cell-specific or a cancer cell-specific marker). Alternatively, the selection can be negative. For example, non-B cell cell types can be depleted from the dissociated cell sample using techniques that are well known in the art, such as treating the sample with the DYNABEADS™ Untouched Human B Cells reagent (Thermo Fisher), the B Cell Isolation Kit (Miltenyi), the RosetteSep Human B Cell Enrichment Cocktail (Stem Cell Technologies), or the like. As another example, the selection can deplete the sample of B cells expressing IgM antibodies, IgA antibodies, IgD antibodies, IgG antibodies, or any combination thereof. Alternatively, or in addition, the B cells and/or cancer cells may be selected using a microfluidic device, as discussed further below.

B. Loading and Moving B Cells into and within the Microfluidic Device

Figure 4:
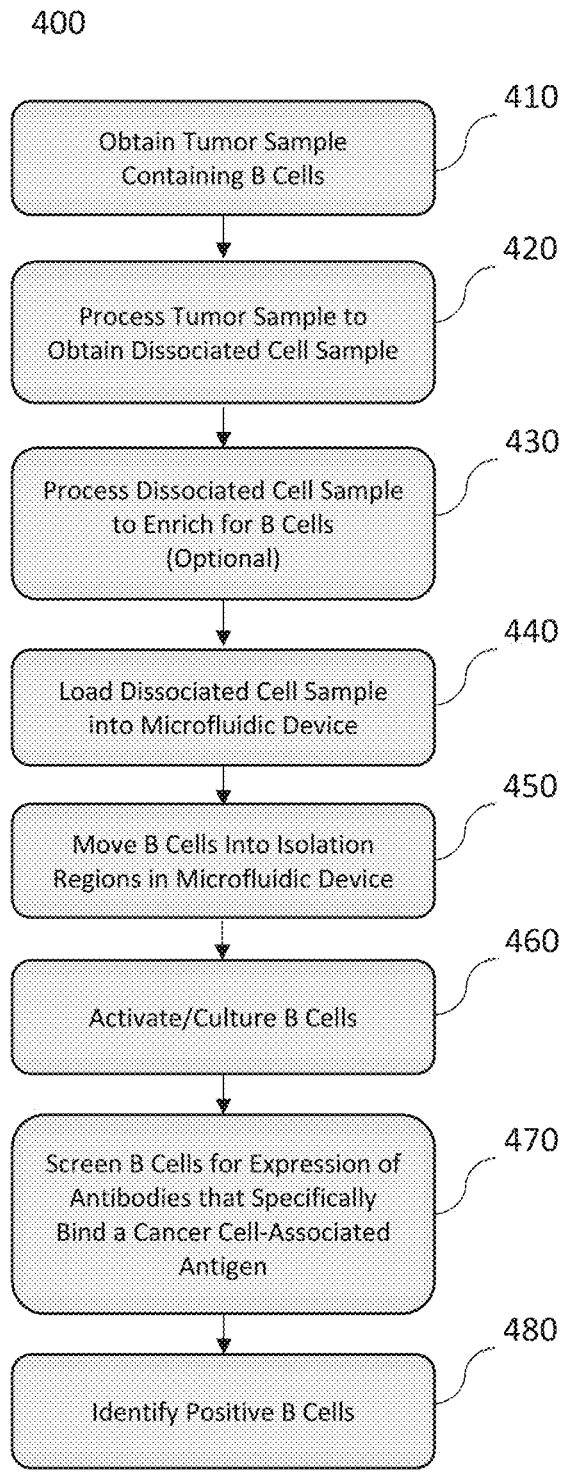
FIG. 4 illustrates steps in an exemplary workflow for identifying a B cell lymphocyte expressing an antibody that specifically binds to a cancer cell-associated antigen according to some embodiments.

The dissociated cell sample (optionally fractionated as discussed above) can be loaded into the microfluidic device by flowing the cells of the sample through an inlet in the device and into the flow region. For example, step 440 of method 400 shown in FIG. 4 provides for loading the dissociated cell sample into the microfluidic device. In some embodiments, the flow region includes a flow channel (or microfluidic channel), and loading the dissociated cell sample includes flowing the cells into the flow channel.

Once the dissociated cell sample is loaded into the flow region (or flow channel) of the microfluidic device, B cells in the sample can be moved into isolation regions of the microfluidic device. For example, as illustrated in step 450 of method 400 (FIG. 4), B cells can be moved from the flow region (or flow channel) into one or more isolation regions, which may be located within isolation chambers that are fluidically connected with and open off of the flow region (or flow channel). The B cell can be, for example, a $CD27^+$ B cell or a $CD138^+$ B cell. In some embodiments, the B cell is a memory B cell. In other embodiments, the B cell is a plasma cell. The movement of the B cells may be accomplished by a variety of means, as discussed generally herein, including using gravity (such as by tipping the microfluidic device), inducing localized fluid flow (such as by depressing or pulling a deformable surface of the microfluidic device located adjacent or proximal to the isolation region), applying dielectrophoretic (DEP) force (such as by optoelectronic tweezers (OET)), or any combination thereof.

In some instances, prior to loading the dissociated cell sample, the method further comprises labeling B cells in the dissociated cell sample with at least one detectable marker. The marker may be a B cell-specific marker, such as any one of the B cell markers disclosed herein (e.g., CD19, CD20, IgM, IgD, CD38, CD27, CD138, PNA, GL7, and the like). The marker may aid in selecting B cells for movement based on the detection of the detectable marker, such as in the embodiment where the B cell is moved by applying DEP force. Alternatively, the detectable marker can bind to a non-B cell marker, such as a T cell marker or a cancer cell-associated marker. In such instances, B cells can be selected for movement based on their lack of the detectable marker.

The B cells loaded into the isolation region(s) of the microfluidic device can include a mixture of differ B cell types, such as memory B cells, plasma cells, and the like. In some embodiments, it may be desirable to select plasma cells for movement into the isolation regions. In some embodiments, it may be desirable to select B cell that express an IgG-type antibody for movement into the isolation regions.

In some instances, only one B cell is moved into each isolation region, whether all of the isolation regions are loaded or not. In other instances, the B cells can be initially pooled into one or more isolation regions, and later separated into individual isolation regions (i.e., one B cell per isolation region). The latter embodiments allow for greater throughput when screening the B cells for production of antibodies that bind to the cancer cells. Placement of only one B cell in each isolation region allows for clonal expansion of the B cell, which can facilitate the identification of paired heavy chain and light chain variable domain sequences.

In certain embodiments, the B cells are loaded into the microfluidic device and moved into the isolation regions before the cancer cell-associated antigen is loaded into the microfluidic device. In other embodiments, the B cells are loaded into the microfluidic device and moved into the isolation regions after the cancer cell-associated antigen have been loaded into the microfluidic device and moved into the isolation regions. In still other embodiments, the B cells and the cancer cell-associated antigen are loaded into the microfluidic device at the same time (e.g., as part of a dissociated cell sample that includes both B cells and cancer cells). In some embodiments, once the B cells are loaded into the isolation regions they remain there until after at least one B cell produces antibodies capable of binding to the cancer cell-associated antigen has been identified.

C. Contacting B Cells that Produce Antibodies with Cancer Cell-Associated Antigens The disclosed methods include the step of detecting whether a B cell is expressing an antibody that specifically binds to a cancer cell-associated antigen. See, for example, step 470 of method 400 in FIG. 4. To detect such expression, the expressed antibody must be allowed to interact with the cancer cell-associated antigen.

The cancer cell-associated antigen can be simple or complex; the antigen can be an epitope on a protein, a carbohydrate group or chain, a biological or chemical agent other than a protein or carbohydrate, or any combination thereof; the epitope may be linear or conformational. The cancer cell-associated antigen can be an antigen that uniquely identifies cancer cells (e.g., one or more particular types of cancer cells) or is upregulated on cancer cells as compared to its expression on normal cells. Typically, the cancer cell-associated antigen is present on the surface of the cancer cell, thus ensuring that it can be recognized by an antibody. The antigen can be associated with any type of cancer cell, including any type of cancer cell that can be found in a tumor known in the art or described herein. In particular, the antigen can be associated with lung cancer, breast cancer, melanoma, and the like. As used herein, the term "associated with a cancer cells," when used in reference to an antigen, means that the antigen is produced directly by the cancer cell or results from an interaction between the cancer cell and normal cells.

Detecting whether a B cell expressed antibody specifically binds to a cancer cell-associated antigen can be performed in a microfluidic device described herein. In particular, the microfluidic device can include an enclosure having a flow region (e.g., a microfluidic channel) and a sequestration chamber. The sequestration chamber can include an isolation region and a connection region, the connection region providing a fluidic connection between the isolation region and the flow region. The sequestration chamber can have a volume of about 0.5 nL to about 5.0 nl, or any range therein (e.g., about 0.5 nl to about 1.0 nl, about 0.5 nl to about 1.5 nl, about 0.5 nl to about 2.0 nl, about 1.0 nl to about 1.5 nl, about 1.0 nl to about 2.0 nl, about 1.0 nl to about 2.5 nl, about 1.5 nl to about 2.0 nl, about 1.5 nl to about 2.5 nl, about 1.5 nl to about 3.0 nl, about 2.0 nl to about 2.5 nl, about 2.0 nl to about 3.0 nl, about 2.0 nl to about 3.5 nl, about 2.5 nl to about 3.0 nl, about 2.5 nl to about 3.5 nl, about 2.5 nl to about 4.0 nl, about 3.0 nl to about 3.5 nl, about 3.0 nl to about 4.0 nl, about 3.0 nl to about 4.5 nl, about 3.5 nl to about 4.0 nl, about 3.5 nl to about 4.5 nl, about 3.5 nl to about 5.0 nl, about 4.0 nl to about 4.5 nl, about 4.0 nl to about 5.0 nl, about 4.5 nl to about 5.0 nl, or any range defined by one of the foregoing endpoints). The connection region can have a width $W_{con}$ as generally described herein (e.g., about 20 microns to about 100 microns, or about 30 microns to about 60 microns). The isolation region can likewise have a width $W_{iso}$ that is generally as described herein (e.g., the isolation region can have a width $W_{iso}$ that is greater than the width $W_{con}$ of the connection region). In certain embodiments, the isolation region has a width $W_{iso}$ that is about 50 microns to about 250 microns.

The flow region, the sequestration chamber, and/or the isolation region of the sequestration chamber can include at least one surface coated with a coating material that promotes the viability of the antibody-expressing B cell (e.g., a memory B cell or a plasma cell). As used in this context, "promote the viability" means that the viability of the B cell is better on the coated surface as compared to an equivalent surface that is non-coated. In certain embodiments, the flow region, the sequestration chamber, and/or the isolation region has a plurality of surfaces each coated with a coating material that promotes the viability of the B cell. The coating material can be any suitable coating material known in the art and/or described herein. The coating material can, for example, comprise hydrophilic molecules. The hydrophilic molecules can be selected from the group of polymers comprising polyethylene glycol (PEG), polymers comprising carbohydrate groups, polymers comprising amino acids, and combinations thereof.

The flow region, the sequestration chamber, and or the isolation region of the sequestration chamber can include at least one conditioned surface that promotes the viability of the B cell (e.g., a memory B cell or a plasma cell). As used in this context, "promote the viability" means that the viability of the B cell is better on the conditioned surface as compared to an equivalent surface that is not conditioned. In certain embodiments, the flow region, the sequestration chamber, and/or the isolation region has a plurality of conditioned surfaces each of which is capable of promoting the viability of the B cell. The conditioned surface(s) can comprise covalently linked molecules. The covalently linked molecules can be any suitable molecules known in the art and/or disclosed herein, including, for example, covalently linked hydrophilic molecules. The hydrophilic molecules can be selected from the group of polymers comprising polyethylene glycol (PEG), polymers comprising carbohydrate groups, polymers comprising amino acids, and combinations thereof. The hydrophilic molecules can form a layer of covalently linked hydrophilic molecules, as described herein.

Detecting a B cell expressing an antibody that specifically binds to a cancer cell-associated antigen can include introducing the cancer cell-associated antigen into the microfluidic device such that the antigen becomes located proximal to the B cell(s). Introducing the cancer cell-associated antigen into the microfluidic device can include, for example, flowing a fluidic medium that contains the cancer cell-associated antigen into the flow region of the microfluidic device and stopping the flow of the fluidic medium when the cancer cell-associated antigen is located proximal to the B cell(s). A location "proximal" to the B cell can be within 1 millimeter (mm) of the B cell (e.g., within 750 microns, within 600 microns, within 500 microns, within 400 microns, within 300 microns, within 200 microns, within 100 microns, or within 50 microns of the B cell).

The cancer cell-associated antigen can be provided as part of a micro-object, which may be any suitable micro-object known in the art and/or described herein (e.g., a cell, a liposome, a lipid nanoraft, or a bead). Thus, introducing the cancer cell-associated antigen into the microfluidic device can include positioning such a micro-object adjacent to or within the connection region of the sequestration chamber in which the B cell is located. Alternatively, introducing the cancer cell-associated antigen can include moving such a micro-object into the isolation region of the sequestration chamber in which the B call is located.

The micro-object can comprise antigen that has been fractionated from cancer cells, such as membrane-associated antigens found in a cancer cell membrane preparation. Such isolated membrane-associated antigens may be conjugated to beads to produce the micro-objects used in the disclosed methods. Alternatively, the micro-object can comprise a substantially pure antigen (e.g., a purified protein). Methods of conjugating antigenic molecules, such as purified proteins, cell membrane preparations, and the like, to beads are known in the art and/or are described in the Examples herein. Likewise, methods of isolating antigens from cancer cells are known in the art (see, e.g., Bachleitner-Hoffmann et al. (2002), J. Clin. Endocrin. & Metab. 87(3): 1098-1104; and He et al. (2016), Oncology Letters 12:1101-06). Thus, the isolation of cancer cell-associated antigens could be performed by a variety of methods known in the art. In other embodiments, the micro-object can be a cell, such as a cancer cell (e.g., isolated from the patient's sample) or a cell of a cancer cell line.

As indicated above, the micro-objects (e.g., cancer cells or antigen-conjugated beads) can be loaded into the microfluidic device (for the purpose of detecting antibody binding) by flowing the micro-objects through an inlet in the device and into the flow region. In some embodiments, the flow region includes a flow channel, and loading the micro-objects includes flowing the micro-objects into the flow channel.

In some embodiments, the micro-objects are loaded into the flow region (or flow channel) of the microfluidic device and remain in the flow region (or flow channel) until exported from the microfluidic device. In some embodiments, the micro-objects do not enter the isolation regions. In some embodiments, the micro-objects dip into the connection regions of isolation chambers in addition to residing in the flow region (or flow channel). In any of these embodiments, the micro-objects (e.g., cancer cells or antigen-conjugated beads) can be loaded into the flow region (or flow channel) at a concentration of at least about $1\times10^7$, $2.5\times10^7$, $5\times10^7$, $7.5\times10^7$, or $1\times10^8$ micro-objects/ml.

In some embodiments, the micro-objects are moved into at least one isolation region in the microfluidic device. As with the B cells, movement of the micro-objects (e.g., cancer cells or antigen-conjugated beads) can be accomplished by a variety of means, including using gravity (such as by tipping the microfluidic device), inducing localized fluid flow (such as by depressing or pulling a deformable surface of the microfluidic device located adjacent or proximal to the isolation region), applying dielectrophoretic (DEP) force (such as by optoelectronic tweezers (OET)), or any combination thereof. In such embodiments, one or more (e.g., only 1, about 2, 3, 4, 5, 6, 7, 8, 9, 10, or more, or from about 1 to 20, 1 to 10, 1 to 5, 1 to 3, 1 to 2) micro-objects can be moved into individual isolation regions in the microfluidic device, thereby obtaining at least one isolation region having an isolated micro-object or a group of isolated micro-objects. The isolated micro-object(s) and the B cell(s) may be placed in the same isolation region(s). Alternatively, the isolated micro-object(s) and the B cell(s) may be placed in different isolation regions (such as in adjacent isolation regions).

Irrespective of the desired location for the micro-objects in the microfluidic device, micro-objects that are cancer cells may be labeled with one or more detectable markers prior to loading the cancer cells into the microfluidic device. If the desired mode includes moving at least one cancer cell into at least one isolation region, the detectable marker(s) may be used to select at least one cancer cell for movement. Alternatively, or in addition, morphological assessments of the cell size, cell shape, nuclear size, or nuclear structure may be used to select at least one cancer cell for movement. Cancer cells may also be chosen by the absence of a cellular marker, optionally in combination with morphological assessments.

In certain embodiments, the cancer cells originate from a dissociated cell sample obtained from one or more solid tumor samples taken from the patient, and thus are the patient's own cancer cells. As discussed above, the cancer cells can be selected (or fractionated) from the dissociated cell sample and/or the cancer cells can be loaded into the microfluidic device as part of the same dissociated cell sample that contains the B cells. In certain embodiments, the cancer cells are cultured and/or cloned prior to assaying the B cells for production of antibodies capable of binding to the cancer cells. Such culturing and/or cloning can be performed within the microfluidic device or prior to loading the cancer cells into the microfluidic device (e.g., using conventional techniques for selecting, culturing, and/or cloning cancer cells from a tumor sample). Regardless, the cancer cells can be selected, cultured, and/or cloned to a concentration of at least about $1\times10^7$, $2.5\times10^7$, $5\times10^7$, $7.5\times10^7$, or $1\times10^8$ cells/ml.

As is well known in the art, a population of cancer cells derived from a tumor can be relatively heterogeneous with respect to the morphological and genetic characteristics of individual cells that make up the population. For example, the population may contain cancer stem cells (which may divide slowly) and more differentiated cancer cells (which may divide more rapidly and may contain differing subset of pro-cancer mutations). Marker-based selection and/or cloning of cancer cells can be used to provide more homogeneous populations of cells. Accordingly, in certain embodiments, in some embodiments, a plurality of heterogeneous cancer cells may be loaded onto the microfluidic device. Alternatively, individual cancer cells may be selected and cloned before loading onto the microfluidic device. Thus, in other embodiments, a substantially homogeneous population of cancer cells can be loaded into the microfluidic device and used to identify B cells that produce antibodies capable of binding to the cancer cells. The substantially homogeneous population can be a cancer cell line derived from the patient providing the at least one tumor or from a different patient.

In still other embodiments, providing the cancer cell-associate antigen can involve flowing a solution comprising soluble antigen through the flow region of the microfluidic device and allowing the soluble antigen to diffuse into the sequestration chamber in which the B cell is located. Such soluble antigen can be covalently bound to a detectable label (e.g., a fluorescent label).

D. Detection of Binding and Processing of B Cells

Binding of antibodies produced by the B cells to the cancer cell-associated antigen may be detected in a variety of ways. For example, when cancer cells are introduced into the microfluidic device, cell clumping may be detected, such as may occur in an agglutination assay. Alternatively, a secondary antibody, such as an anti-human antibody conjugated to a label (e.g., a fluorescent label), may be added in order to label micro-objects (e.g., cancer cells or antigen-conjugated beads) that have antibody bound to them. Thus, in some embodiments, the methods further comprise providing a labeled antibody-binding agent prior to or concurrently with the cancer cell-associated antigen. In such embodiments, monitoring of binding of the antigen antibody expressed by a B cell can involve detecting indirect binding of the labeled antibody-binding agent to the cancer cell-associated antigen. The labeled antibody-binding agent can be a labeled anti-IgG antibody, which may be fluorescently labeled. In certain embodiments, the labeled antibody-binding agent is provided in a mixture with the cancer cell-assoiciated antigen. In other embodiments, the labeled antibody-binding agent is provided after providing the cancer cell-associated antigen.

In certain embodiments, the methods can further comprise identifying at least one antibody expressing B cell (e.g., plasma cell or memory B cell) as expressing an antibody that specifically binds to the cancer cell-associated antigen. As discussed in more detail below, the microfluidic device may comprise an imaging device that allows for visualization of the signal (e.g., cancer cell clumping or accumulation of label at the surface of the micro-objects). For example, the imaging device can periodically image the microfluidic device and any increases in such signal over time can be detected. The images can be obtain, for example, every few seconds (e.g., every 5, 10, 15, 20, 25, 30, 35, 40, 45, 50, 55, 60 seconds, or more) or every few minutes (e.g., every 2, 3, 4, 5, 6, 7, 8, 9, 10 minutes, or more). In some embodiments, a plurality of images can be overlaid on top of one another, thereby creating a "summed" image which has the general effect of averaging out background signal and creating better contrast between real signal and background signal. The detection of signal can be manual, such as occurs when a person reviews the images, or automated (e.g., using appropriate image analysis software).

Once binding has been detected between cancer cell-associated antigen and the antibodies produced by the B cells, B cells producing such antibodies can be identified and their positions (e.g., the isolation regions or isolation chambers in which they are located) can be noted and/or recorded. See, for example, step 480 in method 400 of FIG. 4. Optionally, the flow region (or flow channel) may be flushed once antibody binding to cancer cells has been detected. Such flushing may occur before or after the identification of B cells producing antibodies that bind to the cancer cell-associated antigen (e.g., cancer cells or antigen-conjugated beads). As another optional step, the B cells that did not produce antibodies capable of binding the cancer cell-associated antigen may be discarded from the microfluidic device.

In certain embodiments, B cells identified as producing antibodies that bind to the cancer cell-associated antigen can be exported from the microfluidic device. For example, in order to isolate B cells for either sequencing (e.g., of antibody heavy and light chain variable regions) or preparation of a hybridoma, the B cells producing antibodies that bind to the cancer cells may be exported from the microfluidic device. In some instances, each cell or population of cloned cells is exported individually.

E. Stimulation of B Cell Activation

In any of the foregoing embodiments, B cells that have been moved into isolation regions in the microfluidic device can be incubated under conditions conducive to the production of antibodies. In some instances, those antibodies can diffuse through medium in the microfluidic device to the location of the cancer cell-associated antigen (whether comprised by a cancer cell or antigen-conjugated bead, or in solution; and whether in the same isolation region, the main flow channel, or in an adjacent isolation region). In the instance of adjacent isolation regions, in some microfluidic devices there exist small gaps in a thin wall between two adjacent isolation regions, allowing the antibodies to diffuse directly from one isolation region into another and without necessarily needing to enter the main flow channel to diffuse into an adjacent isolation region. Such small gaps allow for diffusion of antibodies but do not allow for either the cancer cells or the B cells to leave the isolation regions.

In some instances, the detection of B cells that express an antibody that specifically binds to a cancer cell-associated antigen can include the step of contacting a B cell with a stimulating agent that stimulates B cell activation. See, for example, step 460 in method 400 of FIG. 4. The stimulating agent can be a CD40 agonist, such as CD40L, a derivative thereof, or an anti-CD40 antibody. Thus, the stimulating agent can comprise, consist essentially of, or consist of CD40L+ feeder cells. The CD40L+ feeder cells can be T cells (e.g., Jurkat D1.1 cells), or a derivative thereof. Alternatively, the feeder cells can be a cell line (e.g., NIH-3T3 cells) transfected/transformed with a CD40L-expressing construct. The stimulating agent further comprises a toll-like receptor (TLR) agonist (e.g., a TLR9 agonist). The TLR agonist can be, for example, a CpG oligonucleotide (e.g., CpG2006). The CpG oligonucleotide can be used at a concentration of about 1 microgram/mL to about 20 micrograms/mL (e.g., about 1.5 to about 15 micrograms/mL, about 2.0 to about 10 micrograms/mL, or about 2.5 to about 5.0 micrograms/mL). The B cell can be contacted (e.g., substantially continuously, or periodically/intermittently) with the stimulating agent for a period of one to ten days (e.g., two to eight days, three to seven days, or four to six days).

Detecting a B cell expressing an antibody that specifically binds to a cancer cell-associated antigen can further include the step of providing the B cell with culture medium comprises one or more growth-inducing agents that promote B cell expansion. The one or more growth-inducing agents can include at least one agent selected from the group of IL-2, IL-4, IL-6, IL-10, IL-21, and BAFF. The IL-2 and/or IL-4 can be provided at a concentration of about 10 ng/mL to about 1 microgram/mL. The IL-6, IL-10, and/or IL-21 can be provided at a concentration of about 10 ng/mL to about 100 ng/mL. The BAFF can be provided at a concentration of about 10 ng/mL to about 50 ng/mL. In certain embodiments, the culture medium is provided to the B cell for a period of one to ten days (e.g., two to eight days, three to seven days, or four to six days). The culture medium can comprise the stimulating agent (e.g., CD40 agonist and/or TLR agonist). Thus, for example, providing the culture medium to the B cell can be performed at the same time as contacting the B cell with the activating agent. In certain embodiments, the steps of contacting the B cell lymphocyte with a stimulating agent and providing culture medium to the B cell lymphocyte are performed at overlapping times (e.g., over a substantially coextensive period of time). Additionally, as another optional step, the B cells may be cultured into clonal populations in the microfluidic device. Such culturing may occur, for example, for about 2 to 3 days and/or to a cell count of about 8 to 20 cells.

III. Microfluidic Devices

A. Microfluidic Device Terms

In some embodiments, a microfluidic device can comprise "swept" regions and "unswept" regions. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region.

The capability of biological micro-objects (e.g., biological cells) to produce specific biological materials (e.g., proteins, such as antibodies) can be assayed in such a microfluidic device. For example, sample material comprising biological micro-objects (such as a B cell) to be assayed for production of an analyte of interest (such as an antibody) can be loaded into a swept region of the microfluidic device. Ones of the biological micro-objects can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

B. System Including a Microfluidic Device

FIG. 1A illustrates an example of a microfluidic device 100 and a system 150 which can be used for isolating and screening tumor-derived B cells in vitro. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1A, suitable microfluidic devices can include a plurality (e.g., 2 or 3) of such microfluidic circuits. Regardless, the microfluidic device 100 can be configured to be a nanofluidic device. As illustrated in FIG. 1A, the microfluidic circuit 120 may include a plurality of microfluidic sequestration chambers 124, 126, 128, and 130, where each sequestration chamber has one or more openings in fluidic communication with flow path 106. In some embodiments of the device of FIG. 1A, the sequestration chambers have only a single opening in fluidic communication with the flow path 106. As discussed further below, the microfluidic sequestration chambers comprise various features and structures that have been optimized for retaining micro-objects in the microfluidic device, such as microfluidic device 100, even when a medium 180 is flowing through the flow path 106.

Before turning to the foregoing, however, a brief description of microfluidic device 100 and system 150 is provided.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers, pens, traps, and the like.

In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration chambers 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS).

Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light.

The cover 110 may also include at least one material that is gas permeable (e.g., PDMS or PPS).

FIG. 1A also shows a system 150 for operating and controlling microfluidic devices, such as microfluidic device 100. System 150 includes an electrical power source 192, an imaging device (incorporated within imaging module 164, where device 194 is not illustrated in FIG. 1A, per se), and a tilting device 190 (part of tilting module 166, where device 190 is not illustrated in FIG. 1A).

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device (part of imaging module 164, discussed below) can comprise a device, such as a digital camera, for capturing images inside microfluidic circuit 120. In some instances, the imaging device further comprises a detector having a fast frame rate and/or high sensitivity (e.g. for low light applications). The imaging device can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3B, the imaging device may further include a microscope (or an optical train), which may or may not include an eyepiece.

System 150 further comprises a tilting device 190 (part of tilting module 166, discussed below) configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35° 40°, 45° 50°, 55° 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration chambers. The term "above" as used herein denotes that the flow path 106 is positioned higher than the one or more sequestration chambers on a vertical axis defined by the force of gravity (i.e. an object in a sequestration chamber above a flow path 106 would have a higher gravitational potential energy than an object in the flow path). The term "below" as used herein denotes that the flow path 106 is positioned lower than the one or more sequestration chambers on a vertical axis defined by the force of gravity (i.e. an object in a sequestration chamber below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration chambers without being located directly above or below the sequestration chambers. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 1B and 1C, the enclosure 102 can comprise a dielectrophoresis (DEP), optoelectronic tweezers (OET) and/or opto-electrowetting (OEW) configuration (not shown in FIG. 1A), and the motive module 162 can control the activation of electrodes and/or transistors (e.g., phototransistors) to select and move micro-objects (not shown) and/or droplets of medium (not shown) in the flow path 106 and/or sequestration chambers 124, 126, 128, 130.

The imaging module 164 can control the imaging device. For example, the imaging module 164 can receive and process image data from the imaging device. Image data from the imaging device can comprise any type of information captured by the imaging device (e.g., the presence or absence of micro-objects, droplets of medium, accumulation of label, such as fluorescent label, etc.). Using the information captured by the imaging device, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration chambers via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1A, the microfluidic circuit 120 is illustrated as comprising a microfluidic channel 122 and sequestration chambers 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. The walls of the sequestration chamber extend from the inner surface 109 of the base to the inside surface of the cover 110 to provide enclosure. The opening of the pen to the microfluidic channel 122 is oriented at an angle to the flow 106 of fluidic medium 180 such that flow 106 is not directed into the pens. The flow may be tangential or orthogonal to the plane of the opening of the pen. In some instances, pens 124, 126, 128, 130 are configured to physically corral one or more micro-objects within the microfluidic circuit 120. Sequestration chambers in accordance with the present disclosure can comprise various shapes, surfaces and features that are optimized for use with DEP, OET, OEW, fluid flow, and/or gravitational forces, as will be discussed and shown in detail below.

The microfluidic circuit 120 may comprise any number of microfluidic sequestration chambers. Although five sequestration chambers are shown, microfluidic circuit 120 may have fewer or more sequestration chambers. As used herein, the terms "sequestration chamber" and "sequestration pen" are used interchangeably. As shown, microfluidic sequestration chambers 124, 126, 128, and 130 of microfluidic circuit 120 each comprise differing features and shapes which may provide one or more benefits useful in detecting cell-specific antibody secretions, such as isolating one B cell from an adjacent B cell. In some embodiments, the microfluidic circuit 120 comprises a plurality of identical microfluidic sequestration chambers.

In some embodiments, the microfluidic circuit 120 comprises a plurality of microfluidic sequestration chambers, wherein two or more of the sequestration chambers comprise differing structures and/or features which provide differing benefits in maintaining different types of cells. One non-limiting example may include maintaining B cells in one type of pen while maintaining cancer cells in a different type of pen.

In the embodiment illustrated in FIG. 1A, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration chambers is configured (e.g., relative to a channel 122) such that the sequestration chambers can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration chambers 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration chamber, such that upon tilting the microfluidic device 100 about an axis parallel to the microfluidic channel 122, the trapped micro-object exits the trap 132 at a trajectory that causes the micro-object to fall into the opening of the sequestration chamber. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration chambers) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration chamber. In some embodiments, DEP forces are used to prevent a micro-object within a sequestration chamber (e.g., sequestration pen 124, 126, 128, or 130) from being displaced therefrom. Further, in some embodiments, DEP forces are used to selectively remove a micro-object from a sequestration chamber that was previously collected in accordance with the embodiments of the current disclosure. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration chambers) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration chamber. In some embodiments, OEW forces are used to prevent a droplet within a sequestration chamber (e.g., sequestration chamber 124, 126, 128, or 130) from being displaced therefrom. Further, in some embodiments, OEW forces are used to selectively remove a droplet from a sequestration chamber that was previously collected in accordance with the embodiments of the current disclosure.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration chamber, and the force of gravity can transport the micro-objects and/or droplets into the chambers. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 1B:
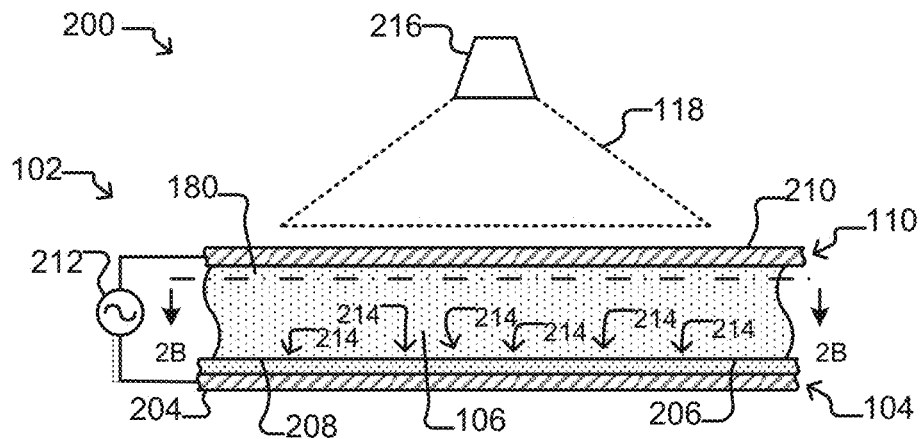
FIGS. 1B and 1C illustrate vertical and horizontal cross-sectional views, respectively, of a microfluidic device according to some embodiments.

FIGS. 1B, 1C, and 2A-2H illustrates various embodiments of microfluidic devices that can be used in the practice of the embodiments of the present disclosure. FIG. 1B depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an optoelectrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Examples of microfluidic devices having pens in which tumor-derived cells, such as B cells, T cells, or cancer cells can be placed, cultured, and/or monitored have been described, for example, in US 2014/0116881 (application Ser. No. 14/060,117, filed Oct. 22, 2013), US 2015/0151298 (application Ser. No. 14/520,568, filed Oct. 22, 2014), and US 2015/0165436 (application Ser. No. 14/521,447, filed Oct. 22, 2014), each of which is incorporated herein by reference in its entirety. U.S. application Ser. Nos. 14/520,568 and 14/521,447 also describe exemplary methods of analyzing secretions of cells cultured in a microfluidic device. Each of the foregoing applications further describes microfluidic devices configured to produce dielectrophoretic (DEP) forces, such as optoelectronic tweezers (OET) or configured to provide opto-electro wetting (OEW). For example, the optoelectronic tweezers device illustrated in FIG. 2 of US 2014/0116881 is an example of a device that can be utilized in embodiments of the present disclosure to select and move an individual biological micro-object or a group of biological micro-objects.

C. Microfluidic Device Motive Configurations.

As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 1C:
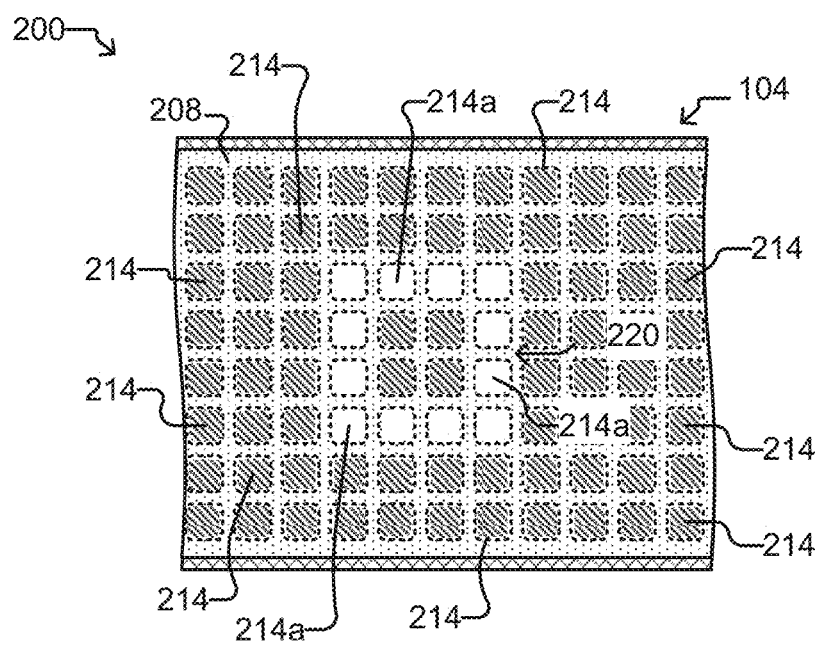

One example of a microfluidic device 200 comprising a DEP configuration is illustrated in FIGS. 1B and 1C. While for purposes of simplicity FIGS. 1B and 1C show a side cross-sectional view and a top cross-sectional view, respectively, of a portion of an enclosure 102 of the microfluidic device 200 having a region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 1B, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 1B and 1C can have an optically-actuated DEP configuration. Accordingly, changing patterns of light 218 from the light source 216, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 1C, a light pattern 218 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 218 projected from a light source 216 into the microfluidic device 200. Whether the DEP forces attract or repel nearby micro-objects can depend on such parameters as the frequency of the power source 212 and the dielectric properties of the medium 180 and/or micro-objects (not shown).

The square pattern 220 of illuminated DEP electrode regions 214a illustrated in FIG. 1C is an example only. Any pattern of the DEP electrode regions 214 can be illuminated (and thereby activated) by the pattern of light 218 projected into the microfluidic device 200, and the pattern of illuminated/activated DEP electrode regions 214 can be repeatedly changed by changing or moving the light pattern 218.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. In such embodiments, the DEP electrode regions 214 can be created anywhere and in any pattern on the inner surface 208 of the electrode activation substrate 206, in accordance with the light pattern 218. The number and pattern of the DEP electrode regions 214 thus need not be fixed, but can correspond to the light pattern 218. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields.

For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 218. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 218, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 218.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), and U.S. Patent Publication No. 2016/0184821 (Hobbs et al.) (see, e.g., devices 200, 502, 504, 600, and 700 illustrated throughout the drawings, and descriptions thereof), the entire contents of each of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 216 can alternatively be used to illuminate the enclosure 102 from below.

With the microfluidic device 200 of FIGS. 1B-1C having a DEP configuration, the motive module 162 can select a micro-object (not shown) in the medium 180 in the region/chamber 202 by projecting a light pattern 218 into the microfluidic device 200 to activate a first set of one or more DEP electrodes at DEP electrode regions 214a of the inner surface 208 of the electrode activation substrate 206 in a pattern (e.g., square pattern 220) that surrounds and captures the micro-object. The motive module 162 can then move the in situ-generated captured micro-object by moving the light pattern 218 relative to the microfluidic device 200 to activate a second set of one or more DEP electrodes at DEP electrode regions 214. Alternatively, the microfluidic device 200 can be moved relative to the light pattern 218.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 220), one or more micro-objects in region/chamber 202 can be trapped and moved within the region/chamber 202. The motive module 162 in FIG. 1A can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material, as described below. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™. Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 218 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 218 (or moving microfluidic device 200 relative to the light source 216) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1A can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

D. Sequestration Chambers.

Figure 2A:
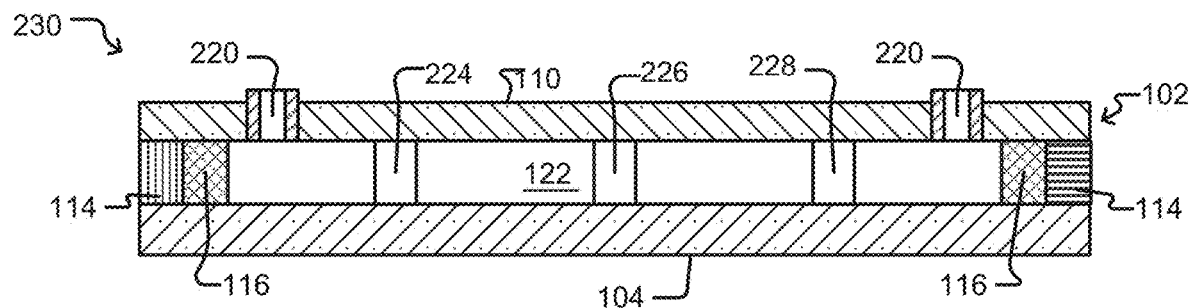
FIGS. 2A and 2B illustrate vertical and horizontal cross-sectional views, respectively, of a microfluidic device having isolation pens according to some embodiments.
Figure 2B:
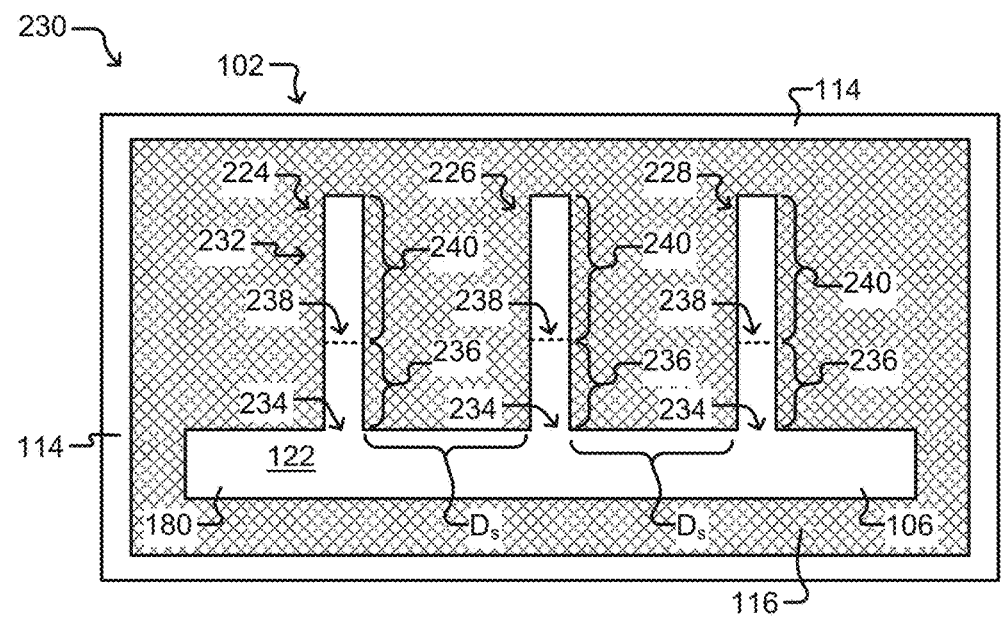
Figure 2C:
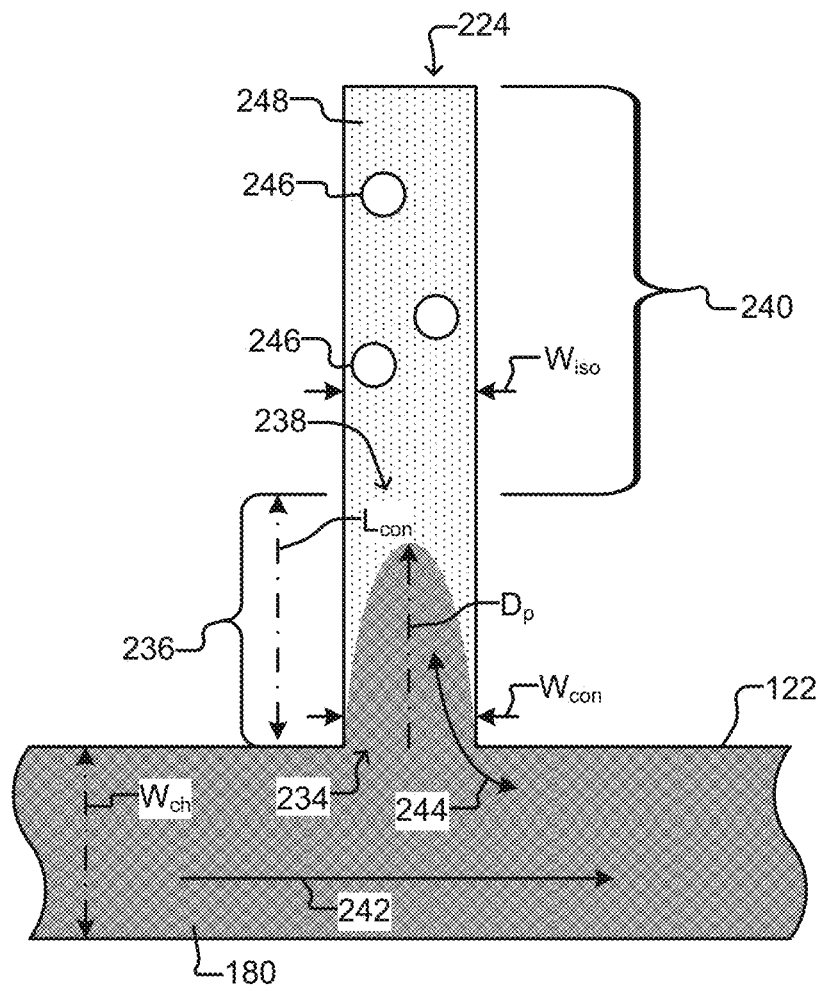
FIG. 2C illustrates a detailed horizontal cross-sectional view of a sequestration chamber according to some embodiments.

Non-limiting examples of generic sequestration chamber 224, 226, and 228 are shown within the microfluidic device 230 depicted in FIGS. 2A-2C. Each sequestration chamber 224, 226, and 228 can comprise an isolation structure 232 defining an isolation region 240 and a connection region 236 fluidically connecting the isolation region 240 to a channel 122. The connection region 236 can comprise a proximal opening 234 to the microfluidic channel 122 and a distal opening 238 to the isolation region 240. The connection region 236 can be configured so that the maximum penetration depth of a flow of a fluidic medium (not shown) flowing from the microfluidic channel 122 into the sequestration chamber 224, 226, 228 does not extend into the isolation region 240. Thus, due to the connection region 236, a micro-object (not shown) or other material (not shown) disposed in an isolation region 240 of a sequestration chamber 224, 226, 228 can thus be isolated from, and not substantially affected by, a flow of medium 180 in the microfluidic channel 122.

The sequestration chambers 224, 226, and 228 of FIGS. 2A-2C each have a single opening which opens directly to the microfluidic channel 122. The opening of the sequestration chamber opens laterally from the microfluidic channel 122. The electrode activation substrate 206 underlays both the microfluidic channel 122 and the sequestration chambers 224, 226, and 228. The upper surface of the electrode activation substrate 206 within the enclosure of a sequestration chamber, forming the floor of the sequestration chamber, is disposed at the same level or substantially the same level of the upper surface the of electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration chambers may be less than about 3%, 2%, 1%, 0.9%, 0.8%, 0.5%, 0.3% or 0.1% of the height of the walls of the sequestration chamber or walls of the microfluidic device. While described in detail for the microfluidic device 200, this also applies to any of the microfluidic devices 100, 230, 250, 280, 290, 320, 400, 450, 500, 700 described herein.

The microfluidic channel 122 can thus be an example of a swept region, and the isolation regions 240 of the sequestration chambers 224, 226, 228 can be examples of unswept regions. As noted, the microfluidic channel 122 and sequestration chambers 224, 226, 228 can be configured to contain one or more fluidic media 180. In the example shown in FIGS. 2A-2B, the ports 222 are connected to the microfluidic channel 122 and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 contains the fluidic medium 180, the flow 242 of fluidic medium 180 in the microfluidic channel 122 can be selectively generated and stopped. For example, as shown, the ports 222 can be disposed at different locations (e.g., opposite ends) of the microfluidic channel 122, and a flow 242 of medium can be created from one port 222 functioning as an inlet to another port 222 functioning as an outlet.

FIG. 2C illustrates a detailed view of an example of a sequestration chamber 224 according to the present disclosure. Examples of micro-objects 246 are also shown.

As is known, a flow 242 of fluidic medium 180 in a microfluidic channel 122 past a proximal opening 234 of sequestration chamber 224 can cause a secondary flow 244 of the medium 180 into and/or out of the sequestration chamber 224. To isolate micro-objects 246 in the isolation region 240 of a sequestration chamber 224 from the secondary flow 244, the length $L_{con}$ of the connection region 236 of the sequestration chamber 224 (i.e., from the proximal opening 234 to the distal opening 238) should be greater than the penetration depth $D_p$ of the secondary flow 244 into the connection region 236. The penetration depth $D_p$ of the secondary flow 244 depends upon the velocity of the fluidic medium 180 flowing in the microfluidic channel 122 and various parameters relating to the configuration of the microfluidic channel 122 and the proximal opening 234 of the connection region 236 to the microfluidic channel 122. For a given microfluidic device, the configurations of the microfluidic channel 122 and the opening 234 will be fixed, whereas the rate of flow 242 of fluidic medium 180 in the microfluidic channel 122 will be variable. Accordingly, for each sequestration chamber 224, a maximal velocity $V_{max}$ for the flow 242 of fluidic medium 180 in channel 122 can be identified that ensures that the penetration depth $D_p$ of the secondary flow 244 does not exceed the length $L_{con}$ of the connection region 236. As long as the rate of the flow 242 of fluidic medium 180 in the microfluidic channel 122 does not exceed the maximum velocity $V_{max}$, the resulting secondary flow 244 can be limited to the microfluidic channel 122 and the connection region 236 and kept out of the isolation region 240. The flow 242 of medium 180 in the microfluidic channel 122 will thus not draw micro-objects 246 out of the isolation region 240. Rather, micro-objects 246 located in the isolation region 240 will stay in the isolation region 240 regardless of the flow 242 of fluidic medium 180 in the microfluidic channel 122.

Moreover, as long as the rate of flow 242 of medium 180 in the microfluidic channel 122 does not exceed $V_{max}$, the flow 242 of fluidic medium 180 in the microfluidic channel 122 will not move miscellaneous particles (e.g., microparticles and/or nanoparticles) from the microfluidic channel 122 into the isolation region 240 of a sequestration chamber 224. Having the length $L_{con}$ of the connection region 236 be greater than the maximum penetration depth $D_p$ of the secondary flow 244 can thus prevent contamination of one sequestration chamber 224 with miscellaneous particles from the microfluidic channel 122 or another sequestration chamber (e.g., sequestration chambers 226, 228 in FIG. 2D).

Because the microfluidic channel 122 and the connection regions 236 of the sequestration chambers 224, 226, 228 can be affected by the flow 242 of medium 180 in the microfluidic channel 122, the microfluidic channel 122 and connection regions 236 can be deemed swept (or flow) regions of the microfluidic device 230. The isolation regions 240 of the sequestration chambers 224, 226, 228, on the other hand, can be deemed unswept (or non-flow) regions. For example, components (not shown) in a first fluidic medium 180 in the microfluidic channel 122 can mix with a second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration chamber and the flow region by diffusion is greater than about 90%, 91%, 92%, 93%, 94% 95%, 96%, 97%, 98%, or greater than about 99% of fluidic exchange. The first medium 180 can be the same medium or a different medium than the second medium 248. Moreover, the first medium 180 and the second medium 248 can start out being the same, then become different (e.g., through conditioning of the second medium 248 by one or more cells in the isolation region 240, or by changing the medium 180 flowing through the microfluidic channel 122).

The maximum penetration depth $D_p$ of the secondary flow 244 caused by the flow 242 of fluidic medium 180 in the microfluidic channel 122 can depend on a number of parameters, as mentioned above. Examples of such parameters include: the shape of the microfluidic channel 122 (e.g., the microfluidic channel can direct medium into the connection region 236, divert medium away from the connection region 236, or direct medium in a direction substantially perpendicular to the proximal opening 234 of the connection region 236 to the microfluidic channel 122); a width $W_{ch}$ (or cross-sectional area) of the microfluidic channel 122 at the proximal opening 234; and a width $W_{con}$ (or cross-sectional area) of the connection region 236 at the proximal opening 234; the velocity V of the flow 242 of fluidic medium 180 in the microfluidic channel 122; the viscosity of the first medium 180 and/or the second medium 248, or the like.

In some embodiments, the dimensions of the microfluidic channel 122 and sequestration chambers 224, 226, 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width $W_{con}$ (or cross-sectional area) of the connection region 236 at opening 234 can be substantially parallel to the flow 242 of medium 180 in the microfluidic channel 122; and/or the length $L_{con}$ of the connection region can be substantially perpendicular to the flow 242 of medium 180 in the microfluidic channel 122. The foregoing are examples only, and the relative position of the microfluidic channel 122 and sequestration chambers 224, 226, 228 can be in other orientations with respect to each other.

As illustrated in FIG. 2C, the width $W_{con}$ of the connection region 236 can be uniform from the proximal opening 234 to the distal opening 238. The width $W_{con}$ of the connection region 236 at the distal opening 238 can thus be in any of the ranges identified herein for the width $W_{con}$ of the connection region 236 at the proximal opening 234. Alternatively, the width $W_{con}$ of the connection region 236 at the distal opening 238 can be larger than the width $W_{con}$ of the connection region 236 at the proximal opening 234.

As illustrated in FIG. 2C, the width of the isolation region 240 at the distal opening 238 can be substantially the same as the width $W_{con}$ of the connection region 236 at the proximal opening 234. The width of the isolation region 240 at the distal opening 238 can thus be in any of the ranges identified herein for the width $W_{con}$ of the connection region 236 at the proximal opening 234. Alternatively, the width of the isolation region 240 at the distal opening 238 can be larger or smaller than the width $W_{con}$ of the connection region 236 at the proximal opening 234. Moreover, the distal opening 238 may be smaller than the proximal opening 234 and the width $W_{con}$ of the connection region 236 may be narrowed between the proximal opening 234 and distal opening 238. For example, the connection region 236 may be narrowed between the proximal opening and the distal opening, using a variety of different geometries (e.g. chamfering the connection region, beveling the connection region). Further, any part or subpart of the connection region 236 may be narrowed (e.g. a portion of the connection region adjacent to the proximal opening 234).

Figure 2D:
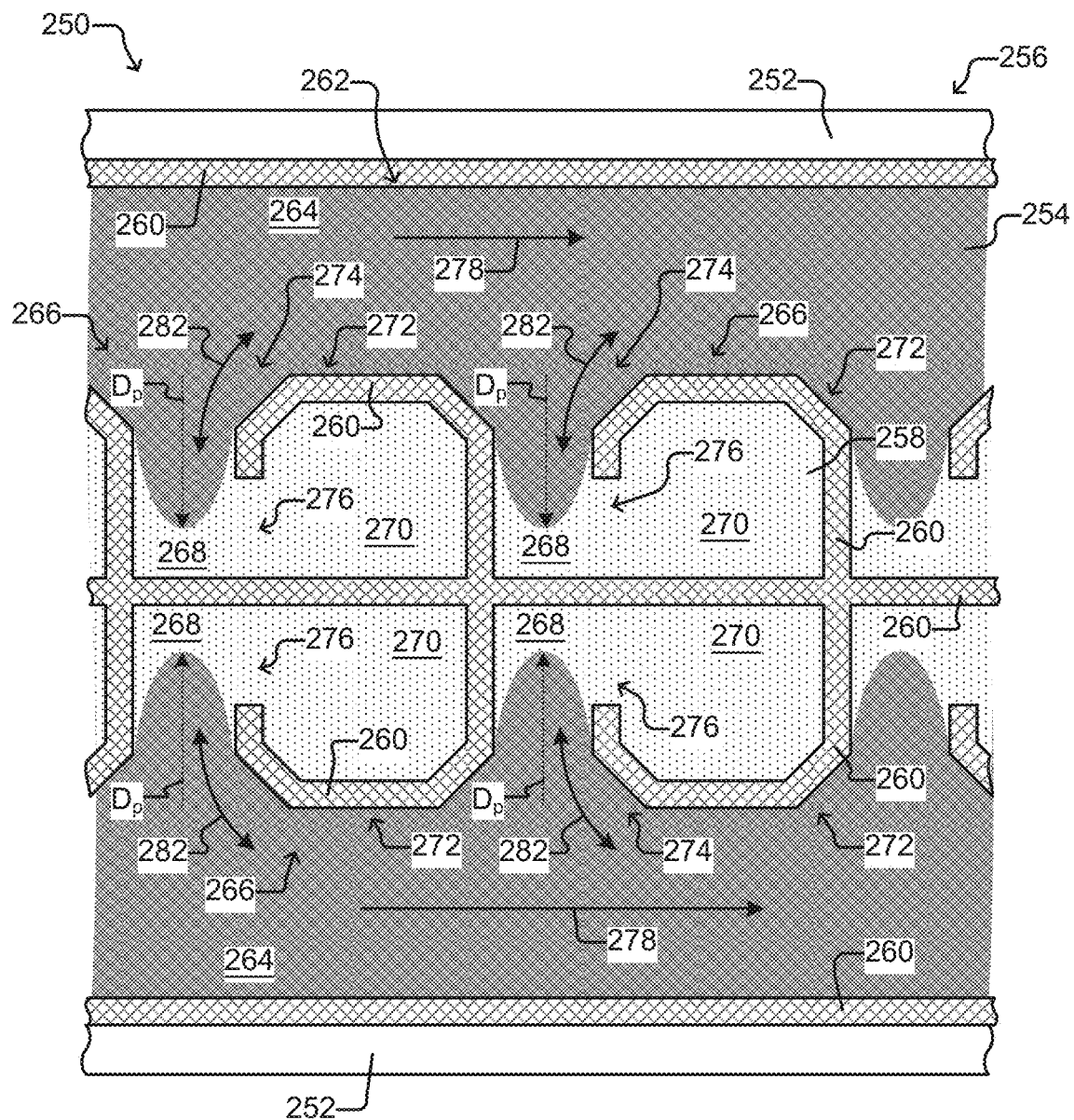
FIG. 2D illustrates a partial horizontal cross-sectional view of a microfluidic device having isolation pens according to some embodiments.
Figure 2E:
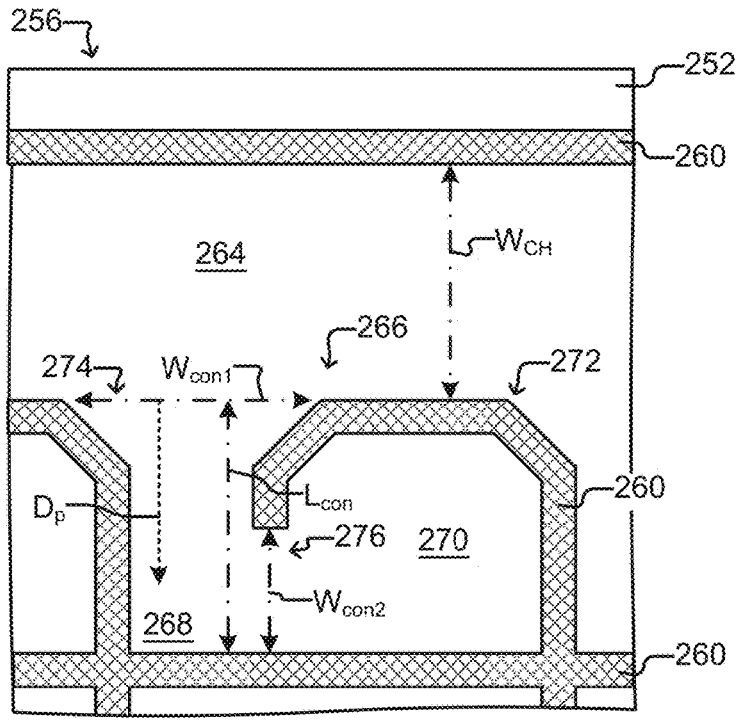
FIGS. 2E and 2F illustrate detailed horizontal cross-sectional views of sequestration chambers according to some embodiments.
Figure 2F:
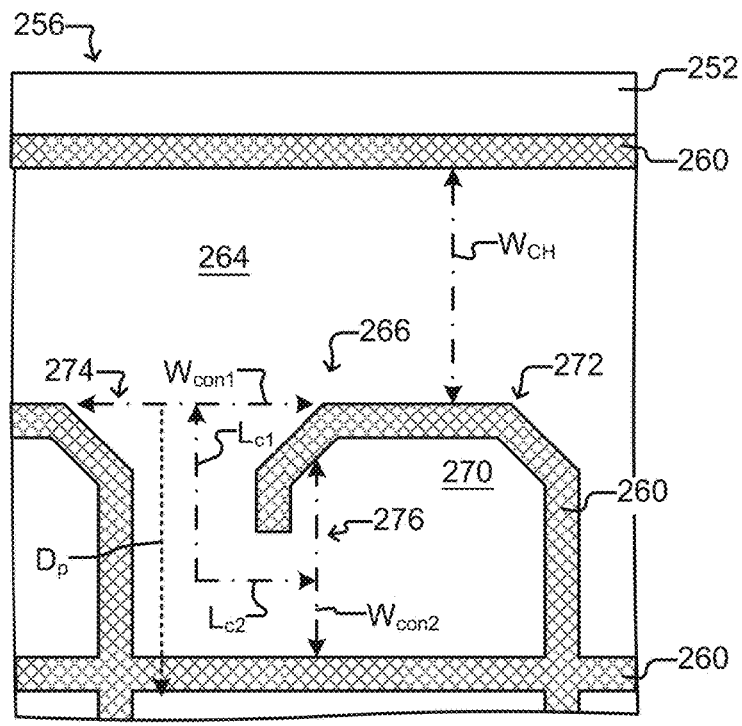

FIGS. 2D-2F depict another exemplary embodiment of a microfluidic device 250 containing a microfluidic circuit 262 and flow channels 264, which are variations of the respective microfluidic device 100, circuit 132 and channel 134 of FIG. 1A. The microfluidic device 250 also has a plurality of sequestration chambers 266 that are additional variations of the above-described sequestration chambers 124, 126, 128, 130, 224, 226 or 228. In particular, it should be appreciated that the sequestration chambers 266 of device 250 shown in FIGS. 2D-2F can replace any of the above-described sequestration chambers 124, 126, 128, 130, 224, 226 or 228 in devices 100, 200, 230, 280, 290, 300. Likewise, the microfluidic device 250 is another variant of the microfluidic device 100, and may also have the same or a different DEP configuration as the above-described microfluidic device 100, 200, 230, 280, 290, 300, as well as any of the other microfluidic system components described herein.

The microfluidic device 250 of FIGS. 2D-2F comprises a support structure (not visible in FIGS. 2D-2F, but can be the same or generally similar to the support structure 104 of device 100 depicted in FIG. 1A), a microfluidic circuit structure 256, and a cover (not visible in FIGS. 2D-2F, but can be the same or generally similar to the cover 122 of device 100 depicted in FIG. 1A). The microfluidic circuit structure 256 includes a frame 252 and microfluidic circuit material 260, which can be the same as or generally similar to the frame 114 and microfluidic circuit material 116 of device 100 shown in FIG. 1A. As shown in FIG. 2D, the microfluidic circuit 262 defined by the microfluidic circuit material 260 can comprise multiple channels 264 (two are shown but there can be more) to which multiple sequestration chambers 266 are fluidically connected.

Each sequestration chamber 266 can comprise an isolation structure 272, an isolation region 270 within the isolation structure 272, and a connection region 268. From a proximal opening 274 at the microfluidic channel 264 to a distal opening 276 at the isolation structure 272, the connection region 268 fluidically connects the microfluidic channel 264 to the isolation region 270. Generally, in accordance with the above discussion of FIGS. 2B and 2C, a flow 278 of a first fluidic medium 254 in a channel 264 can create secondary flows 282 of the first medium 254 from the microfluidic channel 264 into and/or out of the respective connection regions 268 of the sequestration chambers 266.

As illustrated in FIG. 2E, the connection region 268 of each sequestration chamber 266 generally includes the area extending between the proximal opening 274 to a channel 264 and the distal opening 276 to an isolation structure 272. The length $L_{con}$ of the connection region 268 can be greater than the maximum penetration depth $D_p$ of secondary flow 282, in which case the secondary flow 282 will extend into the connection region 268 without being redirected toward the isolation region 270 (as shown in FIG. 2D). Alternatively, at illustrated in FIG. 2F, the connection region 268 can have a length $L_{con}$ that is less than the maximum penetration depth $D_p$, in which case the secondary flow 282 will extend through the connection region 268 and be redirected toward the isolation region 270. In this latter situation, the sum of lengths $L_{c1}$ and $L_{c2}$ of connection region 268 is greater than the maximum penetration depth $D_p$, so that secondary flow 282 will not extend into isolation region 270. Whether length $L_{con}$ of connection region 268 is greater than the penetration depth $D_p$, or the sum of lengths $L_{c1}$ and $L_{c2}$ of connection region 268 is greater than the penetration depth $D_p$, a flow 278 of a first medium 254 in channel 264 that does not exceed a maximum velocity $V_{max}$ will produce a secondary flow having a penetration depth $D_p$, and micro-objects (not shown but can be the same or generally similar to the micro-objects 246 shown in FIG. 2C) in the isolation region 270 of a sequestration chamber 266 will not be drawn out of the isolation region 270 by a flow 278 of first medium 254 in channel 264. Nor will the flow 278 in channel 264 draw miscellaneous materials (not shown) from channel 264 into the isolation region 270 of a sequestration chamber 266. As such, diffusion is the only mechanism by which components in a first medium 254 in the microfluidic channel 264 can move from the microfluidic channel 264 into a second medium 258 in an isolation region 270 of a sequestration chamber 266. Likewise, diffusion is the only mechanism by which components in a second medium 258 in an isolation region 270 of a sequestration chamber 266 can move from the isolation region 270 to a first medium 254 in the microfluidic channel 264. The first medium 254 can be the same medium as the second medium 258, or the first medium 254 can be a different medium than the second medium 258. Alternatively, the first medium 254 and the second medium 258 can start out being the same, then become different, e.g., through conditioning of the second medium by one or more cells in the isolation region 270, or by changing the medium flowing through the microfluidic channel 264.

As illustrated in FIG. 2E, the width $W_{ch}$ of the microfluidic channels 264 (i.e., taken transverse to the direction of a fluid medium flow through the microfluidic channel indicated by arrows 278 in FIG. 2D) in the microfluidic channel 264 can be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented can be other than perpendicular and thus other than 90°. Examples of alternatively oriented angles include angles in any of the following ranges: from about 300 to about 90°, from about 45 to about 90°, from about 600 to about 90°, or the like.

In various embodiments of sequestration chambers (e.g. 124, 126, 128, 130, 224, 226, 228, or 266), the isolation region (e.g. 240 or 270) is configured to contain a plurality of micro-objects. In other embodiments, the isolation region can be configured to contain only one, two, three, four, five, or a similar relatively small number of micro-objects. Accordingly, the volume of an isolation region can be, for example, at least $1\times10^6$, $2\times10^6$, $4\times10^6$, $6\times10^6$ cubic microns, or more.

In various embodiments of sequestration chambers, the width $W_{ch}$ of the microfluidic channel (e.g., 122) at a proximal opening (e.g. 234) can be within any of the following ranges: about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. In some other embodiments, the width $W_{ch}$ of the microfluidic channel (e.g., 122) at a proximal opening (e.g. 234) can be in a range of about 200-800 microns, 200-700 microns, or 200-600 microns. The foregoing are examples only, and the width $W_{ch}$ of the microfluidic channel 122 can be in other ranges (e.g., a range defined by any of the endpoints listed above). Moreover, the $W_{ch}$ of the microfluidic channel 122 can be selected to be in any of these ranges in regions of the microfluidic channel other than at a proximal opening of a sequestration chamber.

In some embodiments, a sequestration chamber has a height of about 30 to about 200 microns, or about 50 to about 150 microns. In some embodiments, the sequestration chamber has a cross-sectional area of about $1\times10^4$-$3\times10^6$ square microns, $2\times10^4$-$2\times10^6$ square microns, $4\times10^4$-$1\times10^6$ square microns, $2\times10^4$-$5\times10^5$ square microns, $2\times10^4$-$1\times10^5$ square microns or about $2\times10^5$-$2\times10^6$ square microns.

In various embodiments of sequestration chambers, the height $H_{ch}$ of the microfluidic channel (e.g., 122) at a proximal opening (e.g., 234) can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the microfluidic channel (e.g., 122) can be in other ranges (e.g., a range defined by any of the endpoints listed above). The height $H_{ch}$ of the microfluidic channel 122 can be selected to be in any of these ranges in regions of the microfluidic channel other than at a proximal opening of an sequestration chamber.

In various embodiments of sequestration chamber a cross-sectional area of the microfluidic channel (e.g., 122) at a proximal opening (e.g., 234) can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel (e.g., 122) at a proximal opening (e.g., 234) can be in other ranges (e.g., a range defined by any of the endpoints listed above).

In various embodiments of sequestration chambers, the length $L_{con}$ of the connection region (e.g., 236) can be in any of the following ranges: about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length $L_{con}$ of a connection region (e.g., 236) can be in a different range than the foregoing examples (e.g., a range defined by any of the endpoints listed above).

In various embodiments of sequestration chambers the width $W_{con}$ of a connection region (e.g., 236) at a proximal opening (e.g., 234) can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region (e.g., 236) at a proximal opening (e.g., 234) can be different than the foregoing examples (e.g., a range defined by any of the endpoints listed above).

In various embodiments of sequestration chambers, the width $W_{pr}$ of a proximal opening of a connection region may be at least as large as the largest dimension of a micro-object (e.g., a biological micro-object such as a cell) that the sequestration chamber is intended for. For example, the width $W_{pr}$ may be about 50 microns, about 60 microns, about 100 microns, about 200 microns, about 300 microns or may be in a range of about 50-300 microns, about 50-200 microns, about 50-100 microns, about 75-150 microns, about 75-100 microns, or about 200-300 microns In various embodiments of sequestration chambers, a ratio of the length $L_{con}$ of a connection region (e.g., 236) to a width $W_{con}$ of the connection region (e.g., 236) at the proximal opening 234 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 236 to a width $W_{con}$ of the connection region 236 at the proximal opening 234 can be different than the foregoing examples.

In various embodiments of microfluidic devices 100, 200, 23, 250, 280, 290, 300, $V_{max}$ can be set around 0.2, 0.3, 0.4, 0.5, 0.6, 0.7, 0.8, 0.9, 1.0, 1.1, 1.2, 1.3, 1.4, or 1.5 microliters/sec.

In various embodiments of microfluidic devices having sequestration chambers, the volume of an isolation region (e.g., 240) of a sequestration chamber can be, for example, at least $5\times10^5$, $8\times10^5$, $1\times10^6$, $2\times10^6$, $4\times10^6$, $6\times10^6$, $8\times10^6$, $1\times10^7$, $5\times10^7$, $1\times10^8$, $5\times10^8$, or $8\times10^8$ cubic microns, or more. In various embodiments of microfluidic devices having sequestration chambers, the volume of a sequestration chamber may be about $5\times10^5$, $6\times10^5$, $8\times10^5$, $1\times10^6$, $2\times10^6$, $4\times10^6$, $8\times10^6$, $1\times10^7$, $3\times10^7$, $5\times10^7$, or about $8\times10^7$ cubic microns, or more. In some other embodiments, the volume of a sequestration chamber may be about 1 nanoliter to about 50 nanoliters, 2 nanoliters to about 25 nanoliters, 2 nanoliters to about 20 nanoliters, about 2 nanoliters to about 15 nanoliters, or about 2 nanoliters to about 10 nanoliters.

In various embodiment, the microfluidic device has sequestration chambers configured as in any of the embodiments discussed herein where the microfluidic device has about 5 to about 10 sequestration chambers, about 10 to about 50 sequestration chambers, about 100 to about 500 sequestration chambers; about 200 to about 1000 sequestration chambers, about 500 to about 1500 sequestration chambers, about 1000 to about 2000 sequestration chambers, or about 1000 to about 3500 sequestration chambers. The sequestration chambers need not all be the same size and may include a variety of configurations (e.g., different widths, different features within the sequestration chamber.

Figure 2G:
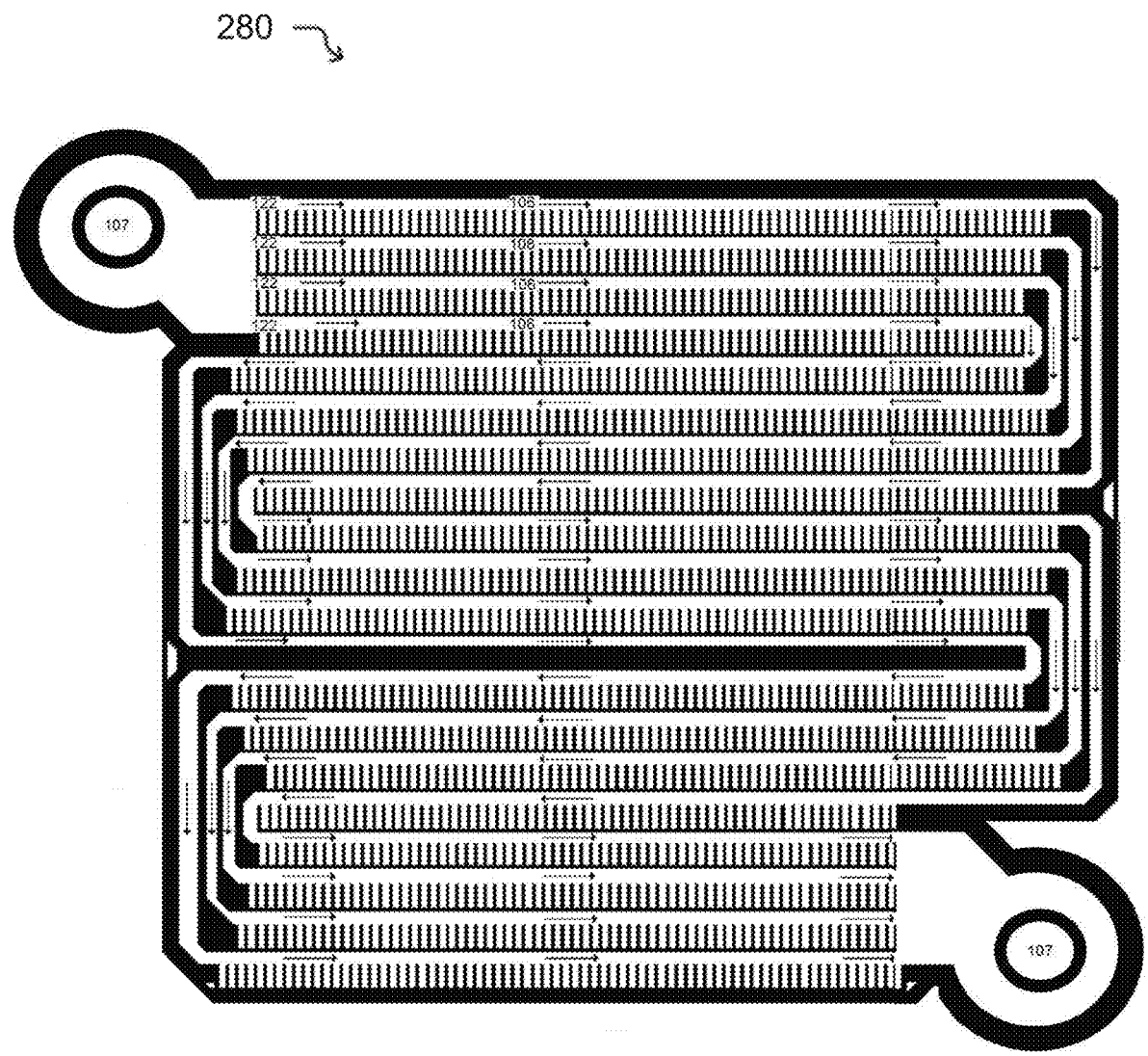
FIG. 2G illustrates a microfluidic device having a flow region which contains a plurality of flow channels, each flow channel fluidically connected to a plurality of sequestration chambers, according to an embodiment.

FIG. 2G illustrates a microfluidic device 280 according to one embodiment. The microfluidic device 280 is illustrated in FIG. 2G is a stylized diagram of a microfluidic device 100. In practice the microfluidic device 280 and its constituent circuit elements (e.g. channels 122 and sequestration chambers 128) would have the dimensions discussed herein. The microfluidic circuit 120 illustrated in FIG. 2G has two ports 107, four distinct channels 122 and four distinct flow paths 106. The microfluidic device 280 further comprises a plurality of sequestration chambers opening off of each channel 122. In the microfluidic device illustrated in FIG. 2G, the sequestration chambers have a geometry similar to the pens illustrated in FIG. 2C and thus, have both connection regions and isolation regions. Accordingly, the microfluidic circuit 120 includes both swept regions (e.g. channels 122 and portions of the connection regions 236 within the maximum penetration depth $D_p$ of the secondary flow 244) and non-swept regions (e.g. isolation regions 240 and portions of the connection regions 236 not within the maximum penetration depth $D_p$ of the secondary flow 244).

E. System Nest

Figure 3A:
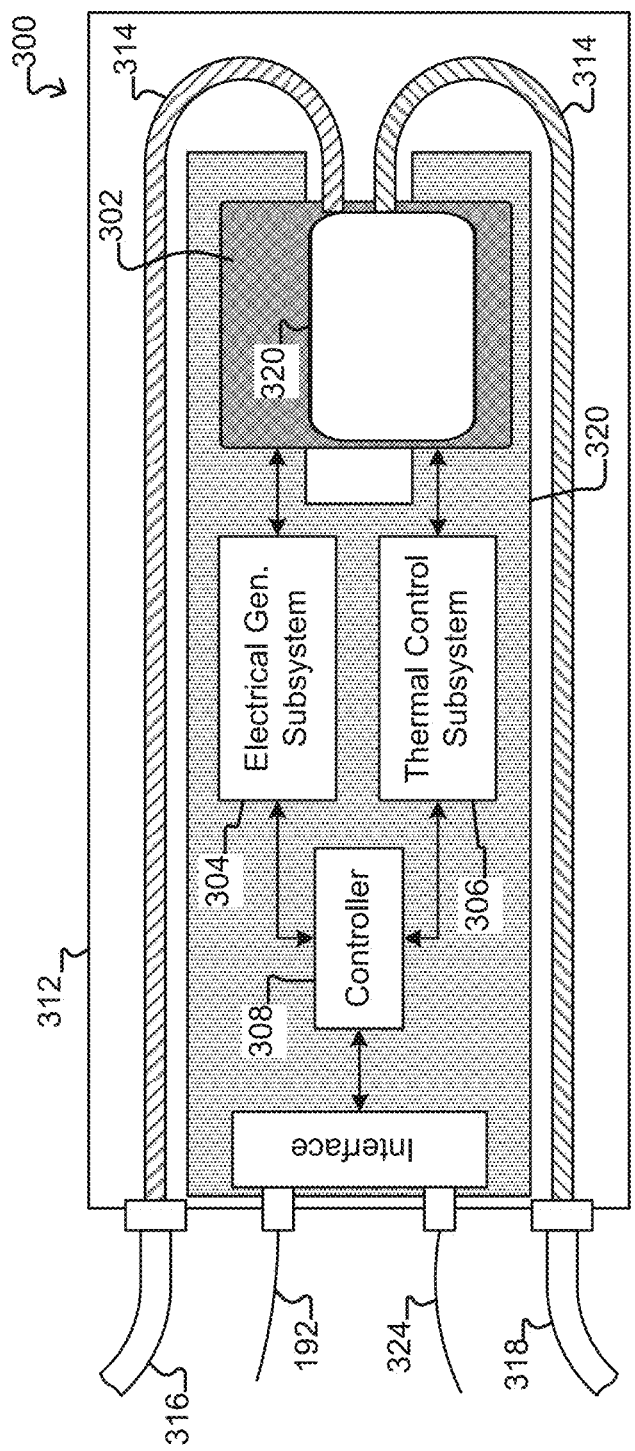
FIG. 3A illustrates a specific example of a system nest, configured to operatively couple with a microfluidic device, and associated control equipment according to some embodiments.
Figure 3B:
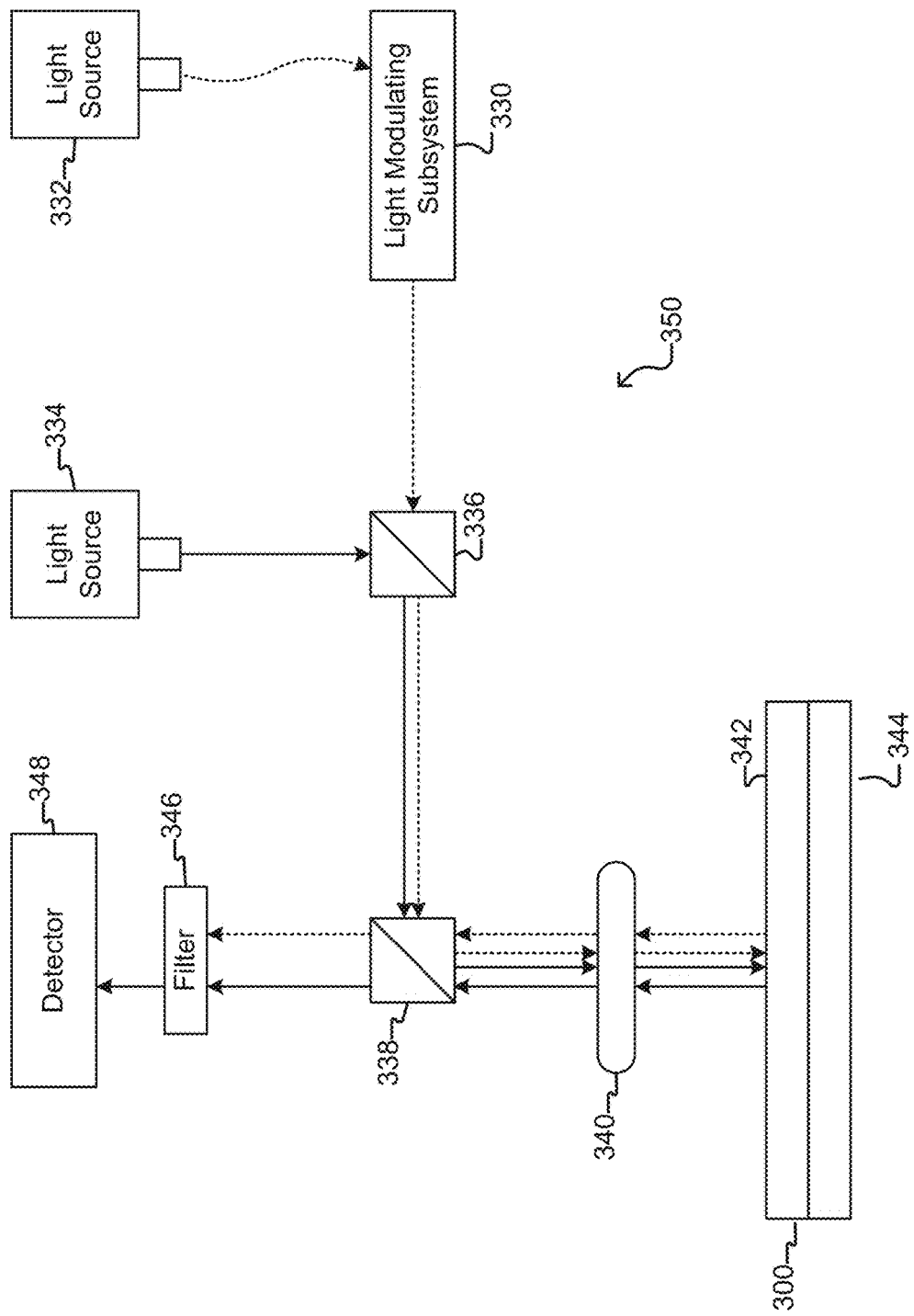
FIG. 3B illustrates an optical train of a system for controlling a microfluidic device according to some embodiments.

FIGS. 3A through 3B shows various embodiments of system 150 which can be used to operate and observe microfluidic devices (e.g. 100, 200, 230, 250, 280, 290, 300) according to the present disclosure. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 320 (e.g., an optically-actuated electrokinetic device 100) and providing electrical connections from power source 192 to microfluidic device 320. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 320 when it is being held by socket 302. Thus, the electrical signal generation subsystem 304 can be part of power source 192. The ability to apply a biasing voltage to microfluidic device 320 does not mean that a biasing voltage will be applied at all times when the microfluidic device 320 is held by the socket 302. Rather, in most cases, the biasing voltage will be applied intermittently, e.g., only as needed to facilitate the generation of electrokinetic forces, such as dielectrophoresis or electro-wetting, in the microfluidic device 320.

As illustrated in FIG. 3A, the nest 300 can include a printed circuit board assembly (PCBA) 322. The electrical signal generation subsystem 304 can be mounted on and electrically integrated into the PCBA 322. The exemplary support includes socket 302 mounted on PCBA 322, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1A) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 100.

As illustrated in FIG. 3A, the support structure 300 (e.g., nest) can further include a thermal control subsystem 306. The thermal control subsystem 306 can be configured to regulate the temperature of microfluidic device 320 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 320. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 314 configured to circulate cooled fluid through the cooling block. In the embodiment illustrated in FIG. 3A, the support structure 300 comprises an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 can be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient+/−0.02 ppm/CO) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 324 which allows the microprocessor of the controller 308 to communicate with an external master controller 154 via the interface. In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 324, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI) (not shown) provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

F. System Imaging Device

As discussed above, system 150 can include an imaging device. In some embodiments, the imaging device comprises a light modulating subsystem 330 (See FIG. 3B). The light modulating subsystem 330 can include a digital mirror device (DMD) or a microshutter array system (MSA), either of which can be configured to receive light from a light source 332 and transmits a subset of the received light into an optical train of microscope 350. Alternatively, the light modulating subsystem 330 can include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 can be, for example, a projector. Thus, the light modulating subsystem 330 can be capable of emitting both structured and unstructured light. One example of a suitable light modulating subsystem 330 is the Mosaic™ system from Andor Technologies™. In certain embodiments, imaging module 164 and/or motive module 162 of system 150 can control the light modulating subsystem 330.

In certain embodiments, the imaging device further comprises a microscope 350. In such embodiments, the nest 300 and light modulating subsystem 330 can be individually configured to be mounted on the microscope 350. The microscope 350 can be, for example, a standard research-grade light microscope or fluorescence microscope. Thus, the nest 300 can be configured to be mounted on the stage 344 of the microscope 350 and/or the light modulating subsystem 330 can be configured to mount on a port of microscope 350. In other embodiments, the nest 300 and the light modulating subsystem 330 described herein can be integral components of microscope 350.

In certain embodiments, the microscope 350 can further include one or more detectors 348. In some embodiments, the detector 348 is controlled by the imaging module 164. The detector 348 can include an eye piece, a charge-coupled device (CCD), a camera (e.g., a digital camera), or any combination thereof. If at least two detectors 348 are present, one detector can be, for example, a fast-frame-rate camera while the other detector can be a high sensitivity camera. Furthermore, the microscope 350 can include an optical train configured to receive reflected and/or emitted light from the microfluidic device 320 and focus at least a portion of the reflected and/or emitted light on the one or more detectors 348. The optical train of the microscope can also include different tube lenses (not shown) for the different detectors, such that the final magnification on each detector can be different.

In certain embodiments, imaging device is configured to use at least two light sources. For example, a first light source 332 can be used to produce structured light (e.g., via the light modulating subsystem 330) and a second light source 334 can be used to provide unstructured light. The first light source 332 can produce structured light for optically-actuated electrokinesis and/or fluorescent excitation, and the second light source 334 can be used to provide bright field illumination. In these embodiments, the motive module 164 can be used to control the first light source 332 and the imaging module 164 can be used to control the second light source 334. The optical train of the microscope 350 can be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region. In other embodiments, the second light source 334 may additionally or alternatively include a laser, which may have any suitable wavelength of light. The representation of the optical system shown in FIG. 3B is a schematic representation only, and the optical system may include additional filters, notch filters, lenses and the like. When the second light source 334 includes one or more light source(s) for brightfield and/or fluorescent excitation, as well as laser illumination the physical arrangement of the light source(s) may vary from that shown in FIG. 3B, and the laser illumination may be introduced at any suitable physical location within the optical system. The schematic locations of light source 432 and light source 402/light modulating subsystem 404 may be interchanged as well.

In FIG. 3B, the first light source 332 is shown supplying light to a light modulating subsystem 330, which provides structured light to the optical train of the microscope 350 of system 355 (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective 336 to the sample plane 342. Reflected and/or emitted light from the sample plane 342 then travels back up through the objective 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This can be beneficial if the first light source 332 is significantly stronger than the second light source 334. In other embodiments, the second light source 334 can emit red light, and the dichroic filter 346 can filter out visible light other than red light (e.g., visible light having a wavelength shorter than 650 nm).

G. Coating Solutions and Coating Agents.

Without intending to be limited by theory, maintenance of a biological micro-object (e.g., a biological cell) within a microfluidic device (e.g., a DEP-configured and/or EW-configured microfluidic device) may be facilitated (i.e., the biological micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and biological micro-object(s) maintained therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the biological micro-object(s) into the microfluidic device.

In some embodiments, at least one surface of the microfluidic device includes a coating material that provides a layer of organic and/or hydrophilic molecules suitable for maintenance and/or expansion of biological micro-object(s) (e.g. provides a conditioned surface as described below). In some embodiments, substantially all the inner surfaces of the microfluidic device include the coating material. The coated inner surface(s) may include the surface of a flow region (e.g., channel), chamber, or sequestration chamber, or a combination thereof. In some embodiments, each of a plurality of sequestration chambers has at least one inner surface coated with coating materials. In other embodiments, each of a plurality of flow regions or channels has at least one inner surface coated with coating materials. In some embodiments, at least one inner surface of each of a plurality of sequestration chambers and each of a plurality of channels is coated with coating materials.

Coating Agent/Solution.

Any convenient coating agent/coating solution can be used, including but not limited to: serum or serum factors, bovine serum albumin (BSA), polymers, detergents, enzymes, and any combination thereof.

Polymer-Based Coating Materials.

The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da. In other embodiments, the coating material may include a polymer containing carboxylic acid moieties. The carboxylic acid subunit may be an alkyl, alkenyl or aromatic moiety containing subunit. One non-limiting example is polylactic acid (PLA). In other embodiments, the coating material may include a polymer containing phosphate moieties, either at a terminus of the polymer backbone or pendant from the backbone of the polymer. In yet other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer containing saccharide moieties. In a non-limiting example, polysaccharides such as xanthan gum or dextran may be suitable to form a material which may reduce or prevent cell sticking in the microfluidic device. For example, a dextran polymer having a size about 3 kDa may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties, providing a polyelectrolyte surface. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA) and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a coating solution is present in a range of form about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a coating solution may be present in a range of from about 20% (v/v) to about 50% v/v, including 25%, 30%, 35%, 40%, 45%, or more or anywhere in between. In some embodiments, BSA may be present as a coating agent in a coating solution at 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently Linked Coating Materials.

In some embodiments, the at least one inner surface includes covalently linked molecules that provide a layer of organic and/or hydrophilic molecules suitable for maintenance/expansion of biological micro-object(s) within the microfluidic device, providing a conditioned surface for such cells.

The covalently linked molecules include a linking group, wherein the linking group is covalently linked to one or more surfaces of the microfluidic device, as described below. The linking group is also covalently linked to a moiety configured to provide a layer of organic and/or hydrophilic molecules suitable for maintenance/expansion of biological micro-object(s).

In some embodiments, the covalently linked moiety configured to provide a layer of organic and/or hydrophilic molecules suitable for maintenance/expansion of biological micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocyclic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of biological micro-object(s) in the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may be any of the moieties described above.

In some embodiments, the covalently linked alkyl moiety may comprises carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may include at least one alkylene oxide moiety, and may include any alkylene oxide polymer as described above. One useful class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the sequestration chambers and/or flow regions (e.g., channels).

The coating material providing a conditioned surface may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having charged moieties covalently attached to an alkyl or fluoroalkyl chain having a greater number of methylene or fluoromethylene units, which may provide capacity to present bulkier moieties at the coated surface. In this instance, the first set of molecules having different, less sterically demanding termini and fewer backbone atoms can help to functionalize the entire substrate surface and thereby prevent undesired adhesion or contact with the silicon/silicon oxide, hafnium oxide or alumina making up the substrate itself. In another example, the covalently linked moieties may provide a zwitterionic surface presenting alternating charges in a random fashion on the surface.

Conditioned Surface Properties.

Aside from the composition of the conditioned surface, other factors such as physical thickness of the hydrophobic material can impact DEP force. Various factors can alter the physical thickness of the conditioned surface, such as the manner in which the conditioned surface is formed on the substrate (e.g. vapor deposition, liquid phase deposition, spin coating, flooding, and electrostatic coating). In some embodiments, the conditioned surface has a thickness in the range of about 1 nm to about 10 nm; about 1 nm to about 7 nm; about 1 nm to about 5 nm; or any individual value therebetween. In other embodiments, the conditioned surface formed by the covalently linked moieties may have a thickness of about 10 nm to about 50 nm. In various embodiments, the conditioned surface prepared as described herein has a thickness of less than 10 nm. In some embodiments, the covalently linked moieties of the conditioned surface may form a monolayer when covalently linked to the surface of the microfluidic device (e.g., a DEP configured substrate surface) and may have a thickness of less than 10 nm (e.g., less than 5 nm, or about 1.5 to 3.0 nm). These values are in contrast to that of a CYTOP® (Asahi Glass Co., Ltd. JP) fluoropolymer spin coating, which has a thickness in the range of about 30 nm. In some embodiments, the conditioned surface does not require a perfectly formed monolayer to be suitably functional for operation within a DEP-configured microfluidic device.

In various embodiments, the coating material providing a conditioned surface of the microfluidic device may provide desirable electrical properties. Without intending to be limited by theory, one factor that impacts robustness of a surface coated with a particular coating material is intrinsic charge trapping. Different coating materials may trap electrons, which can lead to breakdown of the coating material. Defects in the coating material may increase charge trapping and lead to further breakdown of the coating material. Similarly, different coating materials have different dielectric strengths (i.e. the minimum applied electric field that results in dielectric breakdown), which may impact charge trapping. In certain embodiments, the coating material can have an overall structure (e.g., a densely-packed monolayer structure) that reduces or limits that amount of charge trapping.

In addition to its electrical properties, the conditioned surface may also have properties that are beneficial in use with biological molecules. For example, a conditioned surface that contains fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Unitary or Multi-Part Conditioned Surface.

The covalently linked coating material may be formed by reaction of a molecule which already contains the moiety configured to provide a layer of organic and/or hydrophilic molecules suitable for maintenance/expansion of biological micro-object(s) in the microfluidic device, as is described below. Alternatively, the covalently linked coating material may be formed in a two-part sequence by coupling the moiety configured to provide a layer of organic and/or hydrophilic molecules suitable for maintenance/expansion of biological micro-object(s) to a surface modifying ligand that itself has been covalently linked to the surface.

Methods of Preparing a Covalently Linked Coating Material.

In some embodiments, a coating material that is covalently linked to the surface of a microfluidic device (e.g., including at least one surface of the sequestration chambers and/or flow regions) has a structure of Formula 1 or Formula 2. When the coating material is introduced to the surface in one step, it has a structure of Formula 1, while when the coating material is introduced in a multiple step process, it has a structure of Formula 2.

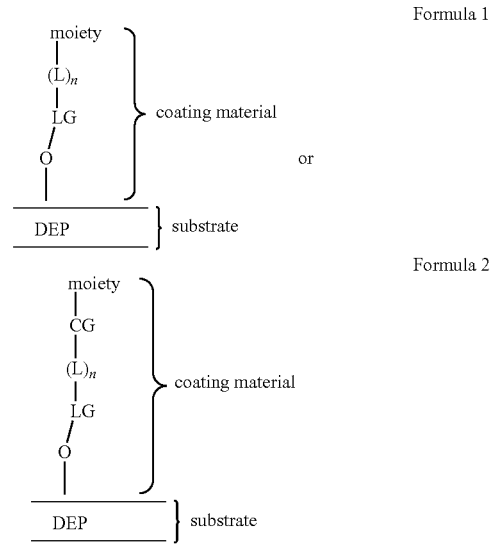

The coating material may be linked covalently to oxides of the surface of a DEP-configured or EW-configured substrate. The DEP- or EW-configured substrate may comprise silicon, silicon oxide, alumina, or hafnium oxide. Oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for maintenance/expansion of biological micro-object(s) in the microfluidic device can be any of the moieties described herein. The linking group LG may be directly or indirectly connected to the moiety configured to provide a layer of organic and/or hydrophilic molecules suitable for maintenance/expansion of biological micro-object(s) in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and phosphorus atoms, subject to chemical bonding limitations as is known in the art. It may be interrupted with any combination of one or more moieties selected from the group of ether, amino, carbonyl, amido, or phosphonate groups, arylene, heteroarylene, or heterocyclic groups. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms.

In some embodiments, the moiety configured to provide a layer of organic and/or hydrophilic molecules suitable for maintenance/expansion of biological micro-object(s) may be added to the surface of the substrate in a multi-step process, and has a structure of Formula 2, as shown above. The moiety may be any of the moieties described above.

In some embodiments, the coupling group CG represents the resultant group from reaction of a reactive moiety RX and a reactive pairing moiety Rpx (i.e., a moiety configured to react with the reactive moiety RX). For example, one typical coupling group CG may include a carboxamidyl group, which is the result of the reaction of an amino group with a derivative of a carboxylic acid, such as an activated ester, an acid chloride or the like. Other CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to provide a layer of organic and/or hydrophilic molecules suitable for maintenance/expansion of biological micro-object(s) in the microfluidic device) of linker L, which may include any combination of elements as described above. In some other embodiments, the coupling group CG may interrupt the backbone of the linker L. When the coupling group CG is triazolylene, it may be the product resulting from a Click coupling reaction and may be further substituted (e.g., a dibenzocylcooctenyl fused triazolylene group).

In some embodiments, the coating material (or surface modifying ligand) is deposited on the inner surfaces of the microfluidic device using chemical vapor deposition. The vapor deposition process can be optionally improved, for example, by pre-cleaning the cover 110, the microfluidic circuit material 116, and/or the substrate (e.g., the inner surface 208 of the electrode activation substrate 206 of a DEP-configured substrate, or a dielectric layer of the support structure 104 of an EW-configured substrate), by exposure to a solvent bath, sonication or a combination thereof. Alternatively, or in addition, such pre-cleaning can include treating the cover 110, the microfluidic circuit material 116, and/or the substrate in an oxygen plasma cleaner, which can remove various impurities, while at the same time introducing an oxidized surface (e.g. oxides at the surface, which may be covalently modified as described herein). Alternatively, liquid-phase treatments, such as a mixture of hydrochloric acid and hydrogen peroxide or a mixture of sulfuric acid and hydrogen peroxide (e.g., piranha solution, which may have a ratio of sulfuric acid to hydrogen peroxide in a range from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102 defining a microfluidic circuit 120. Without intending to be limited by theory, depositing such a coating material on a fully-assembled microfluidic circuit 120 may be beneficial in preventing delamination caused by a weakened bond between the microfluidic circuit material 116 and the electrode activation substrate 206 dielectric layer and/or the cover 110. In embodiments where a two-step process is employed the surface modifying ligand may be introduced via vapor deposition as described above, with subsequent introduction of the moiety configured provide a layer of organic and/or hydrophilic molecules suitable for maintenance/expansion of biological micro-object(s). The subsequent reaction may be performed by exposing the surface modified microfluidic device to a suitable coupling reagent in solution.

Figure 2H:
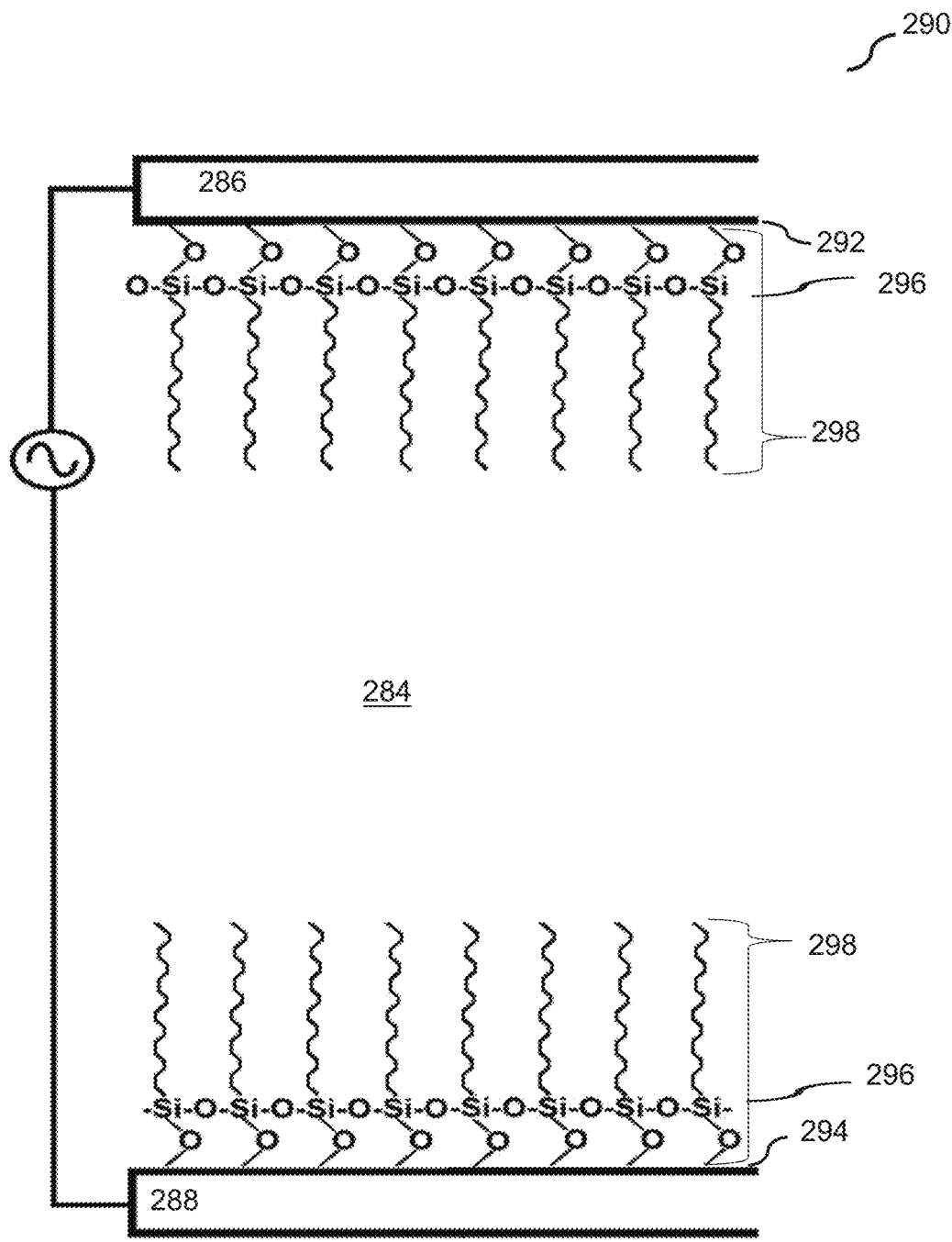
FIG. 2H illustrates a partial vertical cross-sectional view of a microfluidic device in which the inward facing surface of the base and the inward facing surface of the cover are conditioned surfaces according to some embodiments.

FIG. 2H depicts a cross-sectional view of a microfluidic device 290 having an exemplary covalently linked coating material providing a conditioned surface. As illustrated, the coating materials 298 (shown schematically) can comprise a monolayer of densely-packed molecules covalently bound to both the inner surface 294 of a base 286, which may be a DEP substrate, and the inner surface 292 of a cover 288 of the microfluidic device 290. The coating material 298 can be disposed on substantially all inner surfaces 294, 292 proximal to, and facing inwards towards, the enclosure 284 of the microfluidic device 290, including, in some embodiments and as discussed above, the surfaces of microfluidic circuit material (not shown) used to define circuit elements and/or structures within the microfluidic device 290. In alternate embodiments, the coating material 298 can be disposed on only one or some of the inner surfaces of the microfluidic device 290.

In the embodiment shown in FIG. 2H, the coating material 298 can include a monolayer of organosiloxane molecules, each molecule covalently bonded to the inner surfaces 292, 294 of the microfluidic device 290 via a siloxy linker 296. Any of the above-discussed coating materials 298 can be used (e.g. an alkyl-terminated, a fluoroalkyl terminated moiety, a PEG-terminated moiety, a dextran terminated moiety, or a terminal moiety containing positive or negative charges for the organosiloxy moieties), where the terminal moiety is disposed at its enclosure-facing terminus (i.e. the portion of the monolayer of the coating material 298 that is not bound to the inner surfaces 292, 294 and is proximal to the enclosure 284).

In other embodiments, the coating material 298 used to coat the inner surface(s) 292, 294 of the microfluidic device 290 can include anionic, cationic, or zwitterionic moieties, or any combination thereof. Without intending to be limited by theory, by presenting cationic moieties, anionic moieties, and/or zwitterionic moieties at the inner surfaces of the enclosure 284 of the microfluidic circuit 120, the coating material 298 can form strong hydrogen bonds with water molecules such that the resulting water of hydration acts as a layer (or "shield") that separates the biological micro-objects from interactions with non-biological molecules (e.g., the silicon and/or silicon oxide of the substrate). In addition, in embodiments in which the coating material 298 is used in conjunction with coating agents, the anions, cations, and/or zwitterions of the coating material 298 can form ionic bonds with the charged portions of non-covalent coating agents (e.g. proteins in solution) that are present in a medium 180 (e.g. a coating solution) in the enclosure 284.

In still other embodiments, the coating material may comprise or be chemically modified to present a hydrophilic coating agent at its enclosure-facing terminus. In some embodiments, the coating material may include an alkylene ether containing polymer, such as PEG. In some embodiments, the coating material may include a polysaccharide, such as dextran. Like the charged moieties discussed above (e.g., anionic, cationic, and zwitterionic moieties), the hydrophilic coating agent can form strong hydrogen bonds with water molecules such that the resulting water of hydration acts as a layer (or "shield") that separates the biological micro-objects from interactions with non-biological molecules (e.g., the silicon and/or silicon oxide of the substrate).

Further details of appropriate coating treatments and modifications may be found at U.S. application Ser. No. 15/135,707, filed on Apr. 22, 2016, and is incorporated by reference in its entirety.

H. Additional System Components for Maintenance of Viability of Cells within the Sequestration Chambers of the Microfluidic Device.

In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells.

IV. Additional Embodiments

A. Embodiments Using T or NK Cells

In certain instances, T cells may be present in the dissociated cell sample. In such instances, the method may further comprise performing a selection on the dissociated cell sample to isolate a fraction that has a greater percentage or concentration of T cells than the original dissociated sample. In this manner, tumor-infiltrating lymphocytes (TILs) can be obtained from the same patient's tumor sample. In other instances, T cells can be obtained from the same patient's blood. For example, T cells can be selected from a blood sample (or peripheral blood mononuclear cell (PBMC) sample) obtained from the same patient. In still other instances, T cells can be obtained from a subject that is not the patient providing the at least one solid tumor (e.g., a subject that is a blood donor or tissue donor). T cells may be separated from other cells in a dissociated cell sample or a blood/PBMC sample by using at least one T cell marker chosen from CD4, CD8, CD25, CD45RA, CD45RO, CD62L, CD69, and CD3. Regardless of the origin of the T cells or the selection procedure used (if any), the resulting T cells may be cloned and/or used in the methods disclosed herein. For example, the T cells (whether patient-specific or donor-derived) may be used to prepare CAR-T therapeutics or used for other types of immunotherapy, such as combination therapy involving TILs and another therapeutic agent (e.g., an antibody prepared according to the methods disclosed herein).

Similar to T cells, natural killer (NK) cells can be used in the methods disclosed herein. For example, NK cells can be used to prepare CAR therapeutics, as described in Topfer et al. (2015), J. Immunol. 194(7):3201-3212. The NK cells can be obtained, for example, from a blood sample or a tissue sample (e.g., a dissociated cell sample obtained from a tumor). The NK cells can be isolated from other cells in the sample by using at least one NK marker, such as CD56.

B. Embodiments Relying on Outside Cell Sources

In some embodiments, all of the cell sources are from a single patient. In other embodiments, such as those discussed in this subsection, the cell sources may be from different patients or different sources. In one aspect, the method comprises using a microfluidic device to identify at least one B cell that produces antibodies capable of binding to both the patient's cancer cells and cancer cells from another source (e.g., in a two-step process). In one embodiment, the B cells are tested against a cancer cell line while the patient's own cancer cells are prepared and/or cultured (e.g., before the patient's cancer cells are loaded onto the microfluidic device). T cells or NK cells may also be obtained from the same patient or from a different source.

C. Embodiments Employing Normal Cells

When desired, the specificity of the antibodies produced by the B cells can be evaluated by comparing their ability to bind both cancer and non-cancer cells (i.e., normal cells). As such, optionally, the method may further comprise using a microfluidic device to identify whether the antibodies produced by the B cell are capable of binding to non-cancer cells. The non-cancer cells and the cancer cells may be dissociated from the same tumor sample. Alternatively, the non-cancer cells and/or the cancer cells may originate from a subject other than the patient providing the at least one solid tumor sample.

The same microfluidic device may be used to identify binding of the antibodies to cancer and non-cancer cells. The cancer and non-cancer cells may be loaded into different parts of the microfluidic device. For example, cancer cells (or non-cancer cells) can be placed into the same isolation chamber as a B cell, and non-cancer cells (or cancer cells) can be flowed into the flow channel to a location proximal to where the isolation chamber opens into the flow channel. In another example, cancer cells (or non-cancer cells) can be placed into an isolation chamber that is adjacent to an isolation chamber that contains a B cell, and non-cancer cells (or cancer cells) can be flowed into the flow channel to a location proximal to where the isolation chamber that contains the B cell opens into the flow channel. In still another example, cancer cells (or non-cancer cells) can be placed into an isolation chamber along with a B cell, and non-cancer cells (or cancer cells) can be placed into an isolation chamber that is adjacent to the isolation chamber that contains the B cell. Regardless of the placement of the cancer cells and/or the non-cancer cells, the same microfluidic device can be used to simultaneous assess whether antibodies (e.g., such as produced by a B cell) bind to cancer cells and/or non-cancer cells. In other embodiments, the cancer and non-cancer cells may be loaded sequentially in the same flow path (or the same isolation region), allowing for the sequential detection of binding between (1) the antibodies and the cancer cells and (2) the antibodies and the non-cancer cells.

V. Methods of Treatment and Therapeutic Compositions

Patients having cancer may be treated with an antibody or fragment thereof produced by the methods described herein. In one instance, the tumor sample is taken from the same patient who is treated. One advantage of this method is that personalized treatment can be designed for a given patient and in some instances that personalized treatment can be prepared in a relatively short window of time, allowing for therapeutic efficacy in the time required by the patient's disease state. For instance, in some embodiments, the time from obtaining the tumor sample to treatment may be at most about 2 months.

Once the variable heavy and light chain regions of the antibody produced by the B cell have been determined, a variety of different antibody or antibody fragment constructs may be prepared, either containing all or some of the variable sequences. In some instances, the patient may be treated with a single chain antibody. In other instances, the patient may be treated with an antibody or fragment thereof that has two heavy chains and two light chains. In some embodiments an engineered antibody construct comprises Fab or Fab'(2) fragments, scFvs, multivalent scFvs (e.g., diabodies or tribodies), minibodies (e.g., scFv-CH3 dimers), bispecific Abs, or camel variable functional heavy chain domains.

In other embodiments an engineered antibody construct comprises any variant of the antibody identified by the methods herein. In some embodiments, the antibody or fragment may be administered in isolated form.

For example, an engineered antibody construct may comprise (a) at least the heavy chain CDRs of an antibody identified by the method herein; (b) at least the heavy and light chain CDRs of an antibody identified by the method herein; (c) at least the heavy chain variable region of an antibody identified by the method herein; or (d) at least the heavy and light chain variable regions of an antibody identified by the method herein.

In other instances, various constructs may be prepared using the antibody or fragment. For instance, the antibody may be displayed on an engineered T cell or an engineered NK cell. In some embodiments, the engineered T cell is a chimeric antigen receptor T cell. The T cell may be obtained from the same patient prior to being engineered to display the antibody, such as, for instance from the patient's tumor sample or a blood sample obtained from the patient. Such a T cell may be genetically engineered to express the antibody or fragment thereof. Similarly, in other embodiments, the engineered NK cell is a chimeric antigen receptor NK cell. The NK cell may be obtained from the same patient prior to be engineered to display the antibody, such as, for instance, from the patient's tumor sample or a blood sample obtained from the patient. Such a NK cell may be genetically engineered to express the antibody or fragment thereof.

In some modes, the antibody or fragment thereof may be administered in combination with another therapy. In such a case, the combination therapy may be surgery, radiation, chemotherapy, CAR-T therapy, T cell therapy (such as by simply amplifying the patients own T cells, such as TILs, and reintroducing them), other immunotherapy (by targeting known antigens that inhibit T cell function with function-blocking antibodies, such as inhibitory antibodies against PD-1, PD-L1, CTLA-4, LAG-3, TIM-3, VISTA, BTLA, or any combination thereof), or administration of an immune stimulatory agent, such as ICOS, OX40, 41BB, an anti-tumor vaccine, cytokines, or a tumor-specific virus.

VI. Methods of Labeling and Detection

Antibodies produced according to the methods herein may also be used in methods of detection. For example, the antibodies may be labeled with a detectable label and used in vivo or in vitro to detect or label cancer cells (including the patient's own tumor cells). For example, fluorescence guided surgery may be performed using a fluorophore-conjugated antibody in order to highlight the tumor, improve surgical resection, and increase survival rates. Fluorophores such as Alexa Fluor 488 may be used. The antibody-fluorophore conjugate may be injected intravenously or it may be applied to the resection surfaces during surgery. The antibodies produced herein may also be used for other methods of detection or labeling.

EXAMPLES

Example 1. Processing of Tumor Biopsy and Fragmentation of Dissociated Cell Sample A. Dissociation of Tumor Sample A tumor sample is obtained from a patient having a surgical resection of his or her tumor. On the day of tumor resection, the specimen is received in the laboratory immediately following the procedure. The specimen is bathed in sterile saline in a sterile container. Viable tumor tissue is dissected away from non-viable tissue and healthy (non-cancer) tissue in a laminar flow hood using a scalpel and sterile forceps. Other samples of viable tumor tissue may be obtained for other assessments. The tumor sample for dissociation is weighed and kept in a 50 ml centrifuge tube containing a small amount of sterile HBSS. A medium for culturing cells is prepared by supplementing RPMI 1640 with 10% human serum (heat inactivated at 56° C. for 30 minutes), and with final concentrations of penicillin G (100 units/ml), streptomycin (100 µg/ml), gentamicin (50 µg/ml), Hepes (25 mM), and 2-mercaptoethanol ($5.5 \times 10^{-5}$ M).

The tissue specimen is placed on a sterile cutting surface (cutting board or open Petri dish). Using sterile scalpel and forceps, the specimen is cut into small (3-5 mm) fragments. Cut fragments are transferred into a gentleMACS® C Tube. Enzyme medium (EM) is added to the tube (5 ml for 0.2-2 g of tissue and 10 ml for 2-5 g) and the tube is securely closed by turning the cap until a slight click is heard. EM is used to help disperse cells from the surgical specimen during the short incubation periods between the gentleMACS® program runs. The enzyme-containing medium, RPMI 1640, does not contain serum, but contains penicillin G (100 units/ml), streptomycin (100 µg/ml), gentamicin (50 µg/ml), Fungizone® (1.25 µg/ml), collagenase (1 mg/ml), and Pulmozyme® (~30 units/ml). Enzyme stocks are dry powders stored at −20° C.

The C Tubes are installed vertically and cap-side down into the gentleMACs Sleeve. Proper installation ensures that the C Tubes are held in position against rotational and axial forces. Pre-defined programs are provided by the internal gentleMACS® dissociator memory. The programs vary in intensity, so an appropriate program is selected depending on the texture of the tissues to be processed. Softer tissues require more gentle rotation (lower speed) and harder tissues require a more vigorous, longer rotation. Multiple dissociation runs may be performed with evaluation of the state of dissociation being performed between runs. Dissociated tissue is filtered through an autoclaved wire mesh placed in an autoclaved funnel on top of a 250 ml centrifuge tube. The wire mesh is rinsed with sterile HBSS and the tube filed with additional sterile HBSS. The dissociated tissue is then washed one time by centrifuging 10 minutes at 1500 rpm. The supernatant is aspirated and the pellet resuspended in a known volume of HBSS.

B. An Alternative Procedure for Tumor Dissociation

As an alternative to performing tumor dissociation using the gentleMACS® instrument, a digestion buffer may be used. Tumor tissue is teased apart using forceps or cut into small pieces (2-5 mm). Tissue is placed in a dissociation buffer (100 units/ml collagenase and 100 µg/ml DNase in RPMI and 10% human serum (heat inactivated at 56° C. for 30 minutes)). The digestion proceeds in an incubator at 37° C. for 30 minutes. After incubation, the sample is pipetted up and down with a pipette to get an easily flowing single cell suspension.

The suspension is filtered through a 70 micron filter and washed 2× with MACs separation buffer supplemented with 10% human serum (heat inactivated at 56° C. for 30 minutes). The cell suspension is centrifuged at 400×g for 10 minutes. The pellet is rinsed with 10 ml MACs buffer and centrifuged again at the same setting. The dissociated cells are then resuspended in 100 µl MACs buffer.

C. Fragmentation of Cell Types from Dissociated Cell Sample

After a dissociated cell sample comprising single cells is prepared using either protocol above, B cells, T cells, NK cells, and cancer cells may be fragmented from the dissociated cell sample. Anti-CD20 magnetic beads may be used to select for B cells. Anti-CD4 and/or anti-CD8 magnetic beads may be used to select for T cells. Anti-CD56 magnetic beads may be used to select for NK cells. Magnetic beads attached to an antibody specific for the cancer cells may be used to select for cancer cells or cancer cells may be removed manually using morphological evaluations.

Antibody labeled microbeads targeting the first cell type to be fragmented (approximately 10 μl per $10^8$ cells) are added to the dissociated cell sample. The tube is mixed well by gentle flicking of the tube and incubating for 15 minutes at 4-8° C., shielded from light. The cells are washed by adding 10 ml of MACs buffer and centrifuging at 400×g for 10 minutes. The supernatant is poured (or aspirated) off and the cells resuspended in 500 μl MACs buffer. A fresh column is applied to the magnet separator. The column is primed by rinsing with an appropriate amount of MACs buffer for the column selected. After priming the column, the cell suspension is applied to the top of the column, with one column used for every $1\times10^8$ cells. Any unlabeled cells (passthrough) are collected and reserved for isolation of different cell types. For a first wash, the column is washed for a minimum of three and up to five times with a 500 μl volume for a total of 1.5 to 2.5 ml of fluid wash. Fluid flow is preserved in the column without it being allowed to run dry, which can impact purity and lead to loss of cell viability).

For a second wash, the column is washed with a dissociation buffer mix comprising collagenase and DNase in order to flush out sticky debris from dead or dying tumor cells (100 units/ml Collegenase and 100 μg/ml DNase in RPMI and 10% human serum (heat inactivated at 56° C. for 30 minutes)). For a third wash, the MACs buffer is used again until the wash looks completely clear.

The column is removed from the magnetic separator and placed on a suitable collection tube. 2 ml of buffer is placed on the column and the magnetically labeled cells are collected by firmly applying the plunger supplied with the column.

Alternatively, magnetic separation may be conducted by AutoMACS®.

Additional separation steps are performed to isolate each of the B cells, T cells, NK cells, and cancer cells. Magnetic beads are removed from the cells, when desired.

Example 2. Screening Mouse Splenocytes for Secretion of IgG Antibodies in a Microfluidic Device A screen was performed to identify mouse splenocytes that secrete IgG-type antibodies that bind to human CD45. The experimental design included the following steps:
1. Generation of CD45 antigen coated beads;
2. Harvest mouse splenocytes;
3. Load cells into a microfluidic device; and
4. Assay for antigen specificity.

Reagents used for the experiment included those shown in Table 1.

TABLE 1

| | Reagents | | | |
|---|---|---|---|---|
| | Name | Vendor | Catalog Number | Lot Number |
| 1 | Slide-A-Lyzer MINI Dialysis Device, 7K MWCO, 0.1 mL | Thermo Pierce | 69560 | OJ189254 |
| 2 | CD45 Protein | R&D Systems | 1430-CD | 112722 |
| 3 | PBS pH 7.2 with Mg2+ and Ca2+ | Fisher | BP29404 | |
| 4 | Streptavidin Coated Beads (8 μm) | Spherotech | SVP-60-5 | AC01 |
| 5 | EZ-Link NHS-PEG4-Biotin, No-Weigh Format | Pierce | 21329 | |
| 6 | Hybridoma SFM Media | Life Tech | 12045-076 | |
| 7 | Fetal Bovine Serum | Hyclone | #SH30084.03 | |
| 8 | Penicillin-Streptomycin (10,000 U/mL) | Life | 15140-122 | |
| 9 | Goat anti-mouse F(ab')2-Alexa 568 | Life | Cat# A11019 | Lot#1073003 |
| 10 | streptavidin-488 | Life | Catalog #S32354 | Lot #1078760 |
| 11 | Mouse anti CD45 IgG$_1$ | R&D Systems | MAB1430 | ILP0612061 |
| 12 | BD Falcon ™ Cell Strainers, 40 μm, Blue | BD | 352340 | |

Generation of CD45 Antigen Coated Beads

CD45 antigen coated microbeads were generated in the following manner:
- 50 g carrier free CD45 was resuspended in 500 µL PBS (pH 7.2).
- A slide-a-lyzer mini cup was rinsed with 500 µL PBS, then added to a microfuge tube.
- 50 µL of the 0.1 µg/µL CD45 solution was added to the rinsed slide-a-lyzer mini cup.
- 170 µL PBS was added to 2 mg of NHS-PEG4-Biotin, after which 4.1 µL of NHS-PEG4-Biotin was added to the slide-a-lyzer mini cup containing the CD45 antigen.
- The NGS-PEG4-Biotin was incubated with the CD45 antigen for 1 hour at room temperature.
- Following the incubation, the slide-a-lyser mini cup was removed from the microfuge tube, placed into 1.3 mls PBS (pH 7.2) in a second microfuge tube, and incubated at 4° C. with rocking, for a first 1 hour period. The slide-a-lyser mini cup was subsequently transferred to a third microfuge tube containing 1.3 mls of fresh PBS (pH 7.2), and incubated at 4° C. with rocking, for a second 1 hour period. This last step was repeated three more times, for a total of five 1 hour incubations.
- 100 µL of biotinylated CD45 solution (~50 ng/µL) was pipetted into labeled tubes.
- 500 µL Spherotech streptavidin coated beads were pipetted into a microfuge tube, washed 3 times (1000 µL/wash) in PBS (pH 7.4), then centrifuges for 5 min at 3000 RCF.
- The beads were resuspended in 500 µl PBS (pH 7.4), resulting in a bead concentration of 5 mg/ml.
- 50 µL biotinylated protein was mixed with the resuspended Spherotech streptavidin coated beads. The mixture was incubated at 4° C., with rocking, for 2 hours, then centrifuged 4° for 5 min at 3000 RCF. The supernatant was discarded and the CD45 coated beads were washed 3 times in 1 mL PBS (pH 7.4). The beads were then centrifuges at 4° C. for another 5 min at 3000 RCF. Finally, the CD45 beads were resuspended in 500 µL PBS pH 7.4 and stored at 4° C.

Mouse Splenocyte Harvest

The spleen from a mouse immunized with CD45 was harvested and placed into DMEM media+10% FBS. Scissors were used to mince the spleen.

Minced spleen was placed into a 40 µm cell strainer. Single cells were washed through the cell strainer with a 10 ml pipette. A glass rod was used to break up the spleen further and force single cells through the cell strainer, after which single cells were again washed through the cell strainer with a 10 ml pipette.

Red blood cells were lysed with a commercial kit.

Cells were spun down at 200×G and raw splenocytes were resuspended in DMEM media+10% FBS with 10 ml pipette at a concentration of $2e^8$ cells/ml.

Loading Cells into Microfluidic Device

Splenocytes were imported into the microfluidic chip and loaded into pens containing 20-30 cells per pen. 100 microliters of media was flowed through the device at 1 µL/s to remove unwanted cells. Temperature was set to 36° C., and culture media was perfused for 30 minutes at 0.1 µL/sec.

Antigen Specificity Assay

Cell media containing 1:2500 goat anti-mouse F(ab')2-Alexa 568 was prepared.

100 µL of CD45 beads were re-suspend in 22 µL of the cell media containing the 1:2500 dilution of goat anti-mouse F(ab')2-Alexa 568.

The resuspended CD45 beads were next flowed into the main channel of the microfluidic chip at a rate of 1 µL/sec until they were located adjacent to, but just outside the pens containing splenocytes. Fluid flow was then stopped.

The microfluidic chip was then imaged in bright field to determine the location of the beads.

Next, a Texas Red Filter was used to capture images of the cells and beads. Images were taken every 5 minutes for 1 hr, with each exposure lasting 1000 ms and a gain of 5.

Results

Figures 5A, 5B, 5C:
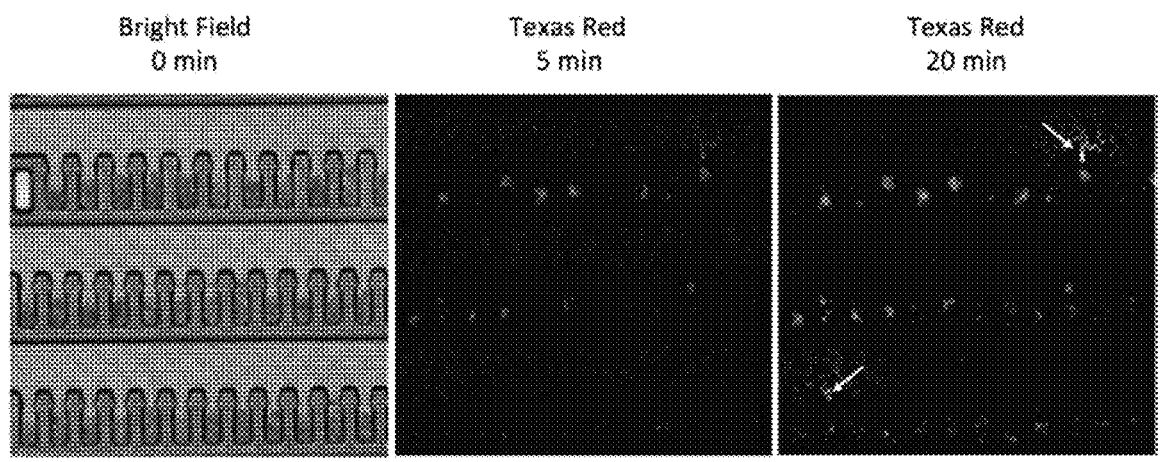
FIGS. 5A-5C depict a microfluidic device comprising a plurality of microfluidic channels, each fluidically connected with a plurality of sequestration chambers. Each sequestration chamber contains a plurality of mouse spenocytes.

Positive signal was observed developing on the beads, reflecting the diffusion of IgG-isotype antibodies diffusing out of certain pens and into the main channel, where they were able to bind the CD45-coated beads. Binding of anti-CD45 antibody to the beads allowed for the secondary goat anti-mouse IgG-568 to associate with the beads and produce a detectable signal. See FIG. 5C, white arrows.

Using the methods disclosed herein, each group of splenocytes associated with positive signal could be separated and moved into new pens as a single cell and reassayed. In this manner, single cells expressing anti-CD45 IgG antibodies could be detected.

Example 3. Membrane Preparation and Conjugation of Membrane Antigens to Beads

The following protocol demonstrates the feasibility of obtaining samples containing proteins (and other biomolecules), and particularly membrane bound or membrane associated proteins, from samples cells of interest. The protocol is performed on Jurkat cells to enable testing of the resulting samples for proteins known to be present in such cells. The protocol could be readily extended to other cell types, including cancer cells isolated from a tumor biopsy, thereby yielding samples containing tumor cell-specific (or other cell type-specific) antigens useful for screening immunological cells (such as B cells) for their reactivity to the antigens.

Materials:
- Jurkat cells (ATCC TIB-152)
- LiDS-Sample Buffer: 0.02 g/mL LiDS, 10% glycerol, 0.51 mM EDTA, 247 mM Tris, pH8.5 (ThermoFisher B0008)
- Qiashredder (Qiagen 79654)
- DPBS (containing calcium and magnesium, ThermoFisher 14040-182)
- UltraPure Water (ThermoFisher 10977-015)
- EZ-Link Sulfo-NHS-SS-Biotin (ThermoFisher 21328): store at −20° C., take out and warm at RT 30 min before use; spin down briefly to collect everything at the bottom of the tube; immediately before use, add 164 µL ultrapure water to 1 tube containing 1 mg Sulfo-NHS-SS-Biotin and pipette up and down several times to dissolve (results in a 10 mM solution)
- Complete Ultra mini (Sigma 5892791001): Prepare 20× solution: dissolve 1 tablet in 500 µL water by vortexing (stable for 4 weeks at 4° C. or −20° C.)
- Minute Plasma Membrane Protein Isolation Kit (Invent Biotechnologies SM-005): Before use, thaw Solutions A and B, and add protease inhibitors:
  - for each sample 500 µL Buffer A+25 µL 20× protease inhibitors (store on ice)
  - for each sample 200 µL Buffer B+10 µL 20× protease inhibitor (store on ice)
  - prepare 1 filter cartridge for each sample on ice
- BSA: Chromatopur Bovine Albumin (MP Biomedicals 02180561)

Figure 6:
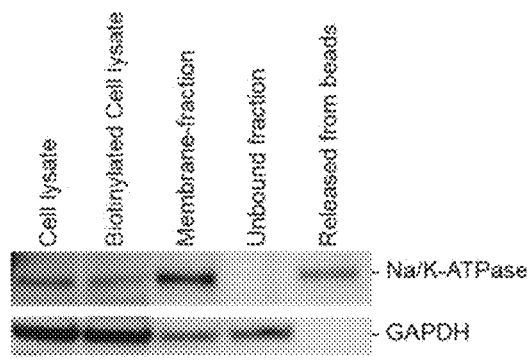
FIG. 6 shows a Western blot of various fractions from Jurkat cells.
Figure 7:
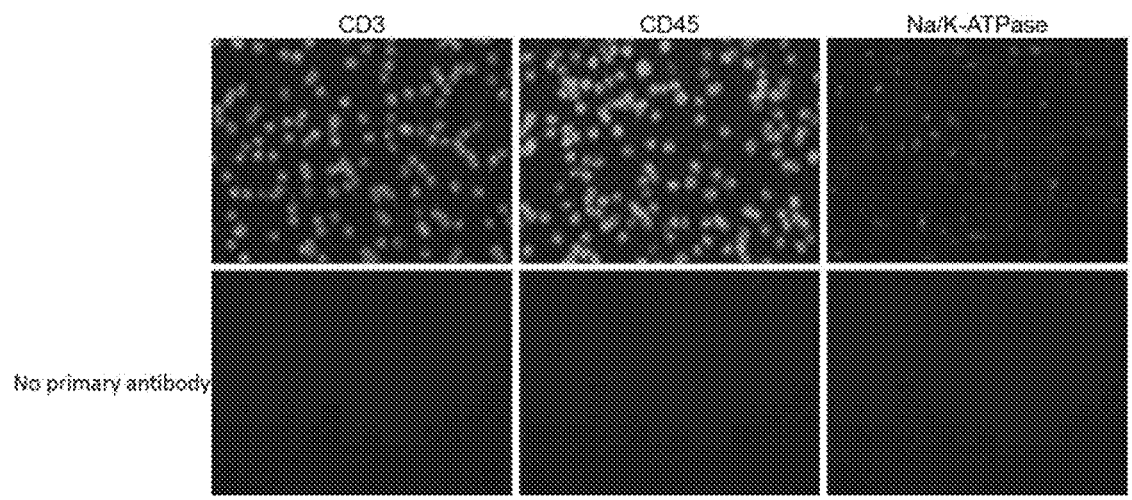
FIG. 7 shows beads coated with Jurkat cell membrane fractions stained with anti-CD3, anti-CD45 or anti-Na/K-ATPase antibodies.
Figure 8:
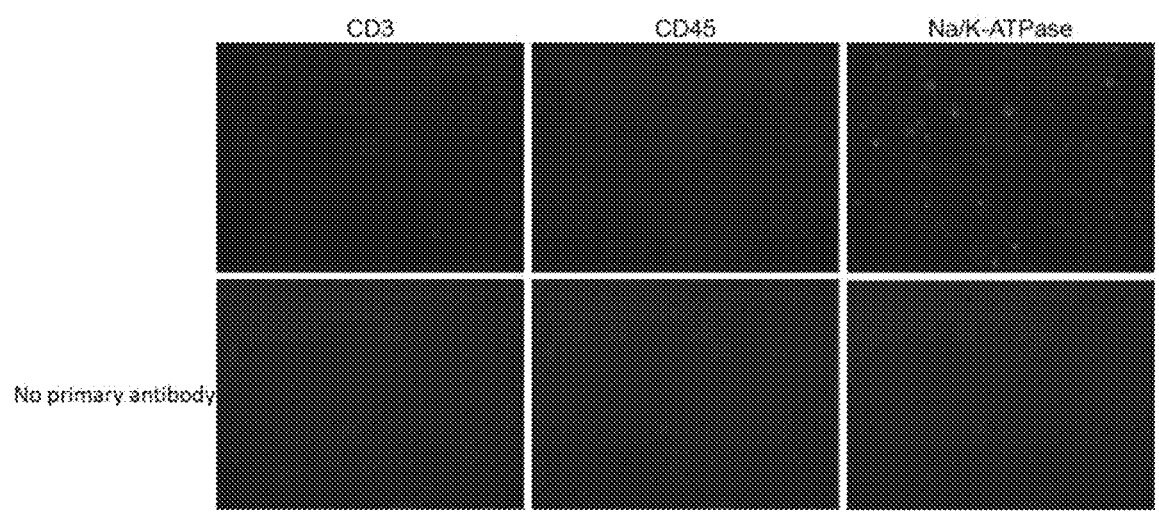
FIG. 8 shows beads coated with HEK293 cells stained with the same antibodies as in FIG. 7.

Streptavidin coated magnetic microspheres (Bangs Laboratories CM01N Lot #11806), wash and block before use:
  Vortex beads, take out 300 μL/sample and transfer into 1.5 mL tube
  Wash with PBS
  Resuspend in 0.5% BSA and incubate at 4° C. (rotating) for at least 1 h
  Wash with PBS, resuspend in 500 μL DPBS (+ protease inhibitors)/sample
  Anti-alpha 1 Sodium Potassium ATPase (Na/K-ATPase) antibody (Abcam ab7671)
  Anti-human CD3 antibody, clone SK7 (BioLegend 344802)
  Anti-human CD45 antibody, clone HI30 (BioLegend 304002)
  F(ab')2-Goat anti-Mouse IgG (H+L), Alexa Fluor 488 (ThermoFisher A-11017)
Biotinylation of Membrane Proteins:
  Count Jurkat cells
  Prepare an aliquot for Western Blot analysis:
    centrifuge 2×106 cells
    wash with PBS
    lyse in LiDS-Sample Buffer and centrifuge through a Qiashredder column to shear DNA
    store at 4° C. for a few days, longer at −80° C.
  Wash multiples of 15×10⁶ cells three times with DPBS by centrifugation
  Resuspend each pellet in 500 μL DPBS, transfer into a 1.5 mL tube and add 10 μL of freshly prepared 10 mM Sulfo-NHS-SS-Biotin
  Rotate 30 min at RT
  Wash three times with cold DPBS and proceed with cell pellets to enrich the membrane fractions
  Process 1 sample for Western Blot analysis (see above).
FIG. 6 shows an exemplary Western blot stained for Na/K-ATPase, a protein present in the plasma membrane, and GAPDH, a cytosolic protein.
Enrichment of the Membrane Fraction using Minute Plasma Membrane Isolation Kit:
  Perform all steps on ice, centrifuge at 4° C.
  Resuspend pellets in Buffer A: 200 for <5×106 cells, 500 for >5×106 cells
  Incubate on ice for 10 min
  Vortex vigorously for 10-30 sec, immediately transfer to the filter cartridge on ice
  Cap the filter cartridge, centrifuge 30 sec at 16,000 g (increase to 2 min if cell lysate does not go through)
  Resuspend the pellet in collection tube, transfer to the same filter and centrifuge again
  Discard filter, resuspend pellet by vigorously vortexing for 10 sec
  Centrifuge 1 min at 700 g (to pellet intact nuclei)
  Centrifuge supernatant in a fresh 1.5 ml tube 30 min at 16,000 g/4° C. (→supernatant contains cytosol, pellet=total membrane protein fraction)
  Resuspend pellet in 200 μl buffer B by vortexing, or pipetting up and down
  Centrifuge 20 min at 7,800 g/4° C.→pellet contains organelle membrane proteins
  Carefully transfer supernatant (membrane fraction) into a fresh 2.0 ml tube
Bind Membrane Fractions to Streptavidin-Coated Magnetic Microspheres:
  Add 80 μL of each membrane fraction to 500 μL beads
  Rotate o/n at 4° C.
  Save unbound fraction for analysis by Western Blot
  Rotate 30 min in 0.5% BSA/PBS+ protease inhibitors
  Wash with PBS
  Resuspend in 250 μL 0.1% BSA/PBS+ protease inhibitors
Release Membrane Fractions from Beads (cleave S—S bond using DTT):
  Take out an aliquot of 50 μL beads
  put on magnet and remove solution
  Resuspend beads in 50 μL LiDS-Sample Buffer containing 50 mM DTT (1× Reducing Agent, ThermoFisher B0009)
  Incubate 2 hr at RT (mix every ~30 min)
Antibody Staining:
  Take 50 μL aliquots of beads (from step 24) for each antibody in following dilutions
    CD3 (1:200)
    CD45 (1:100)
    Na/K-ATPase (1:100)
    No primary antibody
  Rotate 30 min at 4° C.
  Add 800 μL PBS to wash, wash 1× additionally with PBS
  Incubate in secondary antibody (Alexa488-conjugated goat anti-mouse) for 30 min at 4° C. (rotating, volume: 200 μL in 0.5% BSA/PBS+ protease inhibitors) 1:300
  Add 800 μL PBS to wash, wash 1× additionally with PBS
  Resuspend in 20 μL 0.5% BSA/PBS+ protease inhibitors
  Image on fluorescence microscope FIG. 7 shows beads coated with a Jurkat cell membrane fraction stained for CD3, CD45 or Na/K-ATPase. CD3 and CD45 are both strongly represented compared with NA/K-ATPase, which appears as fainter spots. FIG. 8 shows a comparison with HEK293 cells. Here Na/K-ATPase stains the same, but CD3 and CD45 are absent.

The results demonstrate that proteins isolated from cell membrane preparations can be successfully coupled to beads. Such beads could be mixed with immunological cells to determine which cells are reactive to antigens (whether protein or otherwise) present in the cell membrane preparations.

Example 4. Identifying B Cells that Express Antibodies that Bind to Bead-Conjugated Cancer Cell-Derived Antigens A screen can be performed to identify patient-specific B cells that express antibodies that bind to a patient's own medullary breast cancer cells. The experimental design can include the following steps:
  Harvest and selection of B cells and cancer cells;
  Obtain cell membrane preparations from the cancer cells and conjugate the membrane antigens to beads;
  Load B cells into a microfluidic device;
  Load beads conjugated to cancer cell-derived membrane antigens into the microfluidic device; and
  Assay for binding of antibodies produced by B cells to the beads.

A. Cell Harvest and Selection

A biopsy of a medullary breast cancer tumor is obtained from a patient and the cells of the biopsy are dissociated, as described in Example 1 (above). B cells are selected from the resulting dissociated cell sample using anti-CD-20 magnetic beads, thereby producing a B cell-enriched cell sample. Cells remaining in the B cell-depleted dissociated cell sample are next depleted of non-medullary breast cancer cells using a mixture of anti-ER (estrogen receptor), anti-PR (progesterone receptor), and anti-HER2 magnetic beads to produce a triple-negative breast cancer cell-enriched sample.

B. Preparation of Cell Membrane from Breast Cancer Cells and Conjugation of the Membrane Antigens to Beads Starting with the triple-negative breast cancer cell-enriched sample obtained in part A, cell membranes from the cancer cells can be prepared and conjugated to beads, as described in 3, above.

C. Loading Cells into Microfluidic Device

The B cell-enriched cell sample is next loaded into a microfluidic chip by flowing 1-3 microliters of the sample into a flow channel at a rate of 0.1-1.0 microliters/sec. The flow of sample is then stopped and, while the cells in the sample are located in the flow channel, B cells are selectively captured using DEP force (e.g., OET) and moved into the isolation regions of isolation chambers connected to the flow channel. A single B cell is placed into each of a plurality of isolation chambers. Depending on the size of the microfluidic chip used, 3000 or more B cells can be individually isolated on a single chip. In general, fewer B cells are expected to be present in the sample. As a result, all B cells in the sample can be isolated. Once the B cells are moved into the isolation chambers, the flow channel is flushed with fresh medium to clear the flow channel of unwanted cells and debris.

After clearing the flow channel, the triple-negative breast cancer cell-enriched sample is loaded into the chip. Similar to the B cell-enriched sample, 1-3 microliters of the cancer cell-enriched sample is flowed into the flow channel at a rate of 0.1-1.0 microliters/sec, then the flow is stopped. Using morphological traits, a plurality of cancer cells (e.g., 3-6) is selected using DEP force (e.g., OET) and moved into each isolation chamber that contains a B cell. Once the cancer cells are moved into the isolation chambers, the flow channel is flushed with fresh medium to clear the flow channel of unwanted cells and debris. In this manner, a plurality of isolation chambers in the microfluidic chip are loaded with a single B cell and a plurality of medullary breast cancer cells.

D. Loading Beads into the Microfluidic Device

After clearing the flow channel, the beads conjugated to the membrane antigens obtained from the triple-negative breast cancer cell-enriched sample are loaded into the chip. Similar to the B cell-enriched sample, 1-3 microliters of the cancer cell-associated antigen-conjugated beads are flowed into the flow channel at a rate of 0.1-1.0 microliters/sec, then the flow is stopped. The beads are moved into each isolation chamber that contains a B cell. Once the beads are moved into the isolation chambers, the flow channel is subsequently flushed with fresh medium to clear the flow channel of unwanted beads and debris. In this manner, a plurality of isolation chambers in the microfluidic chip are loaded with a single B cell and a plurality of cancer cell-associated antigen-conjugated beads. Alternatively, the beads can be left in the channel, as described in Example 2, above.

E. Antibody Binding Assay

To determine whether any of the isolated B cells are producing antibodies that bind to the cancer cell-associated antigens, the B cells in the microfluidic chip are incubated under conditions conducive to antibody expression. After such incubation, a medium containing a mixture of secondary antibodies that bind to the constant region of human antibodies is flowed into the microfluidic chip, then stopped. Antibodies in the antibody mixture, which can contain fluorescently labeled anti-human IgG antibodies, anti-human IgM antibodies, and optionally antibodies against human IgA, IgE, and/or IgD, are allowed to diffuse into the isolation chambers and bind to antibodies produced by the B cells. If the antibodies produced by a B cell binds to one or more of the cancer cell-associated antigens that are conjugated to the beads in the corresponding isolation chamber, then the anti-human secondary antibodies (and their labels) will become detectably bound to the surface of the beads. If the beads are left in the channel, then the fluorescently labeled secondary antibodies can be mixed with the beads before the beads are flowed into the microfluidic device.

During the secondary antibody incubation step, the microfluidic chip is periodically imaged using a filter for detection of fluorescent signal (e.g., a Texas Red Filter). Images can be taken every 5 minutes for 1 hr, with each exposure lasting 1000 ms.

F. Results

Positive signal can be observed developing on the surface of the beads in (or proximal to) any isolation chamber that contains a B cell that expresses antibodies that bind to the cancer cell-associated antigens. Using this method, individual B cells expressing antibodies of interest can be specifically identified. B cells that do not produce any interesting antibodies can be moved out of their isolation chambers and exported out of the microfluidic chip to waste. B cells identified as expressing an antibody that binds to the patient's medullary breast cancer cell-derived antigens can be moved out of the isolation chamber (e.g., using DEP force, such as OET) and exported for amplification and sequencing of the heavy and light chain variable regions of the expressed antibodies. If the B cells expanded while being induced to express antibodies, a clonal population of B cells can be exported for amplification and sequencing of the heavy and light chain variable regions of the expressed antibodies.

Example 5. Identifying B Cells that Express Antibodies that Bind to the Cancer Cells Alternatively, the screen can be performed to identify patient-specific B cells that express antibodies that bind to a patient's own medullary breast cancer cells. The experimental design can include the following steps:

Harvest and selection of B cells and cancer cells;
Load cells into a microfluidic device; and
Assay for binding of antibodies produced by B cells to cancer cells.

A. Cell Harvest and Selection

A biopsy of a medullary breast cancer tumor is obtained from a patient and the cells of the biopsy are dissociated, as described in Example 1 (above). B cells are selected from the resulting dissociated cell sample using anti-CD-20 magnetic beads, thereby producing a B cell-enriched cell sample. Cells remaining in the B cell-depleted dissociated cell sample are next depleted of non-medullary breast cancer cells using a mixture of anti-ER (estrogen receptor), anti-PR (progesterone receptor), and anti-HER2 magnetic beads to produce a triple-negative breast cancer cell-enriched sample.

B. Loading Cells into Microfluidic Device

The B cell-enriched cell sample is next loaded into a microfluidic chip by flowing 1-3 microliters of the sample into a flow channel at a rate of 0.1-1.0 microliters/sec. The flow of sample is then stopped and, while the cells in the sample are located in the flow channel, B cells are selectively captured using DEP force (e.g., OET) and moved into the isolation regions of isolation chambers connected to the flow channel. A single B cell is placed into each of a plurality of isolation chambers. Depending on the size of the microfluidic chip used, 3000 or more B cells can be individually isolated on a single chip. In general, fewer B cells are expected to be present in the sample. As a result, all B cells in the sample can be isolated. Once the B cells are moved into the isolation chambers, the flow channel is flushed with fresh medium to clear the flow channel of unwanted cells and debris.

After clearing the flow channel, the triple-negative breast cancer cell-enriched sample is loaded into the chip. Similar to the B cell-enriched sample, 1-3 microliters of the cancer cell-enriched sample is flowed into the flow channel at a rate of 0.1-1.0 microliters/sec, then the flow is stopped. Using morphological traits, a plurality of cancer cells (e.g., 3-6) is selected using DEP force (e.g., OET) and moved into each isolation chamber that contains a B cell. Once the cancer cells are moved into the isolation chambers, the flow channel is flushed with fresh medium to clear the flow channel of unwanted cells and debris. In this manner, a plurality of isolation chambers in the microfluidic chip are loaded with a single B cell and a plurality of medullary breast cancer cells.

C. Antibody Binding Assay

To determine whether any of the isolated B cells are producing antibodies that bind to cancer cells, the B cells in the microfluidic chip are incubated under conditions conducive to antibody expression. After such incubation, a medium containing a mixture of secondary antibodies that bind to the constant region of human antibodies is flowed into the microfluidic chip, then stopped. Antibodies in the antibody mixture, which can contain fluorescently labeled anti-human IgG antibodies, anti-human IgM antibodies, and optionally antibodies against human IgA, IgE, and/or IgD, are allowed to diffuse into the isolation chambers and bind to antibodies produced by the B cells. If the antibodies produced by a B cell binds to one or more of the cancer cells in the corresponding isolation chamber, then the anti-human secondary antibodies (and their labels) will become detectably bound to the surface of the medullary breast cancer cells.

During the secondary antibody incubation step, the microfluidic chip is periodically imaged using a filter for detection of fluorescent signal (e.g., a Texas Red Filter). Images are taken every 5 minutes for 1 hr, with each exposure lasting 1000 ms.

D. Results

Positive signal can be observed developing on the surface of the cancer cells in any isolation chamber that contains a B cell that expresses antibodies that bind to the cancer cells. Using this method, individual B cells expressing antibodies of interest can be specifically identified. B cells that do not produce any interesting antibodies can be moved out of their isolation chambers and exported out of the microfluidic chip to waste. Each B cell identified as expressing an antibody that binds to the patient's medullary breast cancer cells can be moved out of the isolation chamber (e.g., using DEP force, such as OET) and exported for amplification and sequencing of the heavy and light chain variable regions of the expressed antibodies. If the B cells expanded while being induced to express antibodies, a clonal population of B cells can be exported for amplification and sequencing of the heavy and light chain variable regions of the expressed antibodies.

Example 6. Combination Therapy Using CAR-Ts and an Oncolytic Virus

Chimeric antigen receptor (CAR)-redirected T cells have the potential to provide increased benefits in cancer treatment. A patient having cancer, such as neuroblastoma, undergoes a biopsy or surgical resection and B cells producing antibodies that bind to the cancer are identified using the preceding examples. A CAR-T cell line is engineered to express antibodies or fragments thereof corresponding to the antibodies produced by the identified B cell (by corresponding, we mean having at least the same heavy chain CDRs, at least the same heavy and light chain CDRs, at least the variable heavy chain, or at least the variable heavy and light chain). For this patient, the CAR-T cell line is engineered to express an scFv, where the genes coding the variable regions of the heavy chain and light chain are cloned by RT-PCR. Combinatorial scFv genes are generated by splicing-by-overlap PCR and then ligated into restriction sites of a vector phage DNA.

The scFv sequence is cloned in frame into a retroviral backbone, such as the SFG retroviral backbone. A retroviral supernatant is prepared using 239T cells. Supernatant containing the retrovirus is collected 48 and 72 hours later. For transduction, $0.5 \times 10^6$/ml peripheral blood mononuclear cells (PBMCs) activated with OKT3 (Ortho Biotech, Bridgewater, NJ) and CD28 (Becton Dickinson, Mountain View, CA) antibodies and recombinant human IL-12 (100 units/ml; Proleukin, Chiron, Emeryville, CA) are plated in complete media (RPMI 1640 45%, Click medium 45%, and 10% heat-sterilized human serum and 2 mM L-glutamine) in 24-well plates pre-coated with a recombinant fibronectin fragment (FN CH-296, Retronectin, Takara Shuzo, Otsu, Japan). After the addition of viral supernatant, the cells are spun and incubated at 37° C. in 5% CO2. CAR expression on T lymphocytes is measured 72 hours later and the cells maintained in culture in complete media with the addition of rIL-2 (50 units/ml) every 3 days.

Such CAR-T cells are adoptively transferred to the patient along with administration of an oncolytic virus, such as an oncolytic adenovirus. The oncolytic adenovirus can be Ad5D24, optionally expressing recombinant IL15, RANTES, or the combination thereof. The patient is expected to have significant clinical improvement.

LISTING OF EXEMPLARY EMBODIMENTS

1. A method of preparing an antibody therapeutic, the method comprising: providing a dissociated cell sample from at least one solid tumor sample obtained from a patient; loading the dissociated cell sample into a microfluidic device having at least one flow region and at least one isolation region fluidically connected to the flow region; moving at least one B cell from the dissociated cell sample into at least one isolation region in the microfluidic device, thereby obtaining at least one isolated B cell; and identifying at least one isolated B cell that produces antibodies capable of binding to a cancer cell-associated antigen.

2. The method of embodiment 1, wherein said isolation region comprises at least one conditioned surface that promotes B cell lymphocyte viability, said conditioned surface comprising covalently linked molecules.

3. The method of embodiment 1, wherein said isolation region comprises a plurality of conditioned surfaces that promote B cell lymphocyte viability, each conditioned surface comprising covalently linked molecules.

4. The method of embodiment 2 or 3, wherein said at least one conditioned surface or each conditioned surface of said plurality comprises a layer of covalently linked hydrophilic molecules.

5. The method of embodiment 4, wherein said hydrophilic molecules are selected from the group of polymers comprising polyethylene glycol (PEG), polymers comprising amino acids, and combinations thereof.

6. The method of embodiment 1, wherein said isolation region comprises at least one surface coated with a coating material that promotes B cell viability.

7. The method of embodiment 1, wherein said isolation region comprises a plurality of surfaces each coated with a coating material that promotes B cell viability.

8. The method of embodiment 6 or 7, wherein said coating material comprises hydrophilic molecules.

9. The method of embodiment 8, wherein said hydrophilic molecules are selected from the group of polymers comprising polyethylene glycol (PEG), polymers comprising amino acids, and combinations thereof.

10. The method of any one of embodiments 1 to 9, wherein each of the at least one isolation region(s) forms a dead-end in the microfluidic device, and wherein, when the flow region is substantially filled with a flowing first fluidic medium and the isolation region(s) are substantially filled with a second fluidic medium: components of the second medium are able to diffuse into the first medium and components of the first medium are able to diffuse into the second medium; and there is substantially no flow of the first medium from the flow region into the isolation region.

11. The method of any one of embodiments 1 to 10, wherein the flow region of the microfluidic device comprises a microfluidic channel.

12. The method of embodiment 11, wherein each of the at least one isolation regions is part of a corresponding sequestration chamber, and wherein each sequestration chamber further comprises a connection region fluidically connecting the corresponding isolation region to the microfluidic channel.

13. The method of embodiment 12, wherein the connection region has a width $W_{con}$ of about 20 microns to about 60 microns.

14. The method of embodiment 12 or 13, wherein each of the at least one isolation region(s) has a width $W_{iso}$ that is greater than the width $W_{con}$ of the corresponding connection region.

15. The method of embodiment 14, wherein each of the at least one isolation region(s) has a width $W_{iso}$ that is about 50 microns to about 250 microns.

16. The method of any one of embodiments 12 to 15, wherein each of the sequestration chambers comprises a volume of about 0.5 nl to about 2.5 nl.

17. The method of any one of embodiments 1 to 16, wherein the at least one B cell is moved into the at least one isolation region using gravity and/or localized fluid flow.

18. The method of any one of embodiments 1 to 17, wherein the microfluidic device comprises a substrate having a DEP configuration.

19. The method of embodiment 18, wherein moving the at least one B cell into the at least one isolation region comprises using DEP force to move the at least one B cell.

20. The method of any one of embodiments 1 to 19, wherein prior to loading the dissociated cell sample, the method further comprises labeling B cells in the dissociated cell sample with a detectable marker.

21. The method of embodiment 20, wherein moving the at least one B cell into the at least one isolation region comprises selecting at least one B cell for movement based on detection of the detectable marker.

22. The method of any one of embodiments 1 to 21, wherein moving at least one B cell into at least one isolation region comprises moving a plurality of individual B cells into a corresponding plurality of separate isolation regions.

23. The method of any one of embodiments 1 to 22, further comprising: contacting the at least one B cell with a stimulating agent that stimulates B cell activation.

24. The method of embodiment 23, wherein the stimulating agent comprises a CD40 agonist.

25. The method of embodiment 24, wherein the CD40 agonist comprises CD40L, a derivative thereof, or an anti-CD40 antibody.

26. The method of embodiment 23, wherein the stimulating agent comprises one or more CD40L+ feeder cells.

27. The method of embodiment 26, wherein the one or more CD40L+ feeder cells is/are T cells or a derivative thereof.

28. The method of any one of embodiments 23 to 27, wherein the stimulating agent comprises a toll-like receptor (TLR) agonist.

29. The method of embodiment 28, wherein the TLR agonist is a CpG oligonucleotide.

30. The method of any one of embodiments 23 to 29, wherein the at least one B cell is contacted with the stimulating agent for a period of one to ten days.

31. The method of embodiment 30, wherein the at least one B cell is contacted with the stimulating agent substantially continuously for said period of one to ten days.

32. The method of any one of embodiments 23 to 31, further comprising: providing culture medium to the at least one B cell, wherein the culture medium comprises one or more growth-inducing agents that promote B cell expansion.

33. The method of embodiment 32, wherein the one or more growth-inducing agents include at least one agent selected from the group of IL-2, IL-4, IL-6, IL-10, IL-21, and BAFF.

34. The method of embodiment 32 or 33, wherein the provided culture medium comprises the stimulating agent.

35. The method of any one of embodiments 32 to 34, wherein the at least one B cell is provided culture medium for a period of one to ten days.

36. The method of any one of embodiments 32 to 35, wherein each B cell of the at least one isolated B cell(s) is cultured in the isolation region of the microfluidic device to a cell count of about 8 to 20 cells.

37. The method of any one of embodiments 32 to 36, wherein the steps of contacting the at least one B cell with the stimulating agent and providing culture medium to the at least one B cell are performed over a substantially coextensive period of time.

38. The method of any one of embodiments 23 to 37, wherein contacting the at least one B cell with the stimulating agent is performed prior to loading the dissociated cell sample into the microfluidic device.

39. The method of any one of embodiments 23 to 38, wherein contacting the at least one B cell with the stimulating agent is performed after moving the at least one B cell into the at least one isolation region.

40. The method of any one of embodiments 23 to 39, wherein contacting the at least one B cell with the stimulating agent is performed during the step of identifying the least one isolated B cell that produces antibodies capable of binding to the cancer cell-associated antigen.

41. The method of any one of embodiments 1 to 40, wherein identifying the at least one isolated B cell that produces antibodies capable of binding to the cancer cell-associated antigen comprises introducing the cancer cell-associated antigen into the microfluidic device.

42. The method of embodiment 41, wherein introducing the cancer cell-associated antigen into the microfluidic device comprises introducing a fluidic medium comprising the cancer cell-associated antigen into the microfluidic device.

43. The method of embodiment 42, wherein the cancer cell-associated antigen is solubilized in the fluidic medium.

44. The method of embodiment 41, wherein introducing the cancer cell-associated antigen into the microfluidic device comprises introducing micro-objects into the microfluidic device, wherein the micro-objects comprise the cancer cell-associated antigen.

45. The method of embodiment 44, wherein the micro-objects are selected from cells, liposomes, lipid nanorafts, and beads.

46. The method of embodiment 45, wherein the micro-objects are beads, and wherein the cancer cell-associated antigen is conjugated to the beads.

47. The method of embodiment 45 or 46, wherein the cancer cell-associated antigen is a membrane-associated antigen present on the cell surface of cancer cells present in the at least one tumor sample.

48. The method of embodiment 47, wherein the cancer cell-associated antigen conjugated to the beads is from a cell membrane preparation obtained from cancer cells isolated from the at least one tumor sample.

49. The method of embodiment 45, wherein the micro-objects are cancer cells.

50. The method of embodiment 49, wherein the cancer cells exhibit markers that are exhibited by cancer cells from the at least one tumor sample obtained from the patient.

51. The method of embodiment 49, wherein the cancer cells are isoloated from the at least one tumor sample.

52. The method of embodiment 49 or 50, wherein the cancer cells are isolated from one or more tumor samples obtained from a different patient.

53. The method of embodiment 52, wherein the patient from which the at least one solid tumor sample was obtained and the different patient have been diagnosed with a same type of cancer.

54. The method of embodiment 49 or 50, wherein the cancer cells are from a cancer cell line.

55. The method of any one of embodiments 41 to 54, wherein introducing the cancer cell-associated antigen into the microfluidic device comprises: flowing a fluidic medium that contains micro-objects that comprise the cancer cell-associated antigen through the flow region of the microfluidic device; and stopping the flow of the fluidic medium when at least some of the micro-objects in the medium are located in a portion of the flow region that is proximal to the at least one isolation region.

56. The method of embodiment 54, wherein introducing the cancer cell-associated antigen into the microfluidic device further comprises moving at least one of the micro-objects into at least one isolation region in the microfluidic device.

57. The method of embodiment 56, wherein moving the at least one micro-object into the at least one isolation region in the microfluidic device comprises moving at least one micro-object into each of a plurality of isolation regions.

58. The method of embodiment 56 or 57, wherein the at least one micro-object is moved into at least one isolation region that contains at least one B cell, thereby producing at least one isolation region having at least one micro-object and at least one B cell.

59. The method of embodiment 56, wherein the at least one micro-object and the at least one B cell are moved into different isolation regions.

60. The method of embodiment 59, wherein the different isolation regions are adjacent to one another within the microfluidic device.

61. The method of any one of embodiments 41 to 60, wherein identifying the at least one isolated B cell that produces antibodies capable of binding to a cancer cell-associated antigen further comprises: flowing a fluidic medium that contains a labeled antibody-binding agent through the flow region of the microfluidic device; stopping the flow of the fluidic medium when at least some of the labeled antibody-binding agent in the fluidic medium is located in a portion of the flow region that is proximal to the at least one isolation region; and monitoring binding of the labeled antibody-binding agent to the cancer cell-associated antigen.

62. The method of embodiment 61, wherein the labeled antibody-binding agent is a labeled anti-IgG antibody.

63. The method of embodiment 61 or 62, wherein the labeled antibody-binding agent is covalently bound to a fluorescent label.

64. The method of any one of embodiments 61 to 63, wherein the labeled antibody-binding agent is provided in a mixture with the cancer cell-associated antigen.

65. The method of any one of embodiments 61 to 63, wherein the labeled antibody-binding agent is provided after providing the cancer cell-associated antigen.

66. The method of any one of embodiments 61 to 65, wherein monitoring binding of the labeled antibody-binding agent to the cancer cell-associated antigen comprises imaging the microfluidic device.

67. The method of embodiment 66, wherein the imaging comprises fluorescence imaging.

68. The method of embodiment 66 or 67, wherein the imaging comprises taking a plurality of images.

69. The method of embodiment 68, wherein the plurality of images are taken at fixed time intervals.

70. The method of any one of embodiments 1 to 69, wherein the dissociated cell sample is obtained from one solid tumor sample.

71. The method of any one of esmbodiment 1 to 69, wherein the dissociated cell sample is obtained from multiple solid tumor samples.

72. The method of any one of embodiments 1 to 71, wherein providing a dissociated cell sample comprises obtaining the at least one solid tumor sample, and dissociating single cells from the at least one solid tumor sample.

73. The method of any one of embodiments 1 to 72, wherein individual cells of the dissociated cell sample are dissociated from the at least one tumor sample by: collagenase plus DNase digestion; and/or a cell dissociator instrument.

74. The method of any of embodiments 1 to 72, wherein the step of loading the dissociated cell sample comprises: fractionating the dissociated cell sample to isolate a B cell-enriched fraction that has a greater concentration of B cells than the original dissociated sample; and loading the B cell-enriched fraction into the microfluidic device.

75. The method of embodiment 74, wherein the fractionating comprises selecting B cells from the dissociated cell sample using at least one marker chosen from CD19, CD20, IgM, IgD, CD38, CD27, CD138, PNA, and GL7.

76. The method of any one of embodiments 1 to 75, wherein prior to loading the dissociated cell sample or the B cell-enriched fraction into the microfluidic device, the method further comprises labeling cancer cells in the dissociated cell sample with a detectable marker.

77. The method of any of embodiments 1 to 76, wherein the step of loading the dissociated cell sample further comprises: fractionating the dissociated cell sample to isolate a cancer cell-enriched fraction that has a greater concentration of cancer cells than the original dissociated sample; and loading the cancer cell-enriched fraction into the microfluidic device.

78. The method of embodiment 76, wherein the method further comprises selecting at least one cancer cell for movement into at least one isolation region.

79. The method of embodiment 77, wherein the method further comprises selecting at least one cancer cell for movement into at least one isolation region, and wherein the at least one cancer cell is selected based on detection of the detectable marker.

80. The method of embodiment 79, wherein the at least one cancer cells is loaded into the microfluidic device and moved into the isolation region of the microfluidic device before the B cells are loaded into the microfluidic device and moved into the isolation regions.

81. The method of embodiment 77, wherein the cancer cell-enriched fraction is loaded into the flow region of the microfluidic device after the B cells are loaded into the microfluidic device and moved into the isolation regions.

82. The method of embodiment 77, wherein the cancer cells do not enter the isolation regions.

83. The method of any one of embodiments 76 to 82, wherein the cancer cells are selected from the dissociated cell sample or enriched using at least one marker specific for the cancer (e.g., any of the cancer-associated markers disclosed herein).

84. The method of any one of embodiments 76 to 83, wherein the cancer cells are separated from the dissociated cell sample or enriched using morphological differences.

85. The method of any one of embodiments 76 to 84, wherein the cancer cells are selected from the dissociated cell sample using at least one marker that is down-regulated in cancer cells, to isolate normal cells away from the cancer cells.

86. The method of any one of embodiments 74 to 85, wherein the B cells and/or cancer cells are selected from the dissociated cell sample by FACS.

87. The method of any one of embodiments 74 to 86, wherein the B cells and/or cancer cells are selected from the dissociated cell sample by magnetic bead-based sorting.

88. The method of any one of embodiments 1 to 87, wherein the solid tumor sample is a tumor biopsy.

89. The method of any one of embodiments 1 to 88, wherein the tumor that yielded the at least one tumor sample has a tertiary lymphoid structure.

90. The method of any one of embodiments 1 to 89, wherein the tumor that yielded the at least one tumor sample is a breast cancer, genitourinary cancer (such as a cancer originating in the urinary tract, such as in the kidneys (e.g., renal cell carcinoma), ureters, bladder, or urethra; cancer of the male reproductive tract (e.g., testicular cancer, prostate cancer, or a cancer of the seminal vesicles, seminal ducts, or penis); or of the female reproductive tract (e.g., ovarian cancer, uterine cancer, cervical cancer, vaginal cancer, or a cancer of the fallopian tubes)), a cancer of the nervous system (such as neuroblastoma), intestinal cancer (such as colorectal cancer), lung cancer, melanoma, or another type of cancer.

91. The method of embodiment 90, wherein the tumor is a medullary breast cancer.

92. The method of embodiment 90, wherein the tumor is a mesothelioma.

93. The method of any one of embodiments 1 to 92, wherein the method further comprises: exporting the at least one identified B cell, or a population of cloned B cells derived therefrom, from the microfluidic device.

94. The method of embodiment 93, wherein each identified B cell, or the population of cloned B cells derived therefrom, is exported individually.

95. The method of any one of embodiments 1 to 94, further comprising: performing antibody sequencing on the at least one identified B cell, or on some or all of a clonal population of B cells derived therefrom.

96. The method of embodiment 95, wherein performing antibody sequencing comprises determining paired heavy chain and light chain variable domain antibody sequences from the at least one identified B cell, or from some or all of the clonal population of B cells derived therefrom.

97. The method of any one of embodiments 1 to 96, wherein the method further comprises generating an antibody therapeutic comprising some or all of the paired heavy chain and light chain variable domain sequences from the at least one identified B cell.

98. The method of any one of embodiments 1 to 97, wherein T or NK cells are present in the dissociated cell sample.

99. The method of embodiment 98, wherein the method further comprises performing a selection on the dissociated cell sample to isolate a fraction that has a greater concentration of T or NK cells than the original dissociated sample.

100. The method of embodiment 98 or 99, wherein the T or NK cells are obtained from the same patient's solid tumor sample(s).

101. The method of any one of embodiments 98 to 100, wherein the T cells are separated from the dissociated cell sample by using at least one marker chosen from CD4, CD8, CD25, CD45RA, CD45RO, CD62L, CD69, and CD3; or wherein the NK cells are separated from the dissociated cell sample by using CD56 as a marker.

102. The method of any one of embodiments 98 to 101, wherein individual T or NK cells are selected and cloned from the patient.

103. The method of any one of embodiments 1 to 102, wherein the method comprises using a microfluidic device to identify at least one B cell that produces antibodies capable of binding to both the patient's cancer cells and cancer cells from another source.

104. The method of any one of embodiments 1 to 103, wherein the method further comprises using a microfluidic device to identify whether the antibodies produced by the B cell(s) are capable of binding to non-cancer cells.

105. The method of embodiment 104, wherein the non-cancer cells and the cancer cells are from the patient that provided the at least one tumor sample.

106. The method of embodiment 104 or 105, wherein the same microfluidic device is used to identify binding of the antibodies to cancer and non-cancer cells.

107. The method of embodiment 106, wherein the cancer and non-cancer cells are loaded sequentially in the same flow path.

108. A method of treating a patient having cancer, the method comprising treating the patient with an antibody or fragment thereof produced by the method of any one of embodiments 1 to 107.

109. The method of embodiment 108, wherein the tumor sample is taken from the same patient who is treated.

110. The method of embodiment 108 or 109, wherein the time from obtaining the tumor sample to treatment is at most about 2 months.

111. The method of any one of embodiments 108 to 110, wherein the antibody or fragment thereof is a single chain antibody.

112. The method of any one of embodiments 108 to 110, wherein the antibody or fragment thereof has two heavy chains and two light chains.

113. The method of any one of embodiments 108 to 111, wherein the antibody is displayed on an engineered T or NK cell.

114. The method of embodiment 113, wherein the engineered T cell is a chimeric antigen receptor T cell or the engineered NK cell is a chimeric antigen receptor NK cell.

115. The method of embodiment 113 or 114, wherein the T or NK cell was obtained from the same patient prior to being engineered to display the antibody.

116. The method of embodiment 115, wherein the T or NK cell was obtained from the patient's tumor sample.

117. The method of any one of embodiments 108 to 116, wherein the antibody or fragment thereof is administered in combination with another therapy.

118. The method of claim 117, wherein the combination therapy is surgery, radiation, chemotherapy, CAR-T cell therapy, CAR-NK cell therapy, T cell therapy, other immunotherapy, or administration of immune-stimulatory molecule or a tumor-specific virus.

119. A method of labeling or detecting cancer in a patient comprising administering an antibody or fragment thereof conjugated to a detectable label, wherein the antibody or fragment thereof is produced by the method of any one of embodiments 1 to 107.

120. An engineered antibody construct comprising: at least the heavy chain CDRs of an antibody identified by the method of any one of embodiments 1 to 107; at least the light chain CDRs of an antibody identified by the method of any one of embodiments 1 to 107; at least the heavy and light chain CDRs of an antibody identified by the method of any one of embodiments 1 to 107; at least the heavy chain variable region of an antibody identified by the method of any one of embodiments 1 to 107; at least the light chain variable region of an antibody identified by the method of any one of embodiments 1 to 107; or at least the heavy and light chain variable regions of an antibody identified by the method of any one of embodiments 1 to 107.

121. An engineered antibody construct, wherein the engineered antibody construct is a variant of the antibody identified by the method of any one of embodiments 1 to 107 (e.g., a variant having 1 to 20, 1 to 15, 1 to 10, or 1 to 5 amino acid substitutions, additions, or deletions in the light chain and/or heavy chain variable regions of the identified antibody).

122. The engineered antibody construct of embodiment 120 or 121, wherein the construct is a Fab, Fab'(2), scFv, multivalent scFv, minibody, bispecific antibody, or camel variable functional heavy chain domain.

123. An engineered T or NK cell comprising an antibody or fragment thereof displayed on its external surface, wherein the antibody or fragment thereof is identified by the method of any one of embodiments 1 to 107.

124. The engineered T or NK cell of embodiment 123, wherein the T or NK cell and the antibody or fragment thereof were obtained from the same patient.

125. A method of preparing an engineered T cell comprising an antibody or fragment thereof displayed on its external surface, the method comprising: identifying an antibody that binds to a tumor sample according to the method of any one of embodiments 1 to 107; and genetically engineering a T cell to express the antibody or a fragment thereof.

126. The method of embodiment 125, wherein the T cell, the B cell expressing the antibody, and the tumor sample were obtained from the same patient.

127. A method of preparing an engineered NK cell comprising an antibody or fragment thereof displayed on its external surface, the method comprising: identifying an antibody that binds to a tumor sample according to the method of any one of embodiments 1 to 107; and genetically engineering a NK cell to express the antibody or a fragment thereof.

128. The method of embodiment 127, wherein the NK cell, the B cell expressing the antibody, and the tumor sample were obtained from the same patient.

EQUIVALENTS

The foregoing written specification is considered to be sufficient to enable one skilled in the art to practice the embodiments. The foregoing description and Examples detail certain embodiments and describes the best mode contemplated. It will be appreciated, however, that no matter how detailed the foregoing may appear in text, the embodiment may be practiced in many ways and should be construed in accordance with the appended claims and any equivalents thereof.

What is claimed is:

1. A method of identifying an isolated B cell that produces antibodies capable of binding to a cancer cell-associated antigen comprising:
    loading a dissociated cell sample from at least one solid tumor sample obtained from a patient into a microfluidic device having at least one flow region and at least one sequestration chamber comprising an isolation region, wherein the isolation region is fluidically connected to the flow region;
    moving at least one B cell from the dissociated cell sample into at least one isolation region in the microfluidic device, thereby obtaining at least one isolated B cell; and
    identifying at least one isolated B cell that produces antibodies capable of binding to a cancer cell-associated antigen by introducing the cancer cell-associated antigen into the microfluidic device.

2. The method of claim 1, wherein moving the at least one B cell into the at least one isolation region comprises using DEP force to move the at least one B cell.

3. The method of claim 1, wherein the at least one B cell is moved into the at least one isolation region using gravity and/or localized fluid flow.

4. The method of claim 1, further comprising:
    contacting the at least one B cell with a stimulating agent that stimulates B cell activation.

5. The method of claim 4, wherein the stimulating agent comprises one or more CD40L+ feeder cells.

6. The method of claim 5, wherein the one or more CD40L+feeder cells is/are T cells or a derivative thereof.

7. The method of claim 4, wherein the stimulating agent further comprises a CpG oligonucleotide.

8. The method of claim 4, wherein the at least one B cells is contacted with the stimulating agent for a period of one to ten days.

9. The method of claim 8, wherein the at least one B cell is contacted with the stimulating agent substantially continuously for said period of one to ten days.

10. The method of claim 4, further comprising:
providing culture medium to the at least one B cell, wherein the culture medium comprises one or more growth-inducing agents that promote B cell expansion.

11. The method of claim 10, wherein the at least one B cells is provided culture medium for a period of one to ten days.

12. The method of claim 10, wherein the steps of contacting the at least one B cell with the stimulating agent and providing culture medium to the at least one B cell are performed over a substantially coextensive period of time.

13. The method of claim 4, wherein contacting the at least one B cell with the stimulating agent is performed at least prior to loading the dissociated cell sample into the microfluidic device.

14. The method of claim 4, wherein contacting the at least one B cell with the stimulating agent is performed at least after moving the at least one B cell into the at least one isolation region.

15. The method of claim 4, wherein contacting the at least one B cell with the stimulating agent is performed at least during the step of identifying the least one isolated B cell that produces antibodies capable of binding to the cancer cell-associated antigen.

16. The method of claim 1, wherein introducing the cancer cell-associated antigen into the microfluidic device comprises introducing micro-objects that comprise the cancer cell-associated antigen into the microfluidic device, and further wherein the micro-objects are selected from cells, liposomes, lipid nanorafts, and beads.

17. The method of claim 16, wherein the micro-objects are cancer cells.

18. The method of claim 17, wherein the cancer cells exhibit markers that are exhibited by cancer cells from the patient's at least one tumor sample.

19. The method of claim 17, wherein the cancer cells are isolated from the at least one tumor sample.

20. The method of claim 18, wherein the cancer cells are isolated from one or more tumor samples obtained from a different patient.

21. The method of claim 17, wherein the cancer cells are from a cancer cell line.

22. The method of claim 1, wherein individual cells of the dissociated cell sample are dissociated from the at least one tumor sample by:
   a. collagenase plus DNase digestion; and/or
   b. a cell dissociator instrument.

* * * * *